US011098289B2

(12) United States Patent
Baca et al.

(10) Patent No.: US 11,098,289 B2
(45) Date of Patent: Aug. 24, 2021

(54) URICASE SEQUENCES AND METHODS OF TREATMENT

(71) Applicant: MedImmune, LLC, Gaithersburg, MD (US)

(72) Inventors: Manuel Baca, Gaithersburg, MD (US); Andrew C. Nyborg, Gaithersburg, MD (US)

(73) Assignee: MedImmune, LLC, Gaitherburg, MD (US)

( * ) Notice: Subject to any disclaimer, the term of this patent is extended or adjusted under 35 U.S.C. 154(b) by 123 days.

(21) Appl. No.: 15/573,993

(22) PCT Filed: May 13, 2016

(86) PCT No.: PCT/US2016/032415
§ 371 (c)(1),
(2) Date: Nov. 14, 2017

(87) PCT Pub. No.: WO2016/187026
PCT Pub. Date: Nov. 24, 2016

(65) Prior Publication Data
US 2018/0258406 A1    Sep. 13, 2018

Related U.S. Application Data

(60) Provisional application No. 62/162,280, filed on May 15, 2015.

(51) Int. Cl.
| C12N 9/06 | (2006.01) |
| A61P 13/02 | (2006.01) |
| A61K 9/00 | (2006.01) |
| A61K 38/00 | (2006.01) |

(52) U.S. Cl.
CPC .......... *C12N 9/0048* (2013.01); *A61K 9/0019* (2013.01); *A61P 13/02* (2018.01); *C12Y 107/03003* (2013.01); *A61K 38/00* (2013.01)

(58) Field of Classification Search
None
See application file for complete search history.

(56) References Cited

U.S. PATENT DOCUMENTS

| 8,148,123 B2 | 4/2012 | Hartman | |
| 2011/0214199 A1 | 9/2011 | Coffin | |
| 2013/0305398 A1 | 11/2013 | Coffin | |
| 2013/0330803 A1* | 12/2013 | Hartman | .............. C12N 9/0046 435/191 |
| 2019/0048327 A1 | 2/2019 | Baca | |

FOREIGN PATENT DOCUMENTS

| WO | 2000007629 | 2/2000 |
| WO | 2000008196 | 2/2000 |
| WO | 2001059078 | 8/2001 |
| WO | 2006110761 | 10/2006 |
| WO | 2006110819 | 10/2006 |
| WO | 2010151823 | 12/2010 |
| WO | 2016187026 | 11/2016 |

OTHER PUBLICATIONS

Chua, C. et al., "Use of Polyethylene Glycol-Modified Uricase (PEG-uricase) to Treat Hyperuricemia in a Patient with Non-Hodgkin Lymphoma", Ann Intern Med., 109(2):114-7, (1988).
Database UniProt [Online] May 1, 2000 (May 1, 2000), "RecName: Full=Uricase {ECO:0000256IPIRNR: PIRNR000241, ECO: 0000256IRuleBase:RU004455}; EC=1.7.3.3 {ECO:0000256I PIRNR:PIRNR000241, ECO:0000256IRuleBase:RU004455}; AltName: Full=Urate oxidase {ECO:0000256IPIRNR:PIRNR000241};",retrieved from EBI accession No. UniProt:Q9RV70, Database accession No. Q9RV70.
Database UniProt [Online] Jul. 13, 2010 (Jul. 13, 2010), "RecName: Full=Uricase {ECO:0000256IPIRNR: PIRNR000241, ECO: 0000256IRuleBase:RU004455}; EC=1.7.3.3 {ECO:0000256I PIRNR:PIRNR000241, ECO:0000256IRuleBase:RU004455}; AltName: Full=Urate oxidase {ECO:0000256IPIRNR:PIRNR000241};", retrieved from EBI accession No. UniProt:D5WQV0 Database accession No. D5WQV0.
Database UniProt [Online] Nov. 14, 2006 (Nov. 14, 2006), "RecName: Full=Uricase {ECO:0000256IPIRNR: PIRNR000241, ECO: 0000256IRuleBase:RU004455}; EC=1.7.3.3 {ECO:0000256I PIRNR:PIRNR000241, ECO:0000256IRuleBase:RU004455}; AltName: Full=Urate oxidase {ECO:0000256IPIRNR:PIRNR000241};", retrieved from EBI accession No. UniProt:Q02C45 Database accession No. Q02C45.
Database UniProt [Online] Apr. 5, 2011 (Apr. 5, 2011), "RecName: Full=Uricase {ECO:0000256IPIRNR: PIRNR000241, ECO: 0000256IRuleBase:RU004455}; EC=1.7.3.3 {ECO:0000256I PIRNR:PIRNR000241, ECO:0000256IRuleBase:RU004455}; AltName: Full=Urate oxidase {ECO:0000256IPIRNR:PIRNR000241};", retrieved from EBI accession No. UniProt:E8UXZ9 Database accession No. E8UXZ9.
Database UniProt [Online] Apr. 5, 2011 (Apr. 5, 2011), "RecName: Full=Uricase {ECO:0000256IPIRNR: PIRNR000241, ECO: 0000256IRuleBase:RU004455}; EC=1.7.3.3 {ECO:0000256I PIRNR:PIRNR000241, ECO:0000256IRuleBase:RU004455}; AltName: Full=Urate oxidase {ECO:0000256IPIRNR:PIRNR000241};", retrieved from EBI accession No. UniProt:E8WYY0 Database accession No. E8WYY0.
Database, Geneseq [Online], Aug. 27, 2003, "Uricase", retrieved from EBI accession No. GSP:AAW24553.
Database, UniProt [Online], Jun. 13, 2006, "RecName: Full= Uricase {ECO:0000256IPIRNR000241, ECO:0000256I RuleBase:RU00455}; EC=1.7.3.3 {ECO:0000256I PIRNR:PI RNR000241, ECO:0000256IRuleBase:RU004455}; AltName: Full= Urate oxidase {ECO:0000256IPIRNR:PIRNR000241};",retrieved from EBI accession No. UniProt:O1 J399 Database accession No. 01 J399.

(Continued)

Primary Examiner — Paul J Holland
(74) Attorney, Agent, or Firm — Dennis A. Bennett; Chris Marion; Stephanie M. Greer

(57) ABSTRACT

Described are improved uricase sequences having beneficial effects and methods of treating patients suffering from hyperuricemia.

8 Claims, 18 Drawing Sheets

Specification includes a Sequence Listing.

(56) References Cited

OTHER PUBLICATIONS

International Application No. PCT/US2016/032415; International Preliminary Report on Patentability; dated Nov. 21, 2017; 5 pages.
International Application No. PCT/US2016/032415; International Search Report and Written Opinion of the International Searching Authority, dated Sep. 2, 2016; 8 pages.
Joshi, M. et al., "Draft Genome Sequence of Arthrobacter Crystallopoietes Strain BAB-32, Revealing Genes of Bioremediation", Genome Announcements, 1:1-2, (2013).
Juan, E. et al., "Structures of Arthrobacter Globiformis Urate Oxidase-Ligand Complexes", Acta Crystallogr D Biol Crystallogr., D64(Pt 8):815-22, (2008).
Suzuki, K. et al., "Molecular Cloning and Expression of Uricase Gene from Arthrobacter Globiformis in *Escherichia coli* and Characterization of the Gene Product", J Biosci Bioeng., 98(3):153-8, (2004).
U.S. Appl. No. 16/167,765, filed Oct. 23, 2018; 65 pages.
Wilkinson, et al., "HucR, A Novel Uric Acid-Responsive Member of the MarR Family of Transcriptional Regulators from Deinococcus Radiodurans", J Biol Chem., 279:51442-50, (2004).
Anonymous. Uniprot D0VWQ1 input. Uricasa (uox) from Arthrobacter globiformis URL: https://www.uniprot.org/uniprot/D0VWQ1. Access Date: May 23, 2019. Date of incorporation into database: Apr. 5, 2011.
U.S. Appl. No. 16/167,765; Non-Final Office Action, dated Sep. 27, 2019; 19 pages.
Database UniProtKB/Swiss-Prot: D0VWQ1.1, Jan. 4, 2015, retrieved from the internet at: https://www.ncbi.nlm.nih.gov/protein/327488515?sat=21&satkey=23772744.

* cited by examiner

*Deinococcus geothermalis*

*Deinococcus radiodurans*

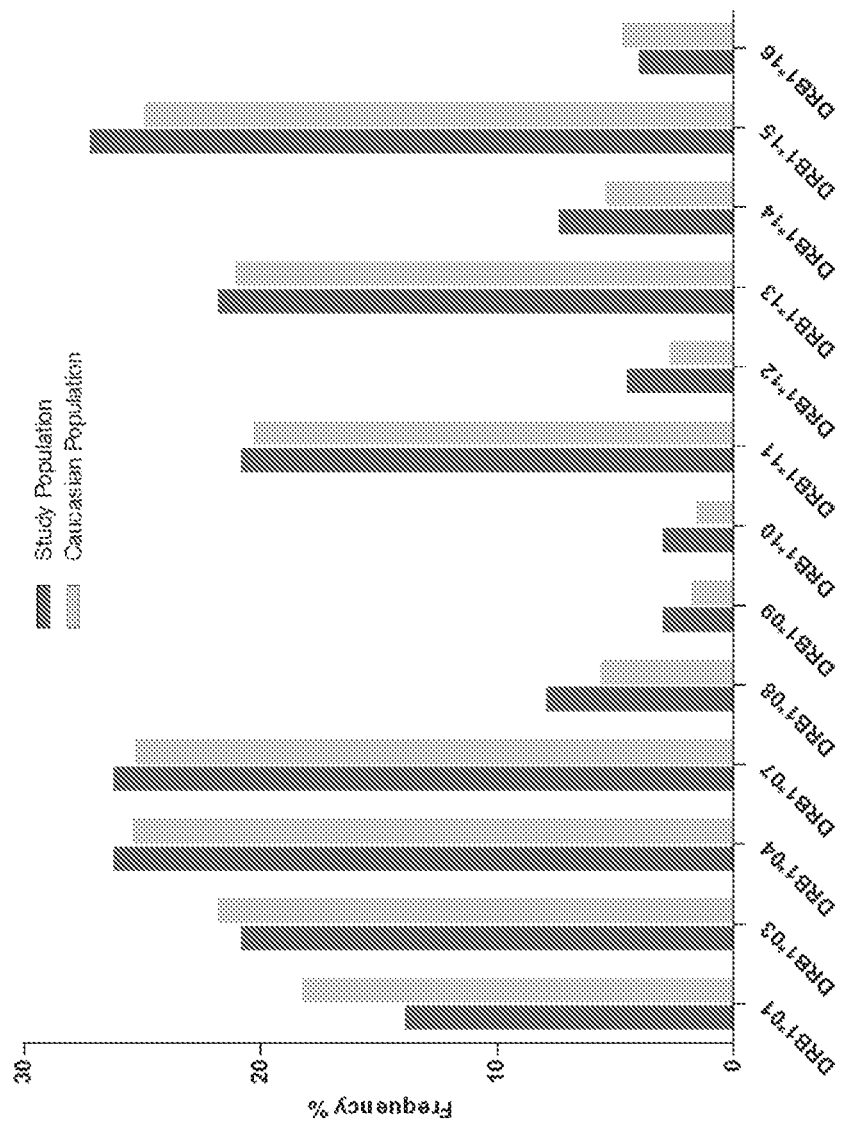

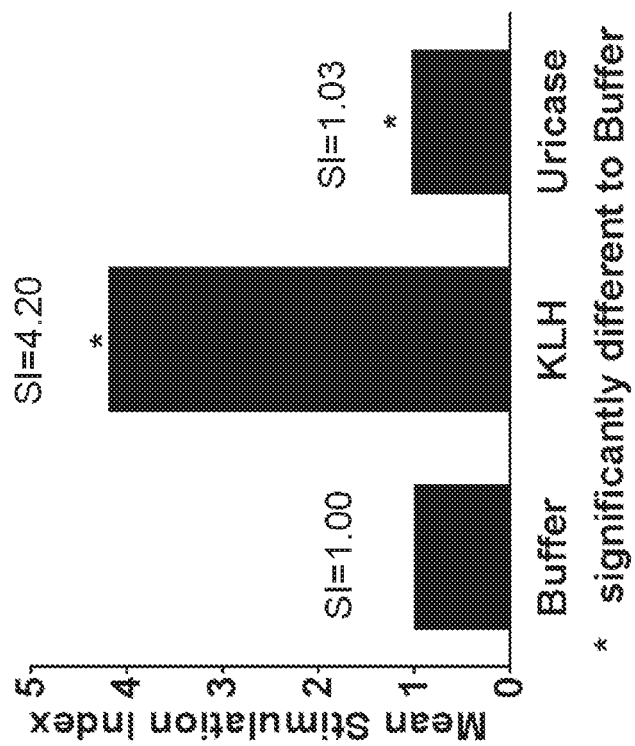

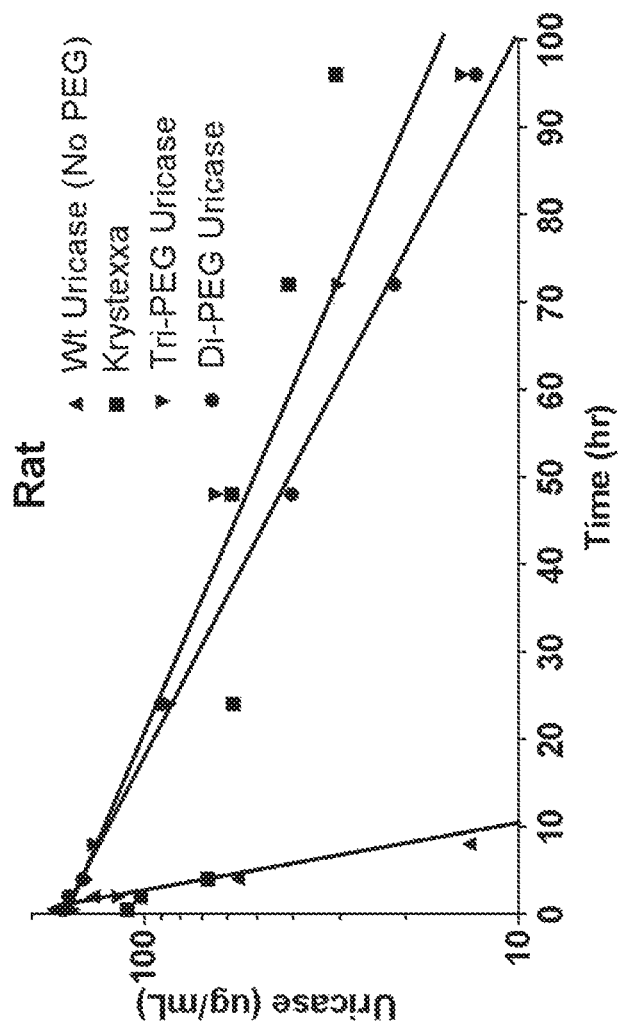

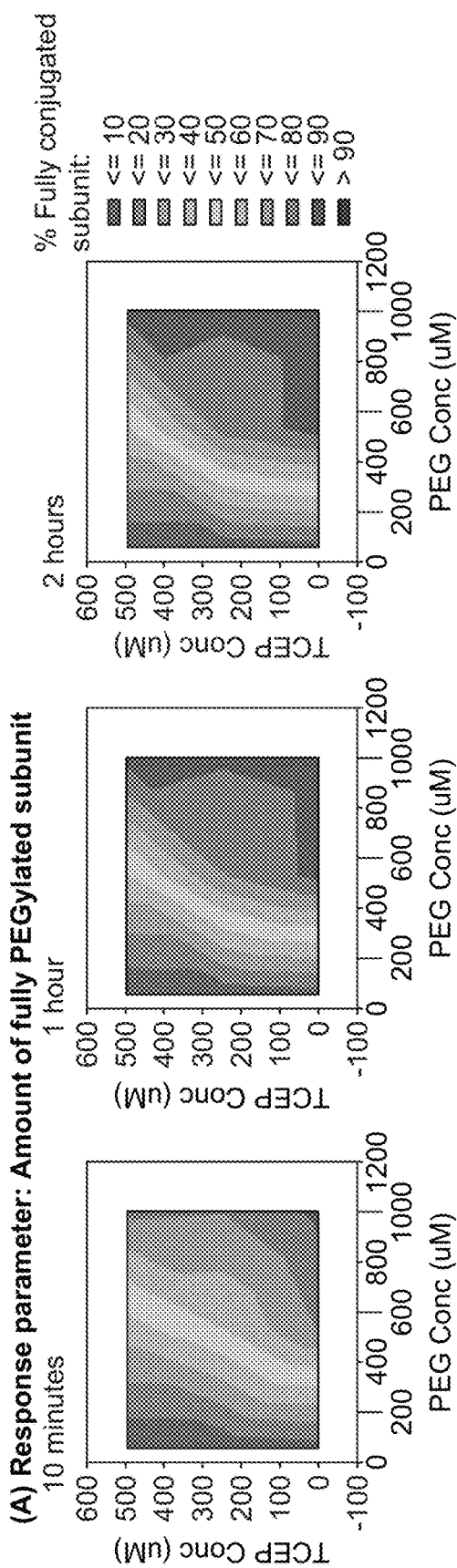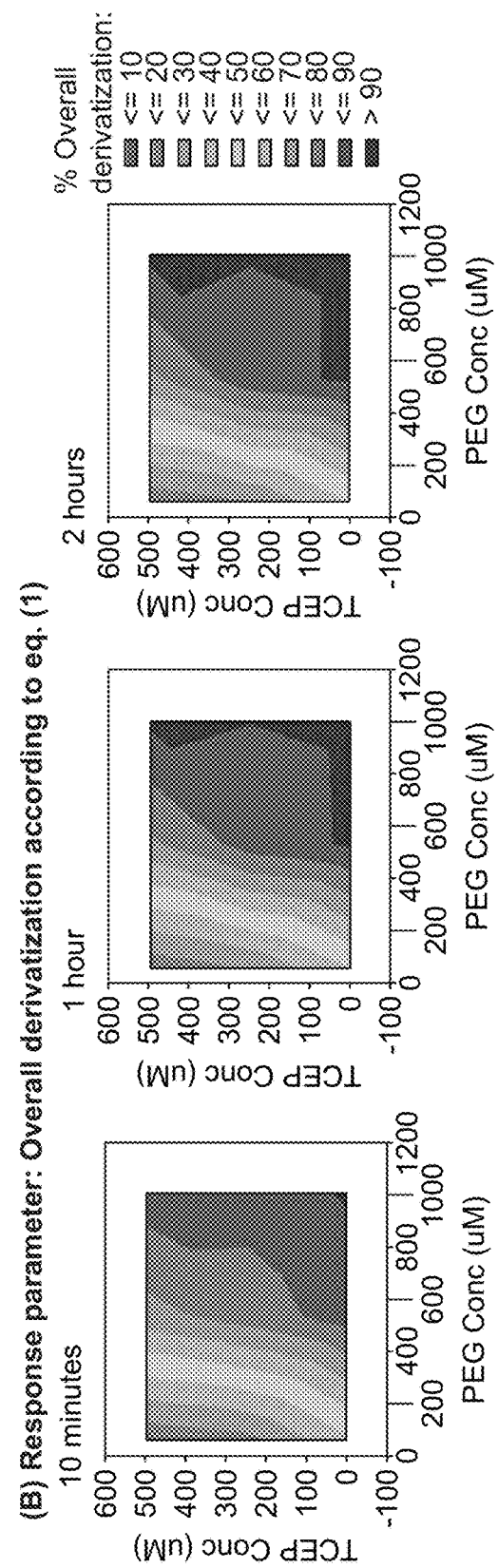
FIG. 14A
FIG. 14B

SEQUENCE LISTING

```
<160> NUMBER OF SEQ ID NOS: 34

<210> SEQ ID NO 1
<211> LENGTH: 290
<212> TYPE: PRT
<213> ORGANISM: Artificial Sequence
<220> FEATURE:
<223> OTHER INFORMATION: Modified Arthrobacter globiformis Uricase,
      modified N-terminus, SGD, 2-Cys, C-terminal truncation (SGD V1 C2)

<400> SEQUENCE: 1

Met Ala Thr Ala Glu Thr Ser Thr Gly Cys Lys Val Val Leu Gly Gln
1               5                  10                  15

Asn Gln Tyr Gly Lys Ala Glu Val Arg Leu Val Lys Val Thr Arg Cys
            20                  25                  30

Thr Ala Arg His Glu Ile Gln Asp Leu Asn Val Thr Ser Gln Leu Ser
        35                  40                  45

Gly Asp Phe Glu Ala Ala His Thr Ala Gly Asp Asn Ala His Val Val
    50                  55                  60

Ala Thr Asp Thr Gln Lys Asn Thr Val Tyr Ala Phe Ala Arg Asp Gly
65                  70                  75                  80

Phe Ala Thr Thr Glu Glu Phe Leu Leu Arg Leu Gly Lys His Phe Thr
                85                  90                  95

Glu Gly Phe Asp Trp Val Thr Gly Gly Arg Trp Ala Ala Gln Gln Phe
            100                 105                 110

Phe Trp Asp Arg Ile Asn Asp His Asp His Ala Phe Ser Arg Asn Lys
        115                 120                 125

Ser Glu Val Arg Thr Ala Val Leu Glu Ile Ser Gly Ser Glu Gln Ala
    130                 135                 140

Ile Val Ala Gly Ile Glu Gly Leu Thr Val Leu Lys Ser Thr Gly Ser
145                 150                 155                 160

Glu Phe His Gly Phe Pro Arg Asp Lys Tyr Thr Thr Leu Gln Glu Thr
                165                 170                 175

Thr Asp Arg Ile Leu Ala Thr Asp Val Ser Ala Arg Trp Arg Tyr Asn
            180                 185                 190

Thr Val Glu Val Asp Phe Asp Ala Val Tyr Ala Ser Val Arg Gly Leu
        195                 200                 205

Leu Leu Lys Ala Phe Ala Glu Thr His Ser Leu Ala Leu Gln Gln Thr
```

```
            210                 215                 220
Met Tyr Glu Met Gly Arg Ala Val Ile Glu Thr His Pro Glu Ile Asp
225                 230                 235                 240

Glu Ile Lys Met Ser Leu Pro Asn Lys His His Phe Leu Val Asp Leu
                245                 250                 255

Gln Pro Phe Gly Gln Asp Asn Pro Asn Glu Val Phe Tyr Ala Ala Asp
            260                 265                 270

Arg Pro Tyr Gly Leu Ile Glu Ala Thr Ile Gln Arg Glu Gly Ser Arg
        275                 280                 285

Ala Asp
    290

<210> SEQ ID NO 2
<211> LENGTH: 290
<212> TYPE: PRT
<213> ORGANISM: Artificial Sequence
<220> FEATURE:
<223> OTHER INFORMATION: Modified Arthrobacter globiformis Uricase,
      modified N-terminus, RGD, 2-Cys, C-terminal truncation (RGD V1 C2)

<400> SEQUENCE: 2

Met Ala Thr Ala Glu Thr Ser Thr Gly Cys Lys Val Val Leu Gly Gln
1               5                   10                  15

Asn Gln Tyr Gly Lys Ala Glu Val Arg Leu Val Lys Val Thr Arg Cys
            20                  25                  30

Thr Ala Arg His Glu Ile Gln Asp Leu Asn Val Thr Ser Gln Leu Arg
        35                  40                  45

Gly Asp Phe Glu Ala Ala His Thr Ala Gly Asp Asn Ala His Val Val
    50                  55                  60

Ala Thr Asp Thr Gln Lys Asn Thr Val Tyr Ala Phe Ala Arg Asp Gly
65                  70                  75                  80

Phe Ala Thr Thr Glu Glu Phe Leu Leu Arg Leu Gly Lys His Phe Thr
                85                  90                  95

Glu Gly Phe Asp Trp Val Thr Gly Gly Arg Trp Ala Ala Gln Gln Phe
            100                 105                 110

Phe Trp Asp Arg Ile Asn Asp His Asp His Ala Phe Ser Arg Asn Lys
        115                 120                 125

Ser Glu Val Arg Thr Ala Val Leu Glu Ile Ser Gly Ser Glu Gln Ala
    130                 135                 140

Ile Val Ala Gly Ile Glu Gly Leu Thr Val Leu Lys Ser Thr Gly Ser
145                 150                 155                 160

Glu Phe His Gly Phe Pro Arg Asp Lys Tyr Thr Thr Leu Gln Glu Thr
                165                 170                 175

Thr Asp Arg Ile Leu Ala Thr Asp Val Ser Ala Arg Trp Arg Tyr Asn
            180                 185                 190

Thr Val Glu Val Asp Phe Asp Ala Val Tyr Ala Ser Val Arg Gly Leu
        195                 200                 205

Leu Leu Lys Ala Phe Ala Glu Thr His Ser Leu Ala Leu Gln Gln Thr
    210                 215                 220

Met Tyr Glu Met Gly Arg Ala Val Ile Glu Thr His Pro Glu Ile Asp
225                 230                 235                 240

Glu Ile Lys Met Ser Leu Pro Asn Lys His His Phe Leu Val Asp Leu
                245                 250                 255

Gln Pro Phe Gly Gln Asp Asn Pro Asn Glu Val Phe Tyr Ala Ala Asp
            260                 265                 270
```

```
Arg Pro Tyr Gly Leu Ile Glu Ala Thr Ile Gln Arg Glu Gly Ser Arg
        275                 280                 285

Ala Asp
    290

<210> SEQ ID NO 3
<211> LENGTH: 290
<212> TYPE: PRT
<213> ORGANISM: Artificial Sequence
<220> FEATURE:
<223> OTHER INFORMATION: Modified Arthrobacter globiformis Uricase,
      modified N-terminus, RGD variants, 2-Cys, C-terminal truncation
      (RGD variants of V1 C2)
<220> FEATURE:
<221> NAME/KEY: MISC_FEATURE
<222> LOCATION: (48)..(48)
<223> OTHER INFORMATION: X is either R or any natural amino acid except
      C
<220> FEATURE:
<221> NAME/KEY: MISC_FEATURE
<222> LOCATION: (49)..(49)
<223> OTHER INFORMATION: X is either G or any natural amino acid except
      C
<220> FEATURE:
<221> NAME/KEY: MISC_FEATURE
<222> LOCATION: (50)..(50)
<223> OTHER INFORMATION: X is either D or any natural amino acid except
      C

<400> SEQUENCE: 3

Met Ala Thr Ala Glu Thr Ser Thr Gly Cys Lys Val Val Leu Gly Gln
1               5                   10                  15

Asn Gln Tyr Gly Lys Ala Glu Val Arg Leu Val Lys Val Thr Arg Cys
            20                  25                  30

Thr Ala Arg His Glu Ile Gln Asp Leu Asn Val Thr Ser Gln Leu Xaa
        35                  40                  45

Xaa Xaa Phe Glu Ala Ala His Thr Ala Gly Asp Asn Ala His Val Val
    50                  55                  60

Ala Thr Asp Thr Gln Lys Asn Thr Val Tyr Ala Phe Ala Arg Asp Gly
65                  70                  75                  80

Phe Ala Thr Thr Glu Glu Phe Leu Leu Arg Leu Gly Lys His Phe Thr
                85                  90                  95

Glu Gly Phe Asp Trp Val Thr Gly Gly Arg Trp Ala Ala Gln Gln Phe
            100                 105                 110

Phe Trp Asp Arg Ile Asn Asp His Asp His Ala Phe Ser Arg Asn Lys
        115                 120                 125

Ser Glu Val Arg Thr Ala Val Leu Glu Ile Ser Gly Ser Glu Gln Ala
    130                 135                 140

Ile Val Ala Gly Ile Glu Gly Leu Thr Val Leu Lys Ser Thr Gly Ser
145                 150                 155                 160

Glu Phe His Gly Phe Pro Arg Asp Lys Tyr Thr Thr Leu Gln Glu Thr
                165                 170                 175

Thr Asp Arg Ile Leu Ala Thr Asp Val Ser Ala Arg Trp Arg Tyr Asn
            180                 185                 190

Thr Val Glu Val Asp Phe Asp Ala Val Tyr Ala Ser Val Arg Gly Leu
        195                 200                 205

Leu Leu Lys Ala Phe Ala Glu Thr His Ser Leu Ala Leu Gln Gln Thr
    210                 215                 220

Met Tyr Glu Met Gly Arg Ala Val Ile Glu Thr His Pro Glu Ile Asp
225                 230                 235                 240

Glu Ile Lys Met Ser Leu Pro Asn Lys His His Phe Leu Val Asp Leu
```

```
            245                 250                 255

Gln Pro Phe Gly Gln Asp Asn Pro Asn Glu Val Phe Tyr Ala Ala Asp
            260                 265                 270

Arg Pro Tyr Gly Leu Ile Glu Ala Thr Ile Gln Arg Glu Gly Ser Arg
        275                 280                 285

Ala Asp
    290

<210> SEQ ID NO 4
<211> LENGTH: 301
<212> TYPE: PRT
<213> ORGANISM: Artificial Sequence
<220> FEATURE:
<223> OTHER INFORMATION: Genus sequence, with optional N-terminal
      modification, 4 possible cysteines, R/SGD, optionally with or
      without C-terminal truncation
<220> FEATURE:
<221> NAME/KEY: MISC_FEATURE
<222> LOCATION: (1)..(301)
<223> OTHER INFORMATION: From at least one, two, three, or four
      cysteines are included in the sequence
<220> FEATURE:
<221> NAME/KEY: MISC_FEATURE
<222> LOCATION: (2)..(2)
<223> OTHER INFORMATION: X is either present or absent, and if present
      is T
<220> FEATURE:
<221> NAME/KEY: MISC_FEATURE
<222> LOCATION: (11)..(11)
<223> OTHER INFORMATION: X is either T or C
<220> FEATURE:
<221> NAME/KEY: MISC_FEATURE
<222> LOCATION: (33)..(33)
<223> OTHER INFORMATION: X is either N or C
<220> FEATURE:
<221> NAME/KEY: MISC_FEATURE
<222> LOCATION: (49)..(49)
<223> OTHER INFORMATION: X is either R or S
<220> FEATURE:
<221> NAME/KEY: MISC_FEATURE
<222> LOCATION: (119)..(119)
<223> OTHER INFORMATION: X is either N or C
<220> FEATURE:
<221> NAME/KEY: MISC_FEATURE
<222> LOCATION: (142)..(142)
<223> OTHER INFORMATION: X is either S or C
<220> FEATURE:
<221> NAME/KEY: MISC_FEATURE
<222> LOCATION: (292)..(301)
<223> OTHER INFORMATION: One or more amino acids in the C-terminus are
      optional

<400> SEQUENCE: 4

Met Xaa Ala Thr Ala Glu Thr Ser Thr Gly Xaa Lys Val Val Leu Gly
1               5                   10                  15

Gln Asn Gln Tyr Gly Lys Ala Glu Val Arg Leu Val Lys Val Thr Arg
            20                  25                  30

Xaa Thr Ala Arg His Glu Ile Gln Asp Leu Asn Val Thr Ser Gln Leu
        35                  40                  45

Xaa Gly Asp Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110
```

```
Phe Phe Trp Asp Arg Ile Xaa Asp His Asp His Ala Phe Ser Arg Asn
            115                 120                 125

Lys Ser Glu Val Arg Thr Ala Val Leu Glu Ile Ser Gly Xaa Glu Gln
130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
            165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
            195                 200                 205

Leu Leu Leu Lys Ala Phe Ala Glu Thr His Ser Leu Ala Leu Gln Gln
210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
            245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Glu Gly Ser
            275                 280                 285

Arg Ala Asp His Pro Ile Trp Ser Asn Ile Ala Gly Phe
            290                 295                 300

<210> SEQ ID NO 5
<211> LENGTH: 300
<212> TYPE: PRT
<213> ORGANISM: Artificial Sequence
<220> FEATURE:
<223> OTHER INFORMATION: Genus sequence, with modified N-terminus, with
      4 possible cysteines, SGD, optionally with or without C-terminal
      truncation
<220> FEATURE:
<221> NAME/KEY: MISC_FEATURE
<222> LOCATION: (1)..(300)
<223> OTHER INFORMATION: From at least one, two, three, or four
      cysteines are included in the sequence
<220> FEATURE:
<221> NAME/KEY: MISC_FEATURE
<222> LOCATION: (10)..(10)
<223> OTHER INFORMATION: X is either T or C
<220> FEATURE:
<221> NAME/KEY: MISC_FEATURE
<222> LOCATION: (32)..(32)
<223> OTHER INFORMATION: X is either N or C
<220> FEATURE:
<221> NAME/KEY: MISC_FEATURE
<222> LOCATION: (118)..(118)
<223> OTHER INFORMATION: X is either N or C
<220> FEATURE:
<221> NAME/KEY: MISC_FEATURE
<222> LOCATION: (141)..(141)
<223> OTHER INFORMATION: X is either S or C
<220> FEATURE:
<221> NAME/KEY: MISC_FEATURE
<222> LOCATION: (291)..(300)
<223> OTHER INFORMATION: One or more amino acids in the C-terminus are
      optional

<400> SEQUENCE: 5

Met Ala Thr Ala Glu Thr Ser Thr Gly Xaa Lys Val Val Leu Gly Gln
1               5                   10                  15

Asn Gln Tyr Gly Lys Ala Glu Val Arg Leu Val Lys Val Thr Arg Xaa
            20                  25                  30
```

```
Thr Ala Arg His Glu Ile Gln Asp Leu Asn Val Thr Ser Gln Leu Ser
        35                  40                  45

Gly Asp Phe Glu Ala Ala His Thr Ala Gly Asp Asn Ala His Val Val
 50                  55                  60

Ala Thr Asp Thr Gln Lys Asn Thr Val Tyr Ala Phe Ala Arg Asp Gly
 65                  70                  75                  80

Phe Ala Thr Thr Glu Glu Phe Leu Leu Arg Leu Gly Lys His Phe Thr
                 85                  90                  95

Glu Gly Phe Asp Trp Val Thr Gly Gly Arg Trp Ala Ala Gln Gln Phe
                100                 105                 110

Phe Trp Asp Arg Ile Xaa Asp His Asp His Ala Phe Ser Arg Asn Lys
                115                 120                 125

Ser Glu Val Arg Thr Ala Val Leu Glu Ile Ser Gly Xaa Glu Gln Ala
130                 135                 140

Ile Val Ala Gly Ile Glu Gly Leu Thr Val Leu Lys Ser Thr Gly Ser
145                 150                 155                 160

Glu Phe His Gly Phe Pro Arg Asp Lys Tyr Thr Thr Leu Gln Glu Thr
                165                 170                 175

Thr Asp Arg Ile Leu Ala Thr Asp Val Ser Ala Arg Trp Arg Tyr Asn
                180                 185                 190

Thr Val Glu Val Asp Phe Asp Ala Val Tyr Ala Ser Val Arg Gly Leu
                195                 200                 205

Leu Leu Lys Ala Phe Ala Glu Thr His Ser Leu Ala Leu Gln Gln Thr
            210                 215                 220

Met Tyr Glu Met Gly Arg Ala Val Ile Glu Thr His Pro Glu Ile Asp
225                 230                 235                 240

Glu Ile Lys Met Ser Leu Pro Asn Lys His His Phe Leu Val Asp Leu
                245                 250                 255

Gln Pro Phe Gly Gln Asp Asn Pro Asn Glu Val Phe Tyr Ala Ala Asp
                260                 265                 270

Arg Pro Tyr Gly Leu Ile Glu Ala Thr Ile Gln Arg Glu Gly Ser Arg
            275                 280                 285

Ala Asp His Pro Ile Trp Ser Asn Ile Ala Gly Phe
        290                 295                 300

<210> SEQ ID NO 6
<211> LENGTH: 292
<212> TYPE: PRT
<213> ORGANISM: Artificial Sequence
<220> FEATURE:
<223> OTHER INFORMATION: Genus sequence, with truncated N-terminus, 4
      possible cysteines, SGD, optionally with or without C-terminal
      truncation
<220> FEATURE:
<221> NAME/KEY: MISC_FEATURE
<222> LOCATION: (1)..(292)
<223> OTHER INFORMATION: From at least one, two, three, or four
      cysteines are included in the sequence
<220> FEATURE:
<221> NAME/KEY: MISC_FEATURE
<222> LOCATION: (2)..(2)
<223> OTHER INFORMATION: X is either T or C
<220> FEATURE:
<221> NAME/KEY: MISC_FEATURE
<222> LOCATION: (24)..(24)
<223> OTHER INFORMATION: X is either N or C
<220> FEATURE:
<221> NAME/KEY: MISC_FEATURE
<222> LOCATION: (110)..(110)
<223> OTHER INFORMATION: X is either N or C
<220> FEATURE:
```

<220> FEATURE:
<221> NAME/KEY: MISC_FEATURE
<222> LOCATION: (133)..(133)
<223> OTHER INFORMATION: X is either S or C
<220> FEATURE:
<221> NAME/KEY: MISC_FEATURE
<222> LOCATION: (283)..(292)
<223> OTHER INFORMATION: One or more amino acids in the C-terminus are optional

<400> SEQUENCE: 6

```
Met Xaa Lys Val Val Leu Gly Gln Asn Gln Tyr Gly Lys Ala Glu Val
1               5                   10                  15

Arg Leu Val Lys Val Thr Arg Xaa Thr Ala Arg His Glu Ile Gln Asp
            20                  25                  30

Leu Asn Val Thr Ser Gln Leu Ser Gly Asp Phe Glu Ala Ala His Thr
        35                  40                  45

Ala Gly Asp Asn Ala His Val Val Ala Thr Asp Thr Gln Lys Asn Thr
    50                  55                  60

Val Tyr Ala Phe Ala Arg Asp Gly Phe Ala Thr Thr Glu Glu Phe Leu
65                  70                  75                  80

Leu Arg Leu Gly Lys His Phe Thr Glu Gly Phe Asp Trp Val Thr Gly
                85                  90                  95

Gly Arg Trp Ala Ala Gln Gln Phe Phe Trp Asp Arg Ile Xaa Asp His
            100                 105                 110

Asp His Ala Phe Ser Arg Asn Lys Ser Glu Val Arg Thr Ala Val Leu
        115                 120                 125

Glu Ile Ser Gly Xaa Glu Gln Ala Ile Val Ala Gly Ile Glu Gly Leu
    130                 135                 140

Thr Val Leu Lys Ser Thr Gly Ser Glu Phe His Gly Phe Pro Arg Asp
145                 150                 155                 160

Lys Tyr Thr Thr Leu Gln Glu Thr Thr Asp Arg Ile Leu Ala Thr Asp
                165                 170                 175

Val Ser Ala Arg Trp Arg Tyr Asn Thr Val Glu Val Asp Phe Asp Ala
            180                 185                 190

Val Tyr Ala Ser Val Arg Gly Leu Leu Leu Lys Ala Phe Ala Glu Thr
        195                 200                 205

His Ser Leu Ala Leu Gln Gln Thr Met Tyr Glu Met Gly Arg Ala Val
    210                 215                 220

Ile Glu Thr His Pro Glu Ile Asp Glu Ile Lys Met Ser Leu Pro Asn
225                 230                 235                 240

Lys His His Phe Leu Val Asp Leu Gln Pro Phe Gly Gln Asp Asn Pro
                245                 250                 255

Asn Glu Val Phe Tyr Ala Ala Asp Arg Pro Tyr Gly Leu Ile Glu Ala
            260                 265                 270

Thr Ile Gln Arg Glu Gly Ser Arg Ala Asp His Pro Ile Trp Ser Asn
        275                 280                 285

Ile Ala Gly Phe
    290
```

<210> SEQ ID NO 7
<211> LENGTH: 301
<212> TYPE: PRT
<213> ORGANISM: Artificial Sequence
<220> FEATURE:
<223> OTHER INFORMATION: Genus sequence, with optional N-terminal modification, 9 possible cysteines, R/SGD, optionally with or without C-terminal truncation
<220> FEATURE:

```
<221> NAME/KEY: MISC_FEATURE
<222> LOCATION: (1)..(301)
<223> OTHER INFORMATION: From at least one, two, three, or four
      cysteines are included in the sequence
<220> FEATURE:
<221> NAME/KEY: MISC_FEATURE
<222> LOCATION: (2)..(2)
<223> OTHER INFORMATION: X is either present or absent, and if present
      is T
<220> FEATURE:
<221> NAME/KEY: MISC_FEATURE
<222> LOCATION: (11)..(11)
<223> OTHER INFORMATION: X is either T or C
<220> FEATURE:
<221> NAME/KEY: MISC_FEATURE
<222> LOCATION: (33)..(33)
<223> OTHER INFORMATION: X is either N or C
<220> FEATURE:
<221> NAME/KEY: MISC_FEATURE
<222> LOCATION: (49)..(49)
<223> OTHER INFORMATION: X is either R or S
<220> FEATURE:
<221> NAME/KEY: MISC_FEATURE
<222> LOCATION: (119)..(119)
<223> OTHER INFORMATION: X is either N or C
<220> FEATURE:
<221> NAME/KEY: MISC_FEATURE
<222> LOCATION: (120)..(120)
<223> OTHER INFORMATION: X is either D or C
<220> FEATURE:
<221> NAME/KEY: MISC_FEATURE
<222> LOCATION: (142)..(142)
<223> OTHER INFORMATION: X is either S or C
<220> FEATURE:
<221> NAME/KEY: MISC_FEATURE
<222> LOCATION: (196)..(196)
<223> OTHER INFORMATION: X is either E or C
<220> FEATURE:
<221> NAME/KEY: MISC_FEATURE
<222> LOCATION: (238)..(238)
<223> OTHER INFORMATION: X is either P or C
<220> FEATURE:
<221> NAME/KEY: MISC_FEATURE
<222> LOCATION: (286)..(286)
<223> OTHER INFORMATION: X is either E or C
<220> FEATURE:
<221> NAME/KEY: MISC_FEATURE
<222> LOCATION: (289)..(289)
<223> OTHER INFORMATION: X is either R or C
<220> FEATURE:
<221> NAME/KEY: MISC_FEATURE
<222> LOCATION: (292)..(301)
<223> OTHER INFORMATION: One or more amino acids in the C-terminus are
      optional

<400> SEQUENCE: 7

Met Xaa Ala Thr Ala Glu Thr Ser Thr Gly Xaa Lys Val Val Leu Gly
1               5                   10                  15

Gln Asn Gln Tyr Gly Lys Ala Glu Val Arg Leu Val Lys Val Thr Arg
                20                  25                  30

Xaa Thr Ala Arg His Glu Ile Gln Asp Leu Asn Val Thr Ser Gln Leu
            35                  40                  45

Xaa Gly Asp Phe Glu Ala Ala His Thr Ala Gly Asp Asn Ala His Val
        50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
                100                 105                 110

Phe Phe Trp Asp Arg Ile Xaa Xaa His Asp His Ala Phe Ser Arg Asn
```

```
              115                 120                 125
Lys Ser Glu Val Arg Thr Ala Val Leu Glu Ile Ser Gly Xaa Glu Gln
130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Xaa Val Asp Phe Asp Ala Val Tyr Ala Ser Val Arg Gly
                195                 200                 205

Leu Leu Leu Lys Ala Phe Ala Glu Thr His Ser Leu Ala Leu Gln Gln
210                 215                 220

Thr Met Tyr Glu Met Gly Arg Ala Val Ile Glu Thr His Xaa Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Xaa Gly Ser
                275                 280                 285

Xaa Ala Asp His Pro Ile Trp Ser Asn Ile Ala Gly Phe
            290                 295                 300

<210> SEQ ID NO 8
<211> LENGTH: 301
<212> TYPE: PRT
<213> ORGANISM: Artificial Sequence
<220> FEATURE:
<223> OTHER INFORMATION: Genus sequence, with optional N-terminal
      modification, 9 possible cysteines, XGD, optionally with or
      without C-terminal truncation
<220> FEATURE:
<221> NAME/KEY: MISC_FEATURE
<222> LOCATION: (1)..(301)
<223> OTHER INFORMATION: From at least one, two, three, or four
      cysteines are included in the sequence
<220> FEATURE:
<221> NAME/KEY: MISC_FEATURE
<222> LOCATION: (2)..(2)
<223> OTHER INFORMATION: X is either present or absent, and if present
      is T
<220> FEATURE:
<221> NAME/KEY: MISC_FEATURE
<222> LOCATION: (11)..(11)
<223> OTHER INFORMATION: X is either T or C
<220> FEATURE:
<221> NAME/KEY: MISC_FEATURE
<222> LOCATION: (33)..(33)
<223> OTHER INFORMATION: X is either N or C
<220> FEATURE:
<221> NAME/KEY: MISC_FEATURE
<222> LOCATION: (49)..(49)
<223> OTHER INFORMATION: X is any naturally occurring amino acid except
      C
<220> FEATURE:
<221> NAME/KEY: MISC_FEATURE
<222> LOCATION: (119)..(119)
<223> OTHER INFORMATION: X is either N or C
<220> FEATURE:
<221> NAME/KEY: MISC_FEATURE
<222> LOCATION: (120)..(120)
<223> OTHER INFORMATION: X is either D or C
<220> FEATURE:
<221> NAME/KEY: MISC_FEATURE
<222> LOCATION: (142)..(142)
<223> OTHER INFORMATION: X is either S or C
```

```
<220> FEATURE:
<221> NAME/KEY: MISC_FEATURE
<222> LOCATION: (196)..(196)
<223> OTHER INFORMATION: X is either E or C
<220> FEATURE:
<221> NAME/KEY: MISC_FEATURE
<222> LOCATION: (238)..(238)
<223> OTHER INFORMATION: X is either P or C
<220> FEATURE:
<221> NAME/KEY: MISC_FEATURE
<222> LOCATION: (286)..(286)
<223> OTHER INFORMATION: X is either E or C
<220> FEATURE:
<221> NAME/KEY: MISC_FEATURE
<222> LOCATION: (289)..(289)
<223> OTHER INFORMATION: X is either R or C
<220> FEATURE:
<221> NAME/KEY: MISC_FEATURE
<222> LOCATION: (292)..(301)
<223> OTHER INFORMATION: One or more amino acids in the C-terminus are
      optional

<400> SEQUENCE: 8

Met Xaa Ala Thr Ala Glu Thr Ser Thr Gly Xaa Lys Val Val Leu Gly
1               5                   10                  15

Gln Asn Gln Tyr Gly Lys Ala Glu Val Arg Leu Val Lys Val Thr Arg
            20                  25                  30

Xaa Thr Ala Arg His Glu Ile Gln Asp Leu Asn Val Thr Ser Gln Leu
        35                  40                  45

Xaa Gly Asp Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Phe Trp Asp Arg Ile Xaa Xaa His Asp His Ala Phe Ser Arg Asn
        115                 120                 125

Lys Ser Glu Val Arg Thr Ala Val Leu Glu Ile Ser Gly Xaa Glu Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Xaa Val Asp Phe Asp Ala Val Tyr Ala Ser Val Arg Gly
        195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Xaa Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Xaa Gly Ser
        275                 280                 285

Xaa Ala Asp His Pro Ile Trp Ser Asn Ile Ala Gly Phe
```

-continued

```
                290                 295                 300
```

<210> SEQ ID NO 9
<211> LENGTH: 292
<212> TYPE: PRT
<213> ORGANISM: Artificial Sequence
<220> FEATURE:
<223> OTHER INFORMATION: Genus sequence, with N-terminal truncation, 9
      possible cysteines, XGD, optionally with or without C-terminal
      truncation
<220> FEATURE:
<221> NAME/KEY: MISC_FEATURE
<222> LOCATION: (1)..(292)
<223> OTHER INFORMATION: From at least one, two, three, or four
      cysteines are included in the sequence
<220> FEATURE:
<221> NAME/KEY: MISC_FEATURE
<222> LOCATION: (2)..(2)
<223> OTHER INFORMATION: X is either T or C
<220> FEATURE:
<221> NAME/KEY: MISC_FEATURE
<222> LOCATION: (24)..(24)
<223> OTHER INFORMATION: X is either N or C
<220> FEATURE:
<221> NAME/KEY: MISC_FEATURE
<222> LOCATION: (40)..(40)
<223> OTHER INFORMATION: X is any naturally occurring amino acid except
      C
<220> FEATURE:
<221> NAME/KEY: MISC_FEATURE
<222> LOCATION: (110)..(110)
<223> OTHER INFORMATION: X is either N or C
<220> FEATURE:
<221> NAME/KEY: MISC_FEATURE
<222> LOCATION: (111)..(111)
<223> OTHER INFORMATION: X is either D or C
<220> FEATURE:
<221> NAME/KEY: MISC_FEATURE
<222> LOCATION: (133)..(133)
<223> OTHER INFORMATION: X is either S or C
<220> FEATURE:
<221> NAME/KEY: MISC_FEATURE
<222> LOCATION: (187)..(187)
<223> OTHER INFORMATION: X is either E or C
<220> FEATURE:
<221> NAME/KEY: MISC_FEATURE
<222> LOCATION: (229)..(229)
<223> OTHER INFORMATION: X is either P or C
<220> FEATURE:
<221> NAME/KEY: MISC_FEATURE
<222> LOCATION: (277)..(277)
<223> OTHER INFORMATION: X is either E or C
<220> FEATURE:
<221> NAME/KEY: MISC_FEATURE
<222> LOCATION: (280)..(280)
<223> OTHER INFORMATION: X is either R or C
<220> FEATURE:
<221> NAME/KEY: MISC_FEATURE
<222> LOCATION: (283)..(292)
<223> OTHER INFORMATION: One or more amino acids in the C-terminus are
      optional

<400> SEQUENCE: 9

```
Met Xaa Lys Val Val Leu Gly Gln Asn Gln Tyr Gly Lys Ala Glu Val
1               5                   10                  15

Arg Leu Val Lys Val Thr Arg Xaa Thr Ala Arg His Glu Ile Gln Asp
            20                  25                  30

Leu Asn Val Thr Ser Gln Leu Xaa Gly Asp Phe Glu Ala Ala His Thr
        35                  40                  45

Ala Gly Asp Asn Ala His Val Val Ala Thr Thr Gln Lys Asn Thr
    50                  55                  60

Val Tyr Ala Phe Ala Arg Asp Gly Phe Ala Thr Thr Glu Glu Phe Leu
65                  70                  75                  80
```

```
Leu Arg Leu Gly Lys His Phe Thr Glu Gly Phe Asp Trp Val Thr Gly
                85                  90                  95

Gly Arg Trp Ala Ala Gln Gln Phe Phe Trp Asp Arg Ile Xaa Xaa His
            100                 105                 110

Asp His Ala Phe Ser Arg Asn Lys Ser Glu Val Arg Thr Ala Val Leu
        115                 120                 125

Glu Ile Ser Gly Xaa Glu Gln Ala Ile Val Ala Gly Ile Glu Gly Leu
    130                 135                 140

Thr Val Leu Lys Ser Thr Gly Ser Glu Phe His Gly Phe Pro Arg Asp
145                 150                 155                 160

Lys Tyr Thr Thr Leu Gln Glu Thr Asp Arg Ile Leu Ala Thr Asp
                165                 170                 175

Val Ser Ala Arg Trp Arg Tyr Asn Thr Val Xaa Val Asp Phe Asp Ala
            180                 185                 190

Val Tyr Ala Ser Val Arg Gly Leu Leu Lys Ala Phe Ala Glu Thr
        195                 200                 205

His Ser Leu Ala Leu Gln Gln Thr Met Tyr Glu Met Gly Arg Ala Val
    210                 215                 220

Ile Glu Thr His Xaa Glu Ile Asp Glu Ile Lys Met Ser Leu Pro Asn
225                 230                 235                 240

Lys His His Phe Leu Val Asp Leu Gln Pro Phe Gly Gln Asp Asn Pro
                245                 250                 255

Asn Glu Val Phe Tyr Ala Ala Asp Arg Pro Tyr Gly Leu Ile Glu Ala
            260                 265                 270

Thr Ile Gln Arg Xaa Gly Ser Xaa Ala Asp His Pro Ile Trp Ser Asn
        275                 280                 285

Ile Ala Gly Phe
    290

<210> SEQ ID NO 10
<211> LENGTH: 301
<212> TYPE: PRT
<213> ORGANISM: Artificial Sequence
<220> FEATURE:
<223> OTHER INFORMATION: Genus sequence, with optional N-terminal
      modification, 9 possible conjugation sites, XGD, optionally with
      or without C-terminal truncation
<220> FEATURE:
<221> NAME/KEY: MISC_FEATURE
<222> LOCATION: (1)..(301)
<223> OTHER INFORMATION: From at least one, two, three, or four
      cysteines are included in the sequence
<220> FEATURE:
<221> NAME/KEY: MISC_FEATURE
<222> LOCATION: (2)..(2)
<223> OTHER INFORMATION: X is either present or absent, and if present
      is T
<220> FEATURE:
<221> NAME/KEY: MISC_FEATURE
<222> LOCATION: (11)..(11)
<223> OTHER INFORMATION: X is either T or any natural or unnatural amino
      acid used for site-specific conjugation
<220> FEATURE:
<221> NAME/KEY: MISC_FEATURE
<222> LOCATION: (33)..(33)
<223> OTHER INFORMATION: X is either N or any natural or unnatural amino
      acid used for site-specific conjugation
<220> FEATURE:
<221> NAME/KEY: MISC_FEATURE
<222> LOCATION: (49)..(49)
<223> OTHER INFORMATION: X is any naturally occurring amino acid except
      C
<220> FEATURE:
<221> NAME/KEY: MISC_FEATURE
```

```
<222> LOCATION: (119)..(119)
<223> OTHER INFORMATION: X is either N or any natural or unnatural amino
      acid used for site-specific conjugation
<220> FEATURE:
<221> NAME/KEY: MISC_FEATURE
<222> LOCATION: (120)..(120)
<223> OTHER INFORMATION: X is either D or any natural or unnatural amino
      acid used for site-specific conjugation
<220> FEATURE:
<221> NAME/KEY: MISC_FEATURE
<222> LOCATION: (142)..(142)
<223> OTHER INFORMATION: X is either S or any natural or unnatural amino
      acid used for site-specific conjugation
<220> FEATURE:
<221> NAME/KEY: MISC_FEATURE
<222> LOCATION: (196)..(196)
<223> OTHER INFORMATION: X is either E or any natural or unnatural amino
      acid used for site-specific conjugation
<220> FEATURE:
<221> NAME/KEY: MISC_FEATURE
<222> LOCATION: (238)..(238)
<223> OTHER INFORMATION: X is either P or any natural or unnatural amino
      acid used for site-specific conjugation
<220> FEATURE:
<221> NAME/KEY: MISC_FEATURE
<222> LOCATION: (286)..(286)
<223> OTHER INFORMATION: X is either E or any natural or unnatural amino
      acid used for site-specific conjugation
<220> FEATURE:
<221> NAME/KEY: MISC_FEATURE
<222> LOCATION: (289)..(289)
<223> OTHER INFORMATION: X is either R or any natural or unnatural amino
      acid used for site-specific conjugation
<220> FEATURE:
<221> NAME/KEY: MISC_FEATURE
<222> LOCATION: (292)..(301)
<223> OTHER INFORMATION: One or more amino acids in the C-terminus are
      optional

<400> SEQUENCE: 10

Met Xaa Ala Thr Ala Glu Thr Ser Thr Gly Xaa Lys Val Val Leu Gly
1               5                   10                  15

Gln Asn Gln Tyr Gly Lys Ala Glu Val Arg Leu Val Lys Val Thr Arg
            20                  25                  30

Xaa Thr Ala Arg His Glu Ile Gln Asp Leu Asn Val Thr Ser Gln Leu
        35                  40                  45

Xaa Gly Asp Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Phe Trp Asp Arg Ile Xaa Xaa His Asp His Ala Phe Ser Arg Asn
        115                 120                 125

Lys Ser Glu Val Arg Thr Ala Val Leu Glu Ile Ser Gly Xaa Glu Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Xaa Val Asp Phe Asp Ala Val Tyr Ala Ser Val Arg Gly
        195                 200                 205
```

```
Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Xaa Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Xaa Gly Ser
        275                 280                 285

Xaa Ala Asp His Pro Ile Trp Ser Asn Ile Ala Gly Phe
    290                 295                 300

<210> SEQ ID NO 11
<211> LENGTH: 292
<212> TYPE: PRT
<213> ORGANISM: Artificial Sequence
<220> FEATURE:
<223> OTHER INFORMATION: Genus sequence, with N-terminal truncation, 9
      possible conjugation sites, XGD, optionally with or without
      C-terminal truncation
<220> FEATURE:
<221> NAME/KEY: MISC_FEATURE
<222> LOCATION: (1)..(292)
<223> OTHER INFORMATION: From at least one, two, three, or four
      cysteines are included in the sequence
<220> FEATURE:
<221> NAME/KEY: MISC_FEATURE
<222> LOCATION: (2)..(2)
<223> OTHER INFORMATION: X is either T or any natural or unnatural amino
      acid used for site-specific conjugation
<220> FEATURE:
<221> NAME/KEY: MISC_FEATURE
<222> LOCATION: (24)..(24)
<223> OTHER INFORMATION: X is either N or any natural or unnatural amino
      acid used for site-specific conjugation
<220> FEATURE:
<221> NAME/KEY: MISC_FEATURE
<222> LOCATION: (40)..(40)
<223> OTHER INFORMATION: X is any naturally occurring amino acid except
      C
<220> FEATURE:
<221> NAME/KEY: MISC_FEATURE
<222> LOCATION: (110)..(110)
<223> OTHER INFORMATION: X is either N or any natural or unnatural amino
      acid used for site-specific conjugation
<220> FEATURE:
<221> NAME/KEY: MISC_FEATURE
<222> LOCATION: (111)..(111)
<223> OTHER INFORMATION: X is either D or any natural or unnatural amino
      acid used for site-specific conjugation
<220> FEATURE:
<221> NAME/KEY: MISC_FEATURE
<222> LOCATION: (133)..(133)
<223> OTHER INFORMATION: X is either S or any natural or unnatural amino
      acid used for site-specific conjugation
<220> FEATURE:
<221> NAME/KEY: MISC_FEATURE
<222> LOCATION: (187)..(187)
<223> OTHER INFORMATION: X is either E or any natural or unnatural amino
      acid used for site-specific conjugation
<220> FEATURE:
<221> NAME/KEY: MISC_FEATURE
<222> LOCATION: (229)..(229)
<223> OTHER INFORMATION: X is either P or any natural or unnatural amino
      acid used for site-specific conjugation
<220> FEATURE:
<221> NAME/KEY: MISC_FEATURE
<222> LOCATION: (277)..(277)
<223> OTHER INFORMATION: X is either E or any natural or unnatural amino
      acid used for site-specific conjugation
<220> FEATURE:
```

```
<221> NAME/KEY: MISC_FEATURE
<222> LOCATION: (280)..(280)
<223> OTHER INFORMATION: X is either R or any natural or unnatural amino
      acid used for site-specific conjugation
<220> FEATURE:
<221> NAME/KEY: MISC_FEATURE
<222> LOCATION: (283)..(292)
<223> OTHER INFORMATION: One or more amino acids in the C-terminus are
      optional

<400> SEQUENCE: 11
```

| | | | | | | | | | | | | | | |
|---|---|---|---|---|---|---|---|---|---|---|---|---|---|---|
| Met | Xaa | Lys | Val | Val | Leu | Gly | Gln | Asn | Gln | Tyr | Gly | Lys | Ala | Glu | Val |
| 1 | | | | 5 | | | | | 10 | | | | | 15 | |
| Arg | Leu | Val | Lys | Val | Thr | Arg | Xaa | Thr | Ala | Arg | His | Glu | Ile | Gln | Asp |
| | | 20 | | | | | 25 | | | | | 30 | | | |
| Leu | Asn | Val | Thr | Ser | Gln | Leu | Xaa | Gly | Asp | Phe | Glu | Ala | Ala | His | Thr |
| | | | 35 | | | | | 40 | | | | | 45 | | |
| Ala | Gly | Asp | Asn | Ala | His | Val | Val | Ala | Thr | Asp | Thr | Gln | Lys | Asn | Thr |
| | 50 | | | | | 55 | | | | | 60 | | | | |
| Val | Tyr | Ala | Phe | Ala | Arg | Asp | Gly | Phe | Ala | Thr | Thr | Glu | Glu | Phe | Leu |
| 65 | | | | | 70 | | | | | 75 | | | | | 80 |
| Leu | Arg | Leu | Gly | Lys | His | Phe | Thr | Glu | Gly | Phe | Asp | Trp | Val | Thr | Gly |
| | | | | 85 | | | | | 90 | | | | | 95 | |
| Gly | Arg | Trp | Ala | Ala | Gln | Gln | Phe | Phe | Trp | Asp | Arg | Ile | Xaa | Xaa | His |
| | | | 100 | | | | | 105 | | | | | 110 | | |
| Asp | His | Ala | Phe | Ser | Arg | Asn | Lys | Ser | Glu | Val | Arg | Thr | Ala | Val | Leu |
| | | 115 | | | | | 120 | | | | | 125 | | | |
| Glu | Ile | Ser | Gly | Xaa | Glu | Gln | Ala | Ile | Val | Ala | Gly | Ile | Glu | Gly | Leu |
| | 130 | | | | | 135 | | | | | 140 | | | | |
| Thr | Val | Leu | Lys | Ser | Thr | Gly | Ser | Glu | Phe | His | Gly | Phe | Pro | Arg | Asp |
| 145 | | | | | 150 | | | | | 155 | | | | | 160 |
| Lys | Tyr | Thr | Thr | Leu | Gln | Glu | Thr | Thr | Asp | Arg | Ile | Leu | Ala | Thr | Asp |
| | | | | 165 | | | | | 170 | | | | | 175 | |
| Val | Ser | Ala | Arg | Trp | Arg | Tyr | Asn | Thr | Val | Xaa | Val | Asp | Phe | Asp | Ala |
| | | | 180 | | | | | 185 | | | | | 190 | | |
| Val | Tyr | Ala | Ser | Val | Arg | Gly | Leu | Leu | Leu | Lys | Ala | Phe | Ala | Glu | Thr |
| | | 195 | | | | | 200 | | | | | 205 | | | |
| His | Ser | Leu | Ala | Leu | Gln | Gln | Thr | Met | Tyr | Glu | Met | Gly | Arg | Ala | Val |
| | 210 | | | | | 215 | | | | | 220 | | | | |
| Ile | Glu | Thr | His | Xaa | Glu | Ile | Asp | Glu | Ile | Lys | Met | Ser | Leu | Pro | Asn |
| 225 | | | | | 230 | | | | | 235 | | | | | 240 |
| Lys | His | His | Phe | Leu | Val | Asp | Leu | Gln | Pro | Phe | Gly | Gln | Asp | Asn | Pro |
| | | | | 245 | | | | | 250 | | | | | 255 | |
| Asn | Glu | Val | Phe | Tyr | Ala | Ala | Asp | Arg | Pro | Tyr | Gly | Leu | Ile | Glu | Ala |
| | | | 260 | | | | | 265 | | | | | 270 | | |
| Thr | Ile | Gln | Arg | Xaa | Gly | Ser | Xaa | Ala | Asp | His | Pro | Ile | Trp | Ser | Asn |
| | | 275 | | | | | 280 | | | | | 285 | | | |
| Ile | Ala | Gly | Phe |
| | 290 | | |

```
<210> SEQ ID NO 12
<211> LENGTH: 303
<212> TYPE: PRT
<213> ORGANISM: Artificial Sequence
<220> FEATURE:
<223> OTHER INFORMATION: Modified Arthrobacter globiformis Uricase C1
      construct (T11C mutation, SGD, optional N-terminal His tag and
      optional short linker (first Uricase residue corresponds to Thr2))
<220> FEATURE:
```

<220> FEATURE:
<221> NAME/KEY: MISC_FEATURE
<222> LOCATION: (1)..(13)
<223> OTHER INFORMATION: Optional N-terminal His tag and optional linker

<400> SEQUENCE: 12

```
Met Gly Ser His His His His His Gly Ala Arg Gln Thr Ala Thr
1               5                   10                  15

Ala Glu Thr Ser Thr Gly Cys Lys Val Val Leu Gly Gln Asn Gln Tyr
            20                  25                  30

Gly Lys Ala Glu Val Arg Leu Val Lys Val Thr Arg Asn Thr Ala Arg
        35                  40                  45

His Glu Ile Gln Asp Leu Asn Val Thr Ser Gln Leu Ser Gly Asp Phe
50                  55                  60

Glu Ala Ala His Thr Ala Gly Asp Asn Ala His Val Val Ala Thr Asp
65                  70                  75                  80

Thr Gln Lys Asn Thr Val Tyr Ala Phe Ala Arg Asp Gly Phe Ala Thr
                85                  90                  95

Thr Glu Glu Phe Leu Leu Arg Leu Gly Lys His Phe Thr Glu Gly Phe
            100                 105                 110

Asp Trp Val Thr Gly Gly Arg Trp Ala Ala Gln Gln Phe Phe Trp Asp
        115                 120                 125

Arg Ile Asn Asp His Asp His Ala Phe Ser Arg Asn Lys Ser Glu Val
130                 135                 140

Arg Thr Ala Val Leu Glu Ile Ser Gly Ser Glu Gln Ala Ile Val Ala
145                 150                 155                 160

Gly Ile Glu Gly Leu Thr Val Leu Lys Ser Thr Gly Ser Glu Phe His
                165                 170                 175

Gly Phe Pro Arg Asp Lys Tyr Thr Thr Leu Gln Glu Thr Thr Asp Arg
            180                 185                 190

Ile Leu Ala Thr Asp Val Ser Ala Arg Trp Arg Tyr Asn Thr Val Glu
        195                 200                 205

Val Asp Phe Asp Ala Val Tyr Ala Ser Val Arg Gly Leu Leu Leu Lys
    210                 215                 220

Ala Phe Ala Glu Thr His Ser Leu Ala Leu Gln Gln Thr Met Tyr Glu
225                 230                 235                 240

Met Gly Arg Ala Val Ile Glu Thr His Pro Glu Ile Asp Glu Ile Lys
                245                 250                 255

Met Ser Leu Pro Asn Lys His His Phe Leu Val Asp Leu Gln Pro Phe
            260                 265                 270

Gly Gln Asp Asn Pro Asn Glu Val Phe Tyr Ala Ala Asp Arg Pro Tyr
        275                 280                 285

Gly Leu Ile Glu Ala Thr Ile Gln Arg Glu Gly Ser Arg Ala Asp
    290                 295                 300
```

<210> SEQ ID NO 13
<211> LENGTH: 290
<212> TYPE: PRT
<213> ORGANISM: Artificial Sequence
<220> FEATURE:
<223> OTHER INFORMATION: Modified Arthrobacter globiformis Uricase C1 construct (variant 1), with tag eliminated, deletion of Thr2 (to avoid partial N-term Met cleavage) and Cys at position 11

<400> SEQUENCE: 13

```
Met Ala Thr Ala Glu Thr Ser Thr Gly Cys Lys Val Val Leu Gly Gln
1               5                   10                  15

Asn Gln Tyr Gly Lys Ala Glu Val Arg Leu Val Lys Val Thr Arg Asn
```

```
              20                  25                  30
Thr Ala Arg His Glu Ile Gln Asp Leu Asn Val Thr Ser Gln Leu Ser
         35                  40                  45
Gly Asp Phe Glu Ala Ala His Thr Ala Gly Asp Asn Ala His Val Val
 50                  55                  60
Ala Thr Asp Thr Gln Lys Asn Thr Val Tyr Ala Phe Ala Arg Asp Gly
 65                  70                  75                  80
Phe Ala Thr Thr Glu Glu Phe Leu Leu Arg Leu Gly Lys His Phe Thr
                 85                  90                  95
Glu Gly Phe Asp Trp Val Thr Gly Arg Trp Ala Ala Gln Gln Phe
            100                 105                 110
Phe Trp Asp Arg Ile Asn Asp His Asp His Ala Phe Ser Arg Asn Lys
            115                 120                 125
Ser Glu Val Arg Thr Ala Val Leu Glu Ile Ser Gly Ser Glu Gln Ala
        130                 135                 140
Ile Val Ala Gly Ile Glu Gly Leu Thr Val Leu Lys Ser Thr Gly Ser
145                 150                 155                 160
Glu Phe His Gly Phe Pro Arg Asp Lys Tyr Thr Thr Leu Gln Glu Thr
                165                 170                 175
Thr Asp Arg Ile Leu Ala Thr Asp Val Ser Ala Arg Trp Arg Tyr Asn
            180                 185                 190
Thr Val Glu Val Asp Phe Asp Ala Val Tyr Ala Ser Val Arg Gly Leu
        195                 200                 205
Leu Leu Lys Ala Phe Ala Glu Thr His Ser Leu Ala Leu Gln Gln Thr
    210                 215                 220
Met Tyr Glu Met Gly Arg Ala Val Ile Glu Thr His Pro Glu Ile Asp
225                 230                 235                 240
Glu Ile Lys Met Ser Leu Pro Asn Lys His His Phe Leu Val Asp Leu
                245                 250                 255
Gln Pro Phe Gly Gln Asp Asn Pro Asn Glu Val Phe Tyr Ala Ala Asp
            260                 265                 270
Arg Pro Tyr Gly Leu Ile Glu Ala Thr Ile Gln Arg Glu Gly Ser Arg
        275                 280                 285
Ala Asp
    290

<210> SEQ ID NO 14
<211> LENGTH: 287
<212> TYPE: PRT
<213> ORGANISM: Artificial Sequence
<220> FEATURE:
<223> OTHER INFORMATION: Modified Arthrobacter globiformis Uricase C1
      construct (variant 2 - N-term truncation) with tag eliminated,
      deletion of Thr2-Ala5 and Cys at position 11, expect complete
      retention of N-term Met

<400> SEQUENCE: 14

Met Glu Thr Ser Thr Gly Cys Lys Val Val Leu Gly Gln Asn Gln Tyr
  1               5                  10                  15
Gly Lys Ala Glu Val Arg Leu Val Lys Val Thr Arg Asn Thr Ala Arg
             20                  25                  30
His Glu Ile Gln Asp Leu Asn Val Thr Ser Gln Leu Ser Gly Asp Phe
         35                  40                  45
Glu Ala Ala His Thr Ala Gly Asp Asn Ala His Val Val Ala Thr Asp
 50                  55                  60
Thr Gln Lys Asn Thr Val Tyr Ala Phe Ala Arg Asp Gly Phe Ala Thr
```

```
                65                  70                  75                  80
Thr Glu Glu Phe Leu Leu Arg Leu Gly Lys His Phe Thr Glu Gly Phe
                    85                  90                  95

Asp Trp Val Thr Gly Gly Arg Trp Ala Ala Gln Gln Phe Phe Trp Asp
                100                 105                 110

Arg Ile Asn Asp His Asp His Ala Phe Ser Arg Asn Lys Ser Glu Val
                115                 120                 125

Arg Thr Ala Val Leu Glu Ile Ser Gly Ser Glu Gln Ala Ile Val Ala
            130                 135                 140

Gly Ile Glu Gly Leu Thr Val Leu Lys Ser Thr Gly Ser Glu Phe His
145                 150                 155                 160

Gly Phe Pro Arg Asp Lys Tyr Thr Thr Leu Gln Glu Thr Thr Asp Arg
                165                 170                 175

Ile Leu Ala Thr Asp Val Ser Ala Arg Trp Arg Tyr Asn Thr Val Glu
                180                 185                 190

Val Asp Phe Asp Ala Val Tyr Ala Ser Val Arg Gly Leu Leu Leu Lys
                195                 200                 205

Ala Phe Ala Glu Thr His Ser Leu Ala Leu Gln Gln Thr Met Tyr Glu
            210                 215                 220

Met Gly Arg Ala Val Ile Glu Thr His Pro Glu Ile Asp Glu Ile Lys
225                 230                 235                 240

Met Ser Leu Pro Asn Lys His His Phe Leu Val Asp Leu Gln Pro Phe
                245                 250                 255

Gly Gln Asp Asn Pro Asn Glu Val Phe Tyr Ala Ala Asp Arg Pro Tyr
                260                 265                 270

Gly Leu Ile Glu Ala Thr Ile Gln Arg Glu Gly Ser Arg Ala Asp
            275                 280                 285

<210> SEQ ID NO 15
<211> LENGTH: 283
<212> TYPE: PRT
<213> ORGANISM: Artificial Sequence
<220> FEATURE:
<223> OTHER INFORMATION: Modified Arthrobacter globiformis Uricase C1
      construct (variant 3 - N-term truncation) with tag eliminated,
      deletion of Thr2-Thr9, Cys at position 11, expect processing of
      N-term met

<400> SEQUENCE: 15

Met Gly Cys Lys Val Val Leu Gly Gln Asn Gln Tyr Gly Lys Ala Glu
1               5                   10                  15

Val Arg Leu Val Lys Val Thr Arg Asn Thr Ala Arg His Glu Ile Gln
                20                  25                  30

Asp Leu Asn Val Thr Ser Gln Leu Ser Gly Asp Phe Glu Ala Ala His
            35                  40                  45

Thr Ala Gly Asp Asn Ala His Val Val Ala Thr Asp Thr Gln Lys Asn
        50                  55                  60

Thr Val Tyr Ala Phe Ala Arg Asp Gly Phe Ala Thr Thr Glu Glu Phe
65                  70                  75                  80

Leu Leu Arg Leu Gly Lys His Phe Thr Glu Gly Phe Asp Trp Val Thr
                85                  90                  95

Gly Gly Arg Trp Ala Ala Gln Gln Phe Phe Trp Asp Arg Ile Asn Asp
                100                 105                 110

His Asp His Ala Phe Ser Arg Asn Lys Ser Glu Val Arg Thr Ala Val
            115                 120                 125

Leu Glu Ile Ser Gly Ser Glu Gln Ala Ile Val Ala Gly Ile Glu Gly
```

```
                  130             135             140
Leu Thr Val Leu Lys Ser Thr Gly Ser Glu Phe His Gly Phe Pro Arg
145                 150                 155                 160

Asp Lys Tyr Thr Thr Leu Gln Glu Thr Thr Asp Arg Ile Leu Ala Thr
                165                 170                 175

Asp Val Ser Ala Arg Trp Arg Tyr Asn Thr Val Glu Val Asp Phe Asp
            180                 185                 190

Ala Val Tyr Ala Ser Val Arg Gly Leu Leu Lys Ala Phe Ala Glu
                195                 200                 205

Thr His Ser Leu Ala Leu Gln Gln Thr Met Tyr Glu Met Gly Arg Ala
            210                 215                 220

Val Ile Glu Thr His Pro Glu Ile Asp Glu Ile Lys Met Ser Leu Pro
225                 230                 235                 240

Asn Lys His His Phe Leu Val Asp Leu Gln Pro Phe Gly Gln Asp Asn
                245                 250                 255

Pro Asn Glu Val Phe Tyr Ala Asp Arg Pro Tyr Gly Leu Ile Glu
                260                 265                 270

Ala Thr Ile Gln Arg Glu Gly Ser Arg Ala Asp
            275                 280
```

<210> SEQ ID NO 16
<211> LENGTH: 303
<212> TYPE: PRT
<213> ORGANISM: Artificial Sequence
<220> FEATURE:
<223> OTHER INFORMATION: Modified Arthrobacter globiformis Uricase with
      SGD, and PEGylation available sites at T11C, N33C, S142C, optional
      N-terminal His tag and optional short linker
<220> FEATURE:
<221> NAME/KEY: MISC_FEATURE
<222> LOCATION: (1)..(13)
<223> OTHER INFORMATION: Optional N-terminal His tag and optional linker

<400> SEQUENCE: 16

```
Met Gly Ser His His His His His Gly Ala Arg Gln Thr Ala Thr
1               5                   10                  15

Ala Glu Thr Ser Thr Gly Cys Lys Val Val Leu Gly Gln Asn Gln Tyr
                20                  25                  30

Gly Lys Ala Glu Val Arg Leu Val Lys Val Thr Arg Cys Thr Ala Arg
            35                  40                  45

His Glu Ile Gln Asp Leu Asn Val Thr Ser Gln Leu Ser Gly Asp Phe
        50                  55                  60

Glu Ala Ala His Thr Ala Gly Asp Asn Ala His Val Val Ala Thr Asp
65                  70                  75                  80

Thr Gln Lys Asn Thr Val Tyr Ala Phe Ala Arg Asp Gly Phe Ala Thr
                85                  90                  95

Thr Glu Glu Phe Leu Leu Arg Leu Gly Lys His Phe Thr Glu Gly Phe
                100                 105                 110

Asp Trp Val Thr Gly Gly Arg Trp Ala Ala Gln Phe Phe Trp Asp
            115                 120                 125

Arg Ile Asn Asp His Asp His Ala Phe Ser Arg Asn Lys Ser Glu Val
130                 135                 140

Arg Thr Ala Val Leu Glu Ile Ser Gly Cys Glu Gln Ala Ile Val Ala
145                 150                 155                 160

Gly Ile Glu Gly Leu Thr Val Leu Lys Ser Thr Gly Ser Glu Phe His
            165                 170                 175

Gly Phe Pro Arg Asp Lys Tyr Thr Thr Leu Gln Glu Thr Thr Asp Arg
```

```
                180                 185                 190
Ile Leu Ala Thr Asp Val Ser Ala Arg Trp Arg Tyr Asn Thr Val Glu
            195                 200                 205
Val Asp Phe Asp Ala Val Tyr Ala Ser Val Arg Gly Leu Leu Leu Lys
        210                 215                 220
Ala Phe Ala Glu Thr His Ser Leu Ala Leu Gln Gln Thr Met Tyr Glu
225                 230                 235                 240
Met Gly Arg Ala Val Ile Glu Thr His Pro Glu Ile Asp Glu Ile Lys
                245                 250                 255
Met Ser Leu Pro Asn Lys His His Phe Leu Val Asp Leu Gln Pro Phe
            260                 265                 270
Gly Gln Asp Asn Pro Asn Glu Val Phe Tyr Ala Ala Asp Arg Pro Tyr
        275                 280                 285
Gly Leu Ile Glu Ala Thr Ile Gln Arg Glu Gly Ser Arg Ala Asp
    290                 295                 300
```

<210> SEQ ID NO 17
<211> LENGTH: 303
<212> TYPE: PRT
<213> ORGANISM: Artificial Sequence
<220> FEATURE:
<223> OTHER INFORMATION: Modified Arthrobacter globiformis Uricase,
      NH2-terminal truncated, SGD, PEGylation available sites at T11C
      and N33C 2-Cys (SGD His C2) with optional N-terminal His tag and
      optional short linker
<220> FEATURE:
<221> NAME/KEY: MISC_FEATURE
<222> LOCATION: (1)..(13)
<223> OTHER INFORMATION: Optional N-terminal His tag and optional linker

<400> SEQUENCE: 17

```
Met Gly Ser His His His His His His Gly Ala Arg Gln Thr Ala Thr
1               5                   10                  15
Ala Glu Thr Ser Thr Gly Cys Lys Val Val Leu Gly Gln Asn Gln Tyr
            20                  25                  30
Gly Lys Ala Glu Val Arg Leu Val Lys Val Thr Arg Cys Thr Ala Arg
        35                  40                  45
His Glu Ile Gln Asp Leu Asn Val Thr Ser Gln Leu Ser Gly Asp Phe
    50                  55                  60
Glu Ala Ala His Thr Ala Gly Asp Asn Ala His Val Val Ala Thr Asp
65                  70                  75                  80
Thr Gln Lys Asn Thr Val Tyr Ala Phe Ala Arg Asp Gly Phe Ala Thr
                85                  90                  95
Thr Glu Glu Phe Leu Leu Arg Leu Gly Lys His Phe Thr Glu Gly Phe
            100                 105                 110
Asp Trp Val Thr Gly Gly Arg Trp Ala Ala Gln Gln Phe Phe Trp Asp
        115                 120                 125
Arg Ile Asn Asp His Asp His Ala Phe Ser Arg Asn Lys Ser Glu Val
    130                 135                 140
Arg Thr Ala Val Leu Glu Ile Ser Gly Ser Glu Gln Ala Ile Val Ala
145                 150                 155                 160
Gly Ile Glu Gly Leu Thr Val Leu Lys Ser Thr Gly Ser Glu Phe His
                165                 170                 175
Gly Phe Pro Arg Asp Lys Tyr Thr Thr Leu Gln Glu Thr Thr Asp Arg
            180                 185                 190
Ile Leu Ala Thr Asp Val Ser Ala Arg Trp Arg Tyr Asn Thr Val Glu
        195                 200                 205
```

```
Val Asp Phe Asp Ala Val Tyr Ala Ser Val Arg Gly Leu Leu Lys
    210                 215                 220

Ala Phe Ala Glu Thr His Ser Leu Ala Leu Gln Gln Thr Met Tyr Glu
225                 230                 235                 240

Met Gly Arg Ala Val Ile Glu Thr His Pro Glu Ile Asp Glu Ile Lys
                245                 250                 255

Met Ser Leu Pro Asn Lys His His Phe Leu Val Asp Leu Gln Pro Phe
                260                 265                 270

Gly Gln Asp Asn Pro Asn Glu Val Phe Tyr Ala Ala Asp Arg Pro Tyr
                275                 280                 285

Gly Leu Ile Glu Ala Thr Ile Gln Arg Glu Gly Ser Arg Ala Asp
290                 295                 300
```

<210> SEQ ID NO 18
<211> LENGTH: 290
<212> TYPE: PRT
<213> ORGANISM: Artificial Sequence
<220> FEATURE:
<223> OTHER INFORMATION: Modified Arthrobacter globiformis Uricase (C-term truncation with SGD)

<400> SEQUENCE: 18

```
Met Ala Thr Ala Glu Thr Ser Thr Gly Thr Lys Val Val Leu Gly Gln
1               5                   10                  15

Asn Gln Tyr Gly Lys Ala Glu Val Arg Leu Val Lys Val Thr Arg Asn
                20                  25                  30

Thr Ala Arg His Glu Ile Gln Asp Leu Asn Val Thr Ser Gln Leu Ser
            35                  40                  45

Gly Asp Phe Glu Ala Ala His Thr Ala Gly Asp Asn Ala His Val Val
50                  55                  60

Ala Thr Asp Thr Gln Lys Asn Thr Val Tyr Ala Phe Ala Arg Asp Gly
65                  70                  75                  80

Phe Ala Thr Thr Glu Glu Phe Leu Leu Arg Leu Gly Lys His Phe Thr
                85                  90                  95

Glu Gly Phe Asp Trp Val Thr Gly Gly Arg Trp Ala Ala Gln Gln Phe
            100                 105                 110

Phe Trp Asp Arg Ile Asn Asp His Asp His Ala Phe Ser Arg Asn Lys
        115                 120                 125

Ser Glu Val Arg Thr Ala Val Leu Glu Ile Ser Gly Ser Glu Gln Ala
    130                 135                 140

Ile Val Ala Gly Ile Glu Gly Leu Thr Val Leu Lys Ser Thr Gly Ser
145                 150                 155                 160

Glu Phe His Gly Phe Pro Arg Asp Lys Tyr Thr Thr Leu Gln Glu Thr
                165                 170                 175

Thr Asp Arg Ile Leu Ala Thr Asp Val Ser Ala Arg Trp Arg Tyr Asn
            180                 185                 190

Thr Val Glu Val Asp Phe Asp Ala Val Tyr Ala Ser Val Arg Gly Leu
        195                 200                 205

Leu Leu Lys Ala Phe Ala Glu Thr His Ser Leu Ala Leu Gln Gln Thr
    210                 215                 220

Met Tyr Glu Met Gly Arg Ala Val Ile Glu Thr His Pro Glu Ile Asp
225                 230                 235                 240

Glu Ile Lys Met Ser Leu Pro Asn Lys His His Phe Leu Val Asp Leu
                245                 250                 255

Gln Pro Phe Gly Gln Asp Asn Pro Asn Glu Val Phe Tyr Ala Ala Asp
            260                 265                 270
```

-continued

```
Arg Pro Tyr Gly Leu Ile Glu Ala Thr Ile Gln Arg Glu Gly Ser Arg
        275                 280                 285

Ala Asp
    290

<210> SEQ ID NO 19
<211> LENGTH: 289
<212> TYPE: PRT
<213> ORGANISM: Artificial Sequence
<220> FEATURE:
<223> OTHER INFORMATION: Modified Arthrobacter globiformis Uricase
      (processed form - Met cleaved at N-term., SGD, and C-term
      truncation)

<400> SEQUENCE: 19

Ala Thr Ala Glu Thr Ser Thr Gly Thr Lys Val Val Leu Gly Gln Asn
1               5                   10                  15

Gln Tyr Gly Lys Ala Glu Val Arg Leu Val Lys Val Thr Arg Asn Thr
            20                  25                  30

Ala Arg His Glu Ile Gln Asp Leu Asn Val Thr Ser Gln Leu Ser Gly
        35                  40                  45

Asp Phe Glu Ala Ala His Thr Ala Gly Asp Asn Ala His Val Val Ala
    50                  55                  60

Thr Asp Thr Gln Lys Asn Thr Val Tyr Ala Phe Ala Arg Asp Gly Phe
65                  70                  75                  80

Ala Thr Thr Glu Glu Phe Leu Leu Arg Leu Gly Lys His Phe Thr Glu
                85                  90                  95

Gly Phe Asp Trp Val Thr Gly Gly Arg Trp Ala Ala Gln Gln Phe Phe
            100                 105                 110

Trp Asp Arg Ile Asn Asp His Asp His Ala Phe Ser Arg Asn Lys Ser
        115                 120                 125

Glu Val Arg Thr Ala Val Leu Glu Ile Ser Gly Ser Glu Gln Ala Ile
    130                 135                 140

Val Ala Gly Ile Glu Gly Leu Thr Val Leu Lys Ser Thr Gly Ser Glu
145                 150                 155                 160

Phe His Gly Phe Pro Arg Asp Lys Tyr Thr Thr Leu Gln Glu Thr Thr
                165                 170                 175

Asp Arg Ile Leu Ala Thr Asp Val Ser Ala Arg Trp Arg Tyr Asn Thr
            180                 185                 190

Val Glu Val Asp Phe Asp Ala Val Tyr Ala Ser Val Arg Gly Leu Leu
        195                 200                 205

Leu Lys Ala Phe Ala Glu Thr His Ser Leu Ala Leu Gln Gln Thr Met
    210                 215                 220

Tyr Glu Met Gly Arg Ala Val Ile Glu Thr His Pro Glu Ile Asp Glu
225                 230                 235                 240

Ile Lys Met Ser Leu Pro Asn Lys His His Phe Leu Val Asp Leu Gln
                245                 250                 255

Pro Phe Gly Gln Asp Asn Pro Asn Glu Val Phe Tyr Ala Ala Asp Arg
            260                 265                 270

Pro Tyr Gly Leu Ile Glu Ala Thr Ile Gln Arg Glu Gly Ser Arg Ala
        275                 280                 285

Asp

<210> SEQ ID NO 20
<211> LENGTH: 303
<212> TYPE: PRT
```

```
<213> ORGANISM: Artificial Sequence
<220> FEATURE:
<223> OTHER INFORMATION: Modified Arthrobacter globiformis Uricase
      (contains optional N-terminal His tag and optional short linker,
      contains SGD instead of RGD) (C-term truncation with his tag and
      SGD)
<220> FEATURE:
<221> NAME/KEY: MISC_FEATURE
<222> LOCATION: (1)..(13)
<223> OTHER INFORMATION: Optional N-terminal His tag and optional linker

<400> SEQUENCE: 20

Met Gly Ser His His His His His Gly Ala Arg Gln Thr Ala Thr
1               5                   10                  15

Ala Glu Thr Ser Thr Gly Thr Lys Val Val Leu Gly Gln Asn Gln Tyr
                20                  25                  30

Gly Lys Ala Glu Val Arg Leu Val Lys Val Thr Arg Asn Thr Ala Arg
            35                  40                  45

His Glu Ile Gln Asp Leu Asn Val Thr Ser Gln Leu Ser Gly Asp Phe
    50                  55                  60

Glu Ala Ala His Thr Ala Gly Asp Asn Ala His Val Val Ala Thr Asp
65                  70                  75                  80

Thr Gln Lys Asn Thr Val Tyr Ala Phe Ala Arg Asp Gly Phe Ala Thr
                85                  90                  95

Thr Glu Glu Phe Leu Leu Arg Leu Gly Lys His Phe Thr Glu Gly Phe
            100                 105                 110

Asp Trp Val Thr Gly Gly Arg Trp Ala Ala Gln Gln Phe Phe Trp Asp
        115                 120                 125

Arg Ile Asn Asp His Asp His Ala Phe Ser Arg Asn Lys Ser Glu Val
130                 135                 140

Arg Thr Ala Val Leu Glu Ile Ser Gly Ser Glu Gln Ala Ile Val Ala
145                 150                 155                 160

Gly Ile Glu Gly Leu Thr Val Leu Lys Ser Thr Gly Ser Glu Phe His
                165                 170                 175

Gly Phe Pro Arg Asp Lys Tyr Thr Thr Leu Gln Glu Thr Thr Asp Arg
            180                 185                 190

Ile Leu Ala Thr Asp Val Ser Ala Arg Trp Arg Tyr Asn Thr Val Glu
        195                 200                 205

Val Asp Phe Asp Ala Val Tyr Ala Ser Val Arg Gly Leu Leu Leu Lys
    210                 215                 220

Ala Phe Ala Glu Thr His Ser Leu Ala Leu Gln Gln Thr Met Tyr Glu
225                 230                 235                 240

Met Gly Arg Ala Val Ile Glu Thr His Pro Glu Ile Asp Glu Ile Lys
                245                 250                 255

Met Ser Leu Pro Asn Lys His His Phe Leu Val Asp Leu Gln Pro Phe
            260                 265                 270

Gly Gln Asp Asn Pro Asn Glu Val Phe Tyr Ala Ala Asp Arg Pro Tyr
        275                 280                 285

Gly Leu Ile Glu Ala Thr Ile Gln Arg Glu Gly Ser Arg Ala Asp
    290                 295                 300

<210> SEQ ID NO 21
<211> LENGTH: 303
<212> TYPE: PRT
<213> ORGANISM: Artificial Sequence
<220> FEATURE:
<223> OTHER INFORMATION: Modified Arthrobacter globiformis Uricase
      (contains optional N-terminal His tag and optional short linker)
      (C-term truncation with his tag)
```

```
<220> FEATURE:
<221> NAME/KEY: MISC_FEATURE
<222> LOCATION: (1)..(13)
<223> OTHER INFORMATION: Optional N-terminal His tag and optional linker

<400> SEQUENCE: 21
```

Met Gly Ser His His His His His Gly Ala Arg Gln Thr Ala Thr
1               5                   10                  15

Ala Glu Thr Ser Thr Gly Thr Lys Val Val Leu Gly Gln Asn Gln Tyr
            20                  25                  30

Gly Lys Ala Glu Val Arg Leu Val Lys Val Thr Arg Asn Thr Ala Arg
        35                  40                  45

His Glu Ile Gln Asp Leu Asn Val Thr Ser Gln Leu Arg Gly Asp Phe
    50                  55                  60

Glu Ala Ala His Thr Ala Gly Asp Asn Ala His Val Val Ala Thr Asp
65                  70                  75                  80

Thr Gln Lys Asn Thr Val Tyr Ala Phe Ala Arg Asp Gly Phe Ala Thr
                85                  90                  95

Thr Glu Glu Phe Leu Leu Arg Leu Gly Lys His Phe Thr Glu Gly Phe
            100                 105                 110

Asp Trp Val Thr Gly Gly Arg Trp Ala Ala Gln Phe Phe Trp Asp
        115                 120                 125

Arg Ile Asn Asp His Asp His Ala Phe Ser Arg Asn Lys Ser Glu Val
    130                 135                 140

Arg Thr Ala Val Leu Glu Ile Ser Gly Ser Glu Gln Ala Ile Val Ala
145                 150                 155                 160

Gly Ile Glu Gly Leu Thr Val Leu Lys Ser Thr Gly Ser Glu Phe His
                165                 170                 175

Gly Phe Pro Arg Asp Lys Tyr Thr Thr Leu Gln Glu Thr Thr Asp Arg
            180                 185                 190

Ile Leu Ala Thr Asp Val Ser Ala Arg Trp Arg Tyr Asn Thr Val Glu
        195                 200                 205

Val Asp Phe Asp Ala Val Tyr Ala Ser Val Arg Gly Leu Leu Leu Lys
    210                 215                 220

Ala Phe Ala Glu Thr His Ser Leu Ala Leu Gln Gln Thr Met Tyr Glu
225                 230                 235                 240

Met Gly Arg Ala Val Ile Glu Thr His Pro Glu Ile Asp Glu Ile Lys
                245                 250                 255

Met Ser Leu Pro Asn Lys His His Phe Leu Val Asp Leu Gln Pro Phe
            260                 265                 270

Gly Gln Asp Asn Pro Asn Glu Val Phe Tyr Ala Ala Asp Arg Pro Tyr
        275                 280                 285

Gly Leu Ile Glu Ala Thr Ile Gln Arg Glu Gly Ser Arg Ala Asp
    290                 295                 300

```
<210> SEQ ID NO 22
<211> LENGTH: 291
<212> TYPE: PRT
<213> ORGANISM: Artificial Sequence
<220> FEATURE:
<223> OTHER INFORMATION: Modified Arthrobacter globiformis Uricase (0
      cysteines) (truncated the C-terminal 11 amino acids to eliminate
      the Cys) (C-term truncation)

<400> SEQUENCE: 22
```

Met Thr Ala Thr Ala Glu Thr Ser Thr Gly Thr Lys Val Val Leu Gly
1               5                   10                  15

```
Gln Asn Gln Tyr Gly Lys Ala Glu Val Arg Leu Val Lys Val Thr Arg
             20                  25                  30

Asn Thr Ala Arg His Glu Ile Gln Asp Leu Asn Val Thr Ser Gln Leu
         35                  40                  45

Arg Gly Asp Phe Glu Ala Ala His Thr Ala Gly Asp Asn Ala His Val
 50                  55                  60

Val Ala Thr Asp Thr Gln Lys Asn Thr Val Tyr Ala Phe Ala Arg Asp
 65                  70                  75                  80

Gly Phe Ala Thr Thr Glu Glu Phe Leu Leu Arg Leu Gly Lys His Phe
                 85                  90                  95

Thr Glu Gly Phe Asp Trp Val Thr Gly Gly Arg Trp Ala Ala Gln Gln
                100                 105                 110

Phe Phe Trp Asp Arg Ile Asn Asp His Asp His Ala Phe Ser Arg Asn
            115                 120                 125

Lys Ser Glu Val Arg Thr Ala Val Leu Glu Ile Ser Gly Ser Glu Gln
130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
        195                 200                 205

Leu Leu Leu Lys Ala Phe Ala Glu Thr His Ser Leu Ala Leu Gln Gln
210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Glu Gly Ser
        275                 280                 285

Arg Ala Asp
    290

<210> SEQ ID NO 23
<211> LENGTH: 291
<212> TYPE: PRT
<213> ORGANISM: Artificial Sequence
<220> FEATURE:
<223> OTHER INFORMATION: Modified Arthrobacter globiformis Uricase (0
      cysteines) (RGD variants, truncated the C-terminal 11 amino acids
      to eliminate the Cys) (C-term truncation)
<220> FEATURE:
<221> NAME/KEY: MISC_FEATURE
<222> LOCATION: (49)..(49)
<223> OTHER INFORMATION: X is either R or any natural amino acid except
      C
<220> FEATURE:
<221> NAME/KEY: MISC_FEATURE
<222> LOCATION: (50)..(50)
<223> OTHER INFORMATION: X is either G or any natural amino acid except
      C
<220> FEATURE:
<221> NAME/KEY: MISC_FEATURE
<222> LOCATION: (51)..(51)
<223> OTHER INFORMATION: X is either D or any natural amino acid except
      C
```

<400> SEQUENCE: 23

```
Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
            20                  25                  30

Asn Thr Ala Arg His Glu Ile Gln Asp Leu Asn Val Thr Ser Gln Leu
        35                  40                  45

Xaa Xaa Xaa Phe Glu Ala Ala His Thr Ala Gly Asp Asn Ala His Val
50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Phe Trp Asp Arg Ile Asn Asp His Asp His Ala Phe Ser Arg Asn
        115                 120                 125

Lys Ser Glu Val Arg Thr Ala Val Leu Glu Ile Ser Gly Ser Glu Gln
130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
        195                 200                 205

Leu Leu Leu Lys Ala Phe Ala Glu Thr His Ser Leu Ala Leu Gln Gln
210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Glu Gly Ser
        275                 280                 285

Arg Ala Asp
    290
```

<210> SEQ ID NO 24
<211> LENGTH: 301
<212> TYPE: PRT
<213> ORGANISM: Artificial Sequence
<220> FEATURE:
<223> OTHER INFORMATION: Modified Arthrobacter globiformis Uricase (0 cysteines) (truncated the C-terminal aa to eliminate the cysteine)

<400> SEQUENCE: 24

```
Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
            20                  25                  30

Asn Thr Ala Arg His Glu Ile Gln Asp Leu Asn Val Thr Ser Gln Leu
        35                  40                  45
```

```
Arg Gly Asp Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Phe Trp Asp Arg Ile Asn Asp His Asp Ala Phe Ser Arg Asn
        115                 120                 125

Lys Ser Glu Val Arg Thr Ala Val Leu Glu Ile Ser Gly Ser Glu Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
        195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Glu Gly Ser
        275                 280                 285

Arg Ala Asp His Pro Ile Trp Ser Asn Ile Ala Gly Phe
    290                 295                 300
```

<210> SEQ ID NO 25
<211> LENGTH: 301
<212> TYPE: PRT
<213> ORGANISM: Artificial Sequence
<220> FEATURE:
<223> OTHER INFORMATION: Modified Arthrobacter globiformis Uricase (0 cysteines) (RGD variants, truncated the C-terminal aa to eliminate the cysteine)
<220> FEATURE:
<221> NAME/KEY: MISC_FEATURE
<222> LOCATION: (49)..(49)
<223> OTHER INFORMATION: X is either R or any natural amino acid except C
<220> FEATURE:
<221> NAME/KEY: MISC_FEATURE
<222> LOCATION: (50)..(50)
<223> OTHER INFORMATION: X is either G or any natural amino acid except C
<220> FEATURE:
<221> NAME/KEY: MISC_FEATURE
<222> LOCATION: (51)..(51)
<223> OTHER INFORMATION: X is either D or any natural amino acid except C

<400> SEQUENCE: 25

```
Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
```

```
                20                  25                  30
Asn Thr Ala Arg His Glu Ile Gln Asp Leu Asn Val Thr Ser Gln Leu
            35                  40                  45

Xaa Xaa Xaa Phe Glu Ala Ala His Thr Ala Gly Asp Asn Ala His Val
50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Phe Trp Asp Arg Ile Asn Asp His Asp His Ala Phe Ser Arg Asn
            115                 120                 125

Lys Ser Glu Val Arg Thr Ala Val Leu Glu Ile Ser Gly Ser Glu Gln
130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
            195                 200                 205

Leu Leu Leu Lys Ala Phe Ala Glu Thr His Ser Leu Ala Leu Gln Gln
210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Glu Gly Ser
            275                 280                 285

Arg Ala Asp His Pro Ile Trp Ser Asn Ile Ala Gly Phe
            290                 295                 300

<210> SEQ ID NO 26
<211> LENGTH: 302
<212> TYPE: PRT
<213> ORGANISM: Artificial Sequence
<220> FEATURE:
<223> OTHER INFORMATION: Modified Arthrobacter globiformis Uricase (RGD
      variants) (contains the C-terminal 11 amino acids)
<220> FEATURE:
<221> NAME/KEY: MISC_FEATURE
<222> LOCATION: (49)..(49)
<223> OTHER INFORMATION: X is either R or any natural amino acid
<220> FEATURE:
<221> NAME/KEY: MISC_FEATURE
<222> LOCATION: (50)..(50)
<223> OTHER INFORMATION: X is either G or any natural amino acid
<220> FEATURE:
<221> NAME/KEY: MISC_FEATURE
<222> LOCATION: (51)..(51)
<223> OTHER INFORMATION: X is either D or any natural amino acid

<400> SEQUENCE: 26

Met Thr Ala Thr Ala Glu Thr Ser Thr Gly Thr Lys Val Val Leu Gly
1               5                   10                  15
```

Gln Asn Gln Tyr Gly Lys Ala Glu Val Arg Leu Val Lys Val Thr Arg
            20                  25                  30

Asn Thr Ala Arg His Glu Ile Gln Asp Leu Asn Val Thr Ser Gln Leu
        35                  40                  45

Xaa Xaa Xaa Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Phe Trp Asp Arg Ile Asn Asp His Asp His Ala Phe Ser Arg Asn
        115                 120                 125

Lys Ser Glu Val Arg Thr Ala Val Leu Glu Ile Ser Gly Ser Glu Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
        195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Glu Gly Ser
        275                 280                 285

Arg Ala Asp His Pro Ile Trp Ser Asn Ile Ala Gly Phe Cys
    290                 295                 300

<210> SEQ ID NO 27
<211> LENGTH: 302
<212> TYPE: PRT
<213> ORGANISM: Arthrobacter globiformis

<400> SEQUENCE: 27

Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
            20                  25                  30

Asn Thr Ala Arg His Glu Ile Gln Asp Leu Asn Val Thr Ser Gln Leu
        35                  40                  45

Arg Gly Asp Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

```
Thr Glu Gly Phe Asp Trp Val Thr Gly Gly Arg Trp Ala Ala Gln Gln
            100                 105                 110

Phe Phe Trp Asp Arg Ile Asn Asp His Asp His Ala Phe Ser Arg Asn
            115                 120                 125

Lys Ser Glu Val Arg Thr Ala Val Leu Glu Ile Ser Gly Ser Glu Gln
        130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
        195                 200                 205

Leu Leu Leu Lys Ala Phe Ala Glu Thr His Ser Leu Ala Leu Gln Gln
        210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Glu Gly Ser
        275                 280                 285

Arg Ala Asp His Pro Ile Trp Ser Asn Ile Ala Gly Phe Cys
        290                 295                 300

<210> SEQ ID NO 28
<211> LENGTH: 293
<212> TYPE: PRT
<213> ORGANISM: Deinococcus geothermalis

<400> SEQUENCE: 28

Met Thr Gln Thr Gln Asn Gln Gln Pro Lys Val Lys Ala Arg Leu
1               5                   10                  15

Gly Ala Asn Asn Tyr Gly Lys Ala Glu Val Asn Leu Met Lys Val Lys
            20                  25                  30

Arg Asp Ser Glu Arg His Glu Ile Arg Glu Leu Gln Val Arg Val Ala
        35                  40                  45

Leu Ile Gly Asp Phe Ala Ala Ala His Glu Gln Gly Asp Asn Thr Asp
    50                  55                  60

Leu Leu Ala Thr Asp Thr Val Arg Asn Thr Ile Tyr Gly Leu Ala Lys
65                  70                  75                  80

Glu Gly Phe Gln Ala Ser Pro Glu Ala Phe Gly Lys Glu Leu Ile Ser
                85                  90                  95

His Phe Val Thr Thr Gly Pro Lys Val Thr Gly Phe Met Glu Phe
            100                 105                 110

Thr Glu Tyr Leu Trp Glu Arg Ile Gln Val Gly Gly Glu Gly His Asn
            115                 120                 125

His Ala Phe Val Arg Gln Met Pro Gln Arg Thr Gly Arg Val Glu Ser
        130                 135                 140

Glu Asp Gly Lys Thr Phe Lys Ile Thr Ser Gly Leu Gln Asn Leu Tyr
145                 150                 155                 160

Val Leu Lys Thr Thr Glu Ser Gly Trp Ala Asn Tyr Leu Leu Asn Glu
```

```
                    165                 170                 175
Arg Phe Thr Thr Leu Pro Glu Thr His Glu Arg Leu Met Ala Ser Phe
                180                 185                 190

Val Thr Ala Lys Trp Glu Tyr Asn Glu Asp Gln Val Asp Tyr Asp Asp
            195                 200                 205

Val Trp Pro Arg Val Tyr Arg Gln Leu Gln Glu Thr Phe Thr Asp His
        210                 215                 220

Tyr Ser Pro Ser Leu Gln Arg Thr Leu Phe Leu Met Gly Gln Ala Val
225                 230                 235                 240

Leu Thr Arg Cys Pro Glu Met Ser Arg Ile Trp Leu Gln Met Pro Asn
                245                 250                 255

Lys His His Leu Gln Tyr Asn Leu Glu Arg Phe Gly Leu Asp Asn Asn
                260                 265                 270

Leu Glu Ile Phe His Val Asp Pro Glu Pro Tyr Gly Leu Met Glu Ala
                275                 280                 285

Trp Val Glu Arg Ala
            290

<210> SEQ ID NO 29
<211> LENGTH: 298
<212> TYPE: PRT
<213> ORGANISM: Deinococcus radiodurans

<400> SEQUENCE: 29

Met Met Thr Gly Thr Gln Gln Pro Gly Thr Gln Pro Lys Val Lys Val
1               5                   10                  15

Arg Leu Gly Glu Asn Asn Tyr Gly Lys Ala Glu Val Gln Leu Met Lys
                20                  25                  30

Ile Lys Arg Gly Thr Pro Arg His Glu Leu Arg Glu Ala Lys Val Arg
            35                  40                  45

Val Ala Met Tyr Gly Asp Phe Gly Ala Ala His Ser Glu Gly Asp Asn
        50                  55                  60

Thr Asp Leu Val Ala Thr Asp Thr Val Arg Asn Thr Val Tyr Gly Leu
65                  70                  75                  80

Ala Lys Glu Gly Phe Glu Ser Ser Ile Glu Glu Phe Lys Glu Leu
                85                  90                  95

Leu Thr His Phe Val Lys Val Gly Pro Arg Val Thr Gly Gly Phe Ala
            100                 105                 110

Glu Phe Thr Glu His Leu Trp Glu Arg Val Gln Thr Pro Ala Gln Pro
        115                 120                 125

Gln Gly His Asp His Ala Phe Val Arg Gln Met Pro Lys Arg Thr Ala
    130                 135                 140

Arg Val Glu Thr Gln Asp Gly Arg Arg Phe Thr Val Thr Ser Gly Ile
145                 150                 155                 160

Glu Glu Leu Tyr Val Leu Lys Thr Thr Glu Ser Gly Trp Glu Asn Tyr
                165                 170                 175

Leu Leu Asp Glu Arg Phe Thr Thr Leu Pro Glu Thr His Asp Arg Val
            180                 185                 190

Met Ala Thr Phe Val Thr Ala Lys Trp Glu Tyr Ala Val Glu Ser Cys
        195                 200                 205

Asp Tyr Asp Ala Val Trp Glu Arg Val Tyr Arg Gln Ile Gln His Thr
    210                 215                 220

Phe Thr Asp His Tyr Ser Pro Ser Leu Gln Arg Thr Leu Tyr Leu Met
225                 230                 235                 240
```

```
Gly Glu Ala Val Leu Ser Val Cys Pro Glu Ile Ser Arg Ile Trp Phe
            245                 250                 255
Gln Met Pro Asn Lys His His Leu Val Tyr Asn Leu Gly Arg Phe Gly
        260                 265                 270
Leu Glu Asn Asn Asn Glu Ile Leu His Val Asp Pro Glu Pro Tyr Gly
    275                 280                 285
Leu Met Glu Ala Trp Val Glu Arg Ala Glu
        290                 295
```

<210> SEQ ID NO 30
<211> LENGTH: 287
<212> TYPE: PRT
<213> ORGANISM: Granulicella tundricola

<400> SEQUENCE: 30

```
Met Ala Glu Leu Thr Asp Ala Lys Phe Glu Ile Val Ala Asn Arg Tyr
1               5                   10                  15
Gly Lys Ser Lys Val Arg Leu Leu Lys Val Thr Arg Ala Glu Gly Arg
            20                  25                  30
Ser Asp Val His Glu Trp Thr Val Gln Val Leu Arg Gly Asp Phe
        35                  40                  45
Glu Thr Ala His Thr Val Gly Asp Asn Ser Lys Ile Val Thr Thr Asp
    50                  55                  60
Thr Met Lys Asn Thr Val Tyr Ser Leu Ala Arg Trp Ser Ser Ala Thr
65                  70                  75                  80
Thr Met Glu Glu Phe Ala Glu Glu Leu Ile Glu His Leu Leu Arg Arg
                85                  90                  95
Asn Glu Gln Val Ser Ser Val Arg Val His Ile Glu Ala Ala Leu Trp
            100                 105                 110
Lys Arg Leu Thr Val Asp Gly Lys Glu His Pro Asp Thr Phe Met Arg
        115                 120                 125
Gly Ser Asn Glu Val Gln Thr Ala Thr Val Glu Gln Ala Arg Ala Gly
    130                 135                 140
Glu Lys Lys Phe Ile Ala Gly Phe Ala Asn Leu Gln Leu Leu Lys Thr
145                 150                 155                 160
Ala Asn Ser Ala Phe Ser Gly Phe Gln Arg Asp Glu Leu Thr Thr Leu
                165                 170                 175
Pro Glu Thr Arg Asp Arg Val Phe Gly Thr Ala Val Ala Lys Trp
            180                 185                 190
Thr Tyr Ser Gly Pro Val Glu Phe Ala Ala Met Arg Lys Ala Ala Arg
        195                 200                 205
Glu Val Met Leu Lys Val Phe Ala Asp His Met Ser Glu Ser Val Gln
    210                 215                 220
His Thr Leu Tyr Ala Met Ala Asp Ala Ala Leu Glu Ala Val Ala Glu
225                 230                 235                 240
Ile Thr Glu Ile Glu Leu Ala Met Pro Asn Lys His Cys Leu Leu Val
                245                 250                 255
Asp Leu Ser Lys Phe Gly Gln Asp Asn Pro Asn Gln Ile Phe Val Pro
            260                 265                 270
Thr Asp Glu Pro His Gly Tyr Ile Glu Ala Arg Val Arg Arg Lys
        275                 280                 285
```

<210> SEQ ID NO 31
<211> LENGTH: 287
<212> TYPE: PRT
<213> ORGANISM: Solibacter usitatus

<400> SEQUENCE: 31

```
Met Glu Arg Phe Ala Ser Gly Trp Lys Gln Asn Tyr Tyr Gly Lys Gly
1               5                   10                  15

Asp Val Ile Val Tyr Arg Leu Asn Arg Asp Gly Val Val Pro Gln Gly
            20                  25                  30

Cys Cys Pro Val Phe Gly Ala Asn Val Lys Met Leu Leu Tyr Gly Asp
        35                  40                  45

Ala Phe Trp Pro Thr Tyr Thr Thr Gly Asp Asn Thr Asn Leu Val Ala
    50                  55                  60

Thr Asp Ser Met Lys Asn Phe Ile Gln Arg Glu Thr Cys Asn Phe Thr
65                  70                  75                  80

Gly Tyr Asp Leu Glu Ser Tyr Cys Asp Phe Leu Ala Arg Lys Phe Met
                85                  90                  95

Ala Thr Tyr Pro His Thr Ala Gly Ile Gln Leu Ser Ala Arg Gln Ala
            100                 105                 110

Pro Tyr Ser Gly Val Ala Glu Gly Lys Val Ala Phe Ala Pro Ser Gly
        115                 120                 125

Pro Asp Val Ala Thr Ala Cys Val Glu Leu Arg Arg Asn Gly Glu Ala
    130                 135                 140

Leu Glu Ser Val Glu Ala Ser Ser Gly Ile His Gly Phe Arg Leu Leu
145                 150                 155                 160

Arg Leu Gly Gly Ser Ala Phe Gln Gly Phe Leu Arg Asp Gln Tyr Thr
                165                 170                 175

Thr Leu Pro Asp Ile His Asn Arg Pro Leu His Met Trp Leu Asp Leu
            180                 185                 190

Glu Trp His Tyr Ile Ala Pro Glu Ala Ala Leu Thr Gly Gly Glu Val
        195                 200                 205

Thr Ala Gln Val Arg Arg Leu Val His Glu Gly Phe His Ser Phe Glu
    210                 215                 220

Ser Gly Ser Ile Gln Gln Val Ile Tyr Gln Leu Gly Thr Lys Met Leu
225                 230                 235                 240

Ala Asp Ile Pro Thr Ile Ser Glu Val Arg Leu Glu Ala Asn Asn Arg
                245                 250                 255

Thr Trp Asp Thr Ile Val Glu Gln Gly Asp Arg Leu Gly Val Tyr Thr
            260                 265                 270

Asp Ala Arg Pro Pro Tyr Gly Cys Leu Gly Leu Thr Leu Arg Arg
        275                 280                 285
```

<210> SEQ ID NO 32
<211> LENGTH: 280
<212> TYPE: PRT
<213> ORGANISM: Terriglobus saanensis

<400> SEQUENCE: 32

```
Met Ala Lys Leu Ile Asp Ser Arg Tyr Gly Lys Ala Arg Val Arg Val
1               5                   10                  15

Met Lys Leu Asp Arg Ser Gln Pro Gln His Gln Leu Leu Glu Trp Thr
            20                  25                  30

Val Arg Val Leu Leu Glu Gly Asp Phe Glu Thr Ala His Thr Val Gly
        35                  40                  45

Asp Asn Ser Asn Ile Leu Pro Thr Asp Thr Met Lys Asn Thr Val Tyr
    50                  55                  60

Ser Arg Ala Lys Glu Ser Lys Ala Glu Thr Pro Glu Glu Phe Ala Ile
65                  70                  75                  80
```

```
Glu Leu Ala Glu Phe Leu Leu Gly Arg Asn Pro Gln Val His Thr Val
                85                  90                  95

Glu Val Lys Ile Glu Thr Ala Met Trp Lys Arg Leu Val Val Asp Gly
            100                 105                 110

Lys Pro His Gly Ser Ser Phe Met Arg Gly Ser Asp Glu Leu Gly Thr
            115                 120                 125

Val Leu His His Ala Thr Arg Glu Thr Lys Thr Met Val Cys Gly Val
130                 135                 140

Glu Asn Met Val Ile Leu Lys Ser Gln Asn Ser Ser Phe Glu Gly Tyr
145                 150                 155                 160

Ile Gln Asp Asp Leu Thr Thr Leu Lys Pro Thr Ala Asp Arg Leu Phe
                165                 170                 175

Ala Thr Ala Met Thr Ala Asp Trp Asp Tyr Thr Asp Gly Gly Ser Ala
            180                 185                 190

Phe Ala Ala Arg Arg Glu Ala Ile Arg Glu Ala Met Leu Lys Ala Phe
            195                 200                 205

Ala Glu His Asp Ser Lys Ser Val Gln Gln Thr Leu Tyr Ala Met Ala
210                 215                 220

Glu Ala Ala Met Ala Ala Val Pro Ala Val Asn Arg Val His Met Val
225                 230                 235                 240

Met Pro Asn Lys His Cys Leu Leu Val Asp Leu Lys His Phe Gly Gln
                245                 250                 255

Glu Asn Asn Asn Glu Ile Phe Val Pro Thr Glu Asp Pro His Gly Tyr
            260                 265                 270

Ile Glu Ala Thr Val Val Arg Glu
            275                 280

<210> SEQ ID NO 33
<211> LENGTH: 326
<212> TYPE: PRT
<213> ORGANISM: Kyrpidia tusciae

<400> SEQUENCE: 33

Met Ile Met Thr Gly Thr Met Thr Ser Gly Thr Asp Gln Arg Thr Met
1               5                   10                  15

Tyr Tyr Gly Lys Gly Asp Val Trp Val Tyr Arg Ser Tyr Ala Lys Pro
            20                  25                  30

Leu Arg Gly Leu Gly Gln Ile Pro Glu Ser Ala Phe Ala Gly Arg Pro
        35                  40                  45

Asn Val Ile Phe Gly Met Asn Val Gln Met Ala Val Glu Gly Glu Ala
50                  55                  60

Phe Leu Pro Ser Phe Thr Glu Gly Asp Asn Ser Met Val Val Ala Thr
65                  70                  75                  80

Asp Ser Met Lys Asn Phe Ile Leu Arg Gln Ala Gly Ala Phe Glu Gly
                85                  90                  95

Ala Thr Ala Glu Gly Phe Leu Glu Phe Val Ala Gly Lys Phe Leu Glu
            100                 105                 110

Lys Tyr Ala His Val Ser Gly Val Arg Leu Phe Gly Arg Gln Ile Pro
            115                 120                 125

Phe Asp Glu Leu Pro Val Pro Glu Gln Glu Gly Phe Arg Pro Gly Glu
            130                 135                 140

Leu Val Phe Arg Tyr Ser Met Asn Glu Tyr Pro Thr Ala Phe Val Ala
145                 150                 155                 160

Val Arg Arg Gly Pro Glu Gly Pro Val Val Glu His Ala Gly Gly
```

```
                165                 170                 175
Val Ala Gly Leu Lys Leu Ile Lys Ile Lys Gly Ser Ser Phe Tyr Gly
            180                 185                 190

Tyr Ile His Asp Glu Tyr Thr Thr Leu Pro Glu Ala Gln Asp Arg Pro
        195                 200                 205

Leu Phe Ile Tyr Leu Tyr Ile Lys Trp Lys Tyr Glu His Pro Glu Asp
        210                 215                 220

Phe Arg Ala Glu His Pro Glu Arg Tyr Val Ala Ala Glu Gln Val Arg
225                 230                 235                 240

Asp Ile Ala His Thr Val Phe His Glu Leu Thr Ser Pro Ser Ile Gln
                245                 250                 255

Asn Leu Ile Tyr His Ile Gly Arg Arg Val Leu Thr Arg Phe Pro Gln
                260                 265                 270

Leu Leu Glu Val Ser Phe Glu Ala Asn Asn Arg Thr Trp Glu Thr Val
                275                 280                 285

Leu Glu Glu Val Glu Asp Leu Ala Gly Lys Arg Ala Glu Ala Lys Val
            290                 295                 300

Tyr Thr Glu Pro Arg Pro Pro Tyr Gly Phe Gln Gly Phe Thr Val Thr
305                 310                 315                 320

Arg Lys Asp Leu Glu Glu
                325

<210> SEQ ID NO 34
<211> LENGTH: 304
<212> TYPE: PRT
<213> ORGANISM: Artificial Sequence
<220> FEATURE:
<223> OTHER INFORMATION: Consensus Uricase sequence from alignment

<400> SEQUENCE: 34

Met Thr Ala Thr Ala Glu Thr Ser Thr Gly Thr Lys Ile Val Leu Gly
1               5                   10                  15

Gln Asn Gln Tyr Gly Lys Ala Glu Val Arg Val Val Lys Ile Thr Arg
            20                  25                  30

Asp Gly Asp Thr His His Ile Lys Asp Leu Asn Val Ser Val Ala Leu
        35                  40                  45

Ser Gly Asp Met Asp Ala Val His Leu Ser Gly Asp Asn Ala Asn Val
    50                  55                  60

Leu Pro Thr Asp Thr Gln Lys Asn Thr Val Tyr Ala Phe Ala Lys Glu
65                  70                  75                  80

His Gly Ile Gly Ser Ala Glu Gln Phe Gly Ile Arg Leu Ala Arg His
                85                  90                  95

Phe Val Thr Ser Gln Glu Pro Ile His Gly Ala Arg Ile Arg Ile Glu
            100                 105                 110

Glu Tyr Ala Trp Glu Arg Ile Glu Thr Ser His Asp His Ser Phe Val
        115                 120                 125

Arg Lys Gly Gln Glu Thr Arg Thr Ala Gln Ile Thr Tyr Asp Gly Asp
    130                 135                 140

Trp Glu Val Val Ser Gly Leu Lys Asp Leu Thr Val Leu Asn Ser Thr
145                 150                 155                 160

Gly Ser Glu Phe Trp Gly Tyr Val Lys Asp Lys Tyr Thr Thr Leu Pro
                165                 170                 175

Glu Thr Tyr Asp Arg Ile Leu Ala Thr Asp Val Ser Ala Arg Trp Arg
            180                 185                 190

Tyr Asn Trp Thr Asp Asp Gln Pro Met Pro Asp Trp Asp Lys Ser Tyr
```

-continued

```
                195                 200                 205
Glu Gln Val Arg Lys His Leu Leu Glu Ala Phe Ala Glu Thr Tyr Ser
    210                 215                 220

Leu Ser Leu Gln Gln Thr Leu Tyr Gln Met Gly Ser Arg Val Leu Glu
225                 230                 235                 240

Ala Arg Pro Glu Ile Asp Glu Ile Arg Phe Ser Leu Pro Asn Lys His
                245                 250                 255

His Phe Leu Val Asp Leu Glu Pro Phe Gly Leu Asp Asn Asp Asn Glu
            260                 265                 270

Val Tyr Phe Ala Ala Asp Arg Pro Tyr Gly Leu Ile Glu Ala Thr Val
        275                 280                 285

Leu Arg Asp Gly Ala Glu Pro Arg Ile Pro Val Asp Met Thr Asn Leu
290                 295                 300
```

URICASE SEQUENCES AND METHODS OF TREATMENT

CROSS-REFERENCE TO RELATED APPLICATIONS

This application is a U.S. National Stage application of International Application No. PCT/US2016/032415, filed on May 13, 2016, said International Application No. PCT/US2016/032415 claims the benefit of U.S. Provisional Patent Application No. 62/162,280, filed May 15, 2015, which is incorporated by reference herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 103,752 Byte ASCII (Text) file named "UCASE-100-US-PCT-SequenceListing" created on Nov. 14, 2017.

BACKGROUND OF THE INVENTION

A functional uricase can be found in a wide range of organisms, such as archaea, bacteria, and eukaryotes. However, in humans and some primates uricase is not expressed. The lack of uricase expression in humans has resulted in higher systemic uric acid levels, and in some cases, hyperuricemia conditions such as gout and tumor lysis syndrome.

Gout affects more than 8 million Americans and is a painful and debilitating inflammatory arthritis defined as serum uric acid levels exceeding uric acid solubility in body fluids. The damage caused by gout can result in chronic pain, functional impairment at work and at home, and compromised health-related quality of life (see, e.g., Wertheimer, et al., *Curr Ther Res Clin Exp.*, 75: 1-4 (2013)).

Tumor lysis syndrome (TLS) usually occurs in patients with bulky, rapidly-proliferating, and treatment-responsive tumors. TLS is a potentially lethal complication of anticancer treatment that arises when large numbers of cancer cells are killed quickly and release breakdown products that lead to a sharp increase in systemic uric acid.

A variety of mechanisms of action exist for controlling hyperuricemia, such as inhibitors of xanthine oxidase (enzyme that converts xanthine to uric acid), uricosuric drugs (molecules that inhibit URAT1), and uricase treatment.

There are two clinically approved uricases, Krystexxa® and Elitek®. Krystexxa® (pegloticase) is a PEGylated uricase approved for the treatment of chronic gout in adult patients refractory to conventional therapy. Krystexxa® is a chimeric protein of the pig and baboon uricase sequence that is hyper-PEGylated (~440 kDa PEG per tetramer). Krystexxa® is administered by an intravenous (IV) infusion over a 2 hour period. During phase 3 clinical trials, 26% of patients experienced infusion reactions and 6.5% of patients had reactions characterized as anaphylaxis (Baraf et al., *Arthritis Res Ther.*, 15(5):R137 (2013) and Strand et al., *J Rheumatol.*, 39(7): 1450-1457 (2012). Krystexxa® contains a black box warning for anaphylaxis and infusion reactions (see Krystexxa® prescribing information). As a result, patients are typically pretreated with antihistamines or corticosteroids prior to the IV infusion and then monitored post-infusion. Pretreatment, IV-infusion and post-infusion monitoring takes about 6-8 hours in an IV clinic.

Elitek® (rasburicase) is a modified recombinant *Aspergillus flavus* uricase that is indicated for initial management of plasma uric acid levels in pediatric and adult patients with leukemia, lymphoma, and solid tumor malignancies who are receiving anti-cancer therapy expected to result in tumor lysis and subsequent elevation of plasma uric acid. Elitek® has a half-life of 16-21 hours in humans and must be dosed daily via IV infusion. Similar to Krystexxa®, Elitek® also has a black-box warning for anaphylaxis and hemolysis (especially in patients with a G6PD deficiency). Dosing frequency (daily), route of administration (IV), immunogenicity, and cost make Elitek® an unlikely option for chronic gout treatment.

In view of the foregoing, there is a need in the art to develop safer, more convenient, and less immunogenic options for treating hyperuricemia. The invention described herein fulfills this need.

SUMMARY

To overcome the significant and known side-effects of prior art treatments, the potential of a plurality of uricase sequences has been evaluated and specific and meaningful improvements in those sequences have been made to arrive at improved uricases that are safer, less immunogenic, and more convenient than existing therapies.

In some aspects, a number of different uricase sequences are encompassed herein. A uricase may comprise an amino acid sequence that is at least about 90%, 91%, 92%, 93%, 94%, 95%, 96%, 97%, 98%, or 99% identical to any one of SEQ ID NOS: 1-34, wherein the sequence is not any one of SEQ ID NOS: 27-33.

In some embodiments, the uricase is at least about 90%, 91%, 92%, 93%, 94%, 95%, 96%, 97%, 98%, or 99% identical to SEQ ID NO: 1 or at least about 90%, 91%, 92%, 93%, 94%, 95%, 96%, 97%, 98%, or 99% identical to SEQ ID NO: 2.

In some embodiments, the uricase is a sequence that differs from any one of SEQ ID NOS: 1-34 by from about 1 to about 35 amino acids (e.g., by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids). For example, the uricase may differ from SEQ ID NO: 1 or SEQ ID NO: 2 by from about 1 to about 35 amino acids.

In some aspects, the uricase is a sequence that differs from any one of SEQ ID NOS: 1-34 by from about 1 to about 14 amino acids (e.g., by about 1, 2, 3, 4, 5, 6, 7, 8, 9, 10, 11, 12, 13, or 14 amino acids). For example, the uricase may differ from SEQ ID NO: 1 or SEQ ID NO: 2 by from about 1 to about 14 amino acids. In certain aspects, the uricase is SEQ ID NO: 1 or SEQ ID NO: 2. In certain embodiments, the uricase is any one of SEQ ID NOS: 3-26 or 34.

In accordance with the description, methods of treatment are also provided for hyperuricemia, gout (including various forms of gout), and tumor lysis syndrome.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 6 is a bar graph that depicts the HLA-DRB1 frequencies in the study (donor) population as compared to those found in the Caucasian population.

FIGS. 7A-C provide individual donor data for ex vivo immunogenicity assessments. FIG. 7A is a scatter plot that depicts the stimulation index of the buffer (negative control) as compared to KLH (positive control). FIG. 7B is a scatter plot that depicts the stimulation index of the buffer (negative control) as compared to the uricase that was tested. FIG. 7C is a bar graph that depicts the mean stimulation index (SI) for the buffer, KLH, and uricase.

FIG. 8A is an SDS-PAGE analysis of 3 N-terminal truncated uricase variants (V1, V2, and V3), as compared to SGD uricase. FIG. 8B is a line graph that depicts the results of uricase activity assays at a variety of substrate (UA) concentrations. The solid lines depict a Michaelis-Menten kinetic fit.

FIG. 9A depicts the results of uricase activity assays done in the presence of DTT for di-Cys and tri-Cys uricases (no PEG). FIG. 9B depicts the results of uricase activity assays for di-PEGylated and tri-PEGylated uricases.

FIG. 10A shows the three dimensional solvent accessible sites within the tetrameric crystal structure of *Arthrobacter globiformis* uricase (PDB accession code: 2YZB). FIG. 10B is an SDS-PAGE analysis of non-pegylated and di-pegylated uricase. FIG. 10C is a reverse-phase chromatography analysis of purified di-pegylated uricase. FIG. 10D is a line graph that depicts the results of uricase activity assays at a variety of substrate (UA) concentrations. The solid and dashed lines depict a Michaelis-Menten kinetic fit.

FIGS. 11A-B are graphs that depict pharmacokinetic data for PEGylated uricase. FIG. 11A depicts rat pharmacokinetic data for di-PEGylated and tri-PEGylated uricase. FIG. 11B depicts dog pharmacokinetic data for di-PEGylated uricase.

FIG. 12A show the comparison of di-PEGylated uricase activity and Krystexxa® in 50% human serum at 37° C. FIG. 12B depicts the activity of di-PEGylated uricase that has been incubated in human serum at 37° C. for various lengths of time. FIG. 12C depicts the activity of di-PEGylated uricase in response to repeated doses of UA.

FIGS. 14A-B depict response surface plots demonstrating the effect of reagent concentration on overall PEGylation efficiency for time points from 10 minutes to 2 hours. FIG. 14A illustrates the data based on an analysis of "fully PEGylated subunit" (i.e. 3 out of 3 functionalized conjugation sites per monomer) as directly obtained from the RP-HPLC assay trace. FIG. 14B illustrates the data analysis when the overall derivatization is computed based on equation (1).

DESCRIPTION OF THE SEQUENCES

Figure 1:
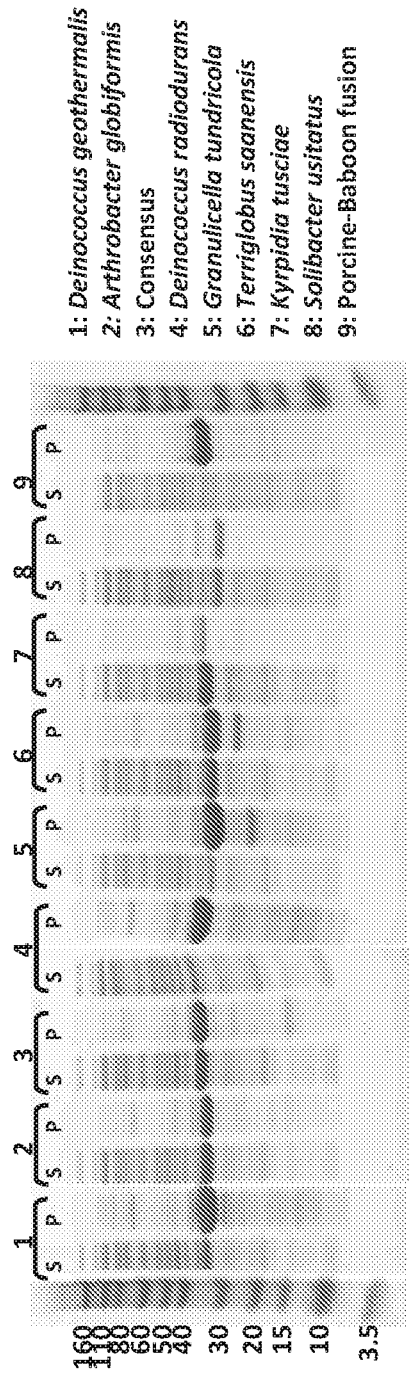
FIG. 1 depicts an SDS-PAGE analysis of the soluble (S) and insoluble (P) proteins present in the cell lysates of *E. coli* cells expressing various uricases.

Table 1 provides a listing of certain sequences referenced herein.

TABLE 1

Description of the Sequences

| Description | Sequences | SEQ ID NO |
|---|---|---|
| Modified *Arthrobacter globiformis* Uricase, modified N-terminus, SGD, 2-Cys, C-terminal truncation (SGD V1 C2) | MATAETSTGCKVVLGQNQYGKAEVRLVKVTRCTARHEIQDLNVTSQLSGDFEAAHTAGDNAHVVA TDTQKNTVYAFARDGFATTEEFLLRLGKHFTEGFDWVTGGRWAAQQFFWDRINDHDHAFSRNKSE VRTAVLEISGSEQAIVAGIEGLTVLKSTGSEFHGFPRDKYTTLQETTDRILATDVSARWRYNTVE VDFDAVYASVRGLLLKAFAETHSLALQQTMYEMGRAVIETHPEIDEIKMSLPNKHHFLVDLQPFG QDNPNEVFYAADRPYGLIEATIQREGSRAD | 1 |
| Modified *Arthrobacter globiformis* Uricase, modified N-terminus, RGD, 2-Cys, C-terminal truncation (RGD V1 C2) | MATAETSTGCKVVLGQNQYGKAEVRLVKVTRCTARHEIQDLNVTSQLRGDFEAAHTAGDNAHVVA TDTQKNTVYAFARDGFATTEEFLLRLGKHFTEGFDWVTGGRWAAQQFFWDRINDHDHAFSRNKSE VRTAVLEISGSEQAIVAGIEGLTVLKSTGSEFHGFPRDKYTTLQETTDRILATDVSARWRYNTVE VDFDAVYASVRGLLLKAFAETHSLALQQTMYEMGRAVIETHPEIDEIKMSLPNKHHFLVDLQPFG QDNPNEVFYAADRPYGLIEATIQREGSRAD | 2 |
| Modified *Arthrobacter globiformis* Uricase, modified N-terminus, RGD variants, 2-Cys, C-terminal truncation | MATAETSTGCKVVLGQNQYGKAEVRLVKVTRCTARHEIQDLNVTSQLXaa$_1$Xaa$_2$Xaa$_3$FEAAHTA GDNAHVVATDTQKNTVYAFARDGFATTEEFLLRLGKHFTEGFDWVTGGRWAAQQFFWDRINDHDH AFSRNKSEVRTAVLEISGSEQAIVAGIEGLTVLKSTGSEFHGFPRDKYTTLQETTDRILATDVSA RWRYNTVEVDFDAVYASVRGLLLKAFAETHSLALQQTMYEMGRAVIETHPEIDEIKMSLPNKHHF LVDLQPFGQDNPNEVFYAADRPYGLIEATIQREGSRAD | 3 |

TABLE 1-continued

Description of the Sequences

| Description | Sequences | SEQ ID NO |
|---|---|---|
| (RGD variants of V1 C2) | wherein<br>Xaa$_1$ is either R or any natural amino acid except C;<br>Xaa$_2$ is either G or any natural amino acid except C<br>Xaa$_3$ is either D or any natural amino acid except C. | |
| Genus sequence, with optional N-terminal modification, 4 possible cysteines, R/SGD, optionally with or without C-terminal truncation in lowercase letters | MXaa$_1$ATAETSTGXaa$_2$KVVLGQNQYGKAEVRLVKVTRXaa$_3$TARHEIQDLNVTSQLXaa$_4$GDFEA<br>AHTAGDNAHVVATDTQKNTVYAFARDGFATTEEFLLRLGKHFTEGFDWVTGGRWAAQQFFWDRI<br>Xaa$_5$DHDHAFSRNKSEVRTAVLEISGXaa$_6$EQAIVAGIEGLTVLKSTGSEFHGFPRDKYTTLQETT<br>DRILATDVSARWRYNTVEVDFDAVYASVRGLLLKAFAETHSLALQQTMYEMGRAVIETHPEIDEI<br>KMSLPNKHHFLVDLQPFGQDNPNEVFYAADRPYGLIEATIQREGSRADhpiwsniagf<br>wherein<br>Xaa$_1$ is either present or absent, and if present is T;<br>Xaa$_2$ is either T or C;<br>Xaa$_3$ is either N or C;<br>Xaa$_4$ is either R or S;<br>Xaa$_5$ is either N or C;<br>Xaa$_6$ is either S or C;<br>and wherein from at least one, two, three, or four cysteines are included in the sequence and wherein one or more lowercase amino acids in the C-terminus (hpiwsniagf) are optional. | 4 |
| Genus sequence, with modified N-terminus, with 4 possible cysteines, SGD, optionally with or without C-terminal truncation in lowercase letters | MATAETSTGXaa$_1$KVVLGQNQYGKAEVRLVKVTRXaa$_2$TARHEIQDLNVTSQLSGDFEAAHTAGDN<br>AHVVATDTQKNTVYAFARDGFATTEEFLLRLGKHFTEGFDWVTGGRWAAQQFFWDRIXaa$_3$DHDH<br>AFSRNKSEVRTAVLEISGXaa$_4$EQAIVAGIEGLTVLKSTGSEFHGFPRDKYTTLQETTDRILATD<br>VSARWRYNTVEVDFDAVYASVRGLLLKAFAETHSLALQQTMYEMGRAVIETHPEIDEIKMSLPNK<br>HHFLVDLQPFGQDNPNEVFYAADRPYGLIEATIQREGSRADhpiwsniagf<br>wherein<br>Xaa$_1$ is either T or C;<br>Xaa$_2$ is either N or C;<br>Xaa$_3$ is either N or C;<br>Xaa$_4$ is either S or C;<br>and wherein from at least one, two, three, or four cysteines are included in the sequence and wherein one or more lowercase amino acids in the C-terminus (hpiwsniagf) are optional. | 5 |
| Genus sequence, with truncated N-terminus, 4 possible cysteines, SGD, optionally with or without C-terminal truncation in lowercase letters | MXaa$_1$KVVLGQNQYGKAEVRLVKVTRXaa$_2$TARHEIQDLNVTSQLSGDFEAAHTAGDNAHVVATDT<br>QKNTVYAFARDGFATTEEFLLRLGKHFTEGFDWVTGGRWAAQQFFWDRIXaa$_3$DHDHAFSRNKSE<br>VRTAVLEISGXaa$_4$EQAIVAGIEGLTVLKSTGSEFHGFPRDKYTTLQETTDRILATDVSARWRYN<br>TVEVDFDAVYASVRGLLLKAFAETHSLALQQTMYEMGRAVIETHPEIDEIKMSLPNKHHFLVDLQ<br>PFGQDNPNEVFYAADRPYGLIEATIQREGSRADhpiwsniagf<br>wherein<br>Xaa$_1$ is either T or C;<br>Xaa$_2$ is either N or C;<br>Xaa$_3$ is either N or C;<br>Xaa$_4$ is either S or C;<br>and wherein from at least one, two, three, or four cysteines are included in the sequence and wherein one or more lowercase amino acids in the C-terminus (hpiwsniagf) are optional. | 6 |
| Genus sequence, with optional N-terminal modification, 9 possible cysteines, R/SGD, optionally with or without C-terminal truncation in lowercase letters | MXaa$_1$ATAETSTGXaa$_2$KVVLGQNQYGKAEVRLVKVTRXaa$_3$TARHEIQDLNVTSQLXaa$_4$GDFEA<br>AHTAGDNAHVVATDTQKNTVYAFARDGFATTEEFLLRLGKHFTEGFDWVTGGRWAAQQFFWDRI<br>Xaa$_5$Xaa$_6$HDHAFSRNKSEVRTAVLEISGXaa$_7$EQAIVAGIEGLTVLKSTGSEFHGFPRDKYTTLQ<br>ETTDRILATDVSARWRYNTVXaa$_8$VDFDAVYASVRGLLLKAFAETHSLALQQTMYEMGRAVIETH<br>Xaa$_9$EIDEIKMSLPNKHHELVDLQPFGQDNPNEVFYAADRPYGLIEATIQRXaa$_{10}$GSXaa$_{11}$ADhp<br>iwsniagf<br>wherein<br>Xaa$_1$ is either present or absent, and if present is T;<br>Xaa$_2$ is either T or C;<br>Xaa$_3$ is either N or C;<br>Xaa$_4$ is either R or S;<br>Xaa$_5$ is either N or C;<br>Xaa$_6$ is either D or C;<br>Xaa$_7$ is either S or C;<br>Xaa$_8$ is either E or C;<br>Xaa$_9$ is either P or C;<br>Xaa$_{10}$ is either E or C;<br>Xaa$_{11}$ is either R or C;<br>and wherein from at least one, two, three, or four cysteines are included in the sequence and wherein one or more lowercase amino acids in the C-terminus (hpiwsniagf) are optional. | 7 |

TABLE 1-continued

Description of the Sequences

| Description | Sequences | SEQ ID NO |
|---|---|---|
| Genus sequence, with optional N-terminal modification, 9 possible cysteines, XGD, optionally with or without C-terminal truncation in lowercase letters | MXaa$_1$ATAETSTGXaa$_2$KVVLGQNQYGKAEVRLVKVTRXaa$_3$TARHEIQDLNVTSQLXaa$_4$GDFEA AHTAGDNAHVVATDTQKNTVYAFARDGFATTEEFLLRLGKHFTEGFDWVTGGRWAAQQFFWDRI Xaa$_5$Xaa$_6$HDHAFSRNKSEVRTAVLEISGXaa$_7$EQAIVAGIEGLTVLKSTGSEFHGFPRDKYTTLQ ETTDRILATDVSARWRYNTVXaa$_8$VDFDAVYASVRGLLLKAFAETHSLALQQTMYEMGRAVIETH Xaa$_9$EIDEIKMSLPNKHHFLVDLQPFGQDNPNEVFYAADRPYGLIEATIQRXaa$_{10}$GSXaa$_{11}$ADhp iwsniagf<br>wherein<br>Xaa$_1$ is either present or absent, and if present is T;<br>Xaa$_2$ is either T or C;<br>Xaa$_3$ is either N or C;<br>Xaa$_4$ is any naturally occurring amino acid except C;<br>Xaa$_5$ is either N or C;<br>Xaa$_6$ is either D or C;<br>Xaa$_7$ is either S or C;<br>Xaa$_8$ is either E or C;<br>Xaa$_9$ is either P or C;<br>Xaa$_{10}$ is either E or C;<br>Xaa$_{11}$ is either R or C;<br>and wherein from at least one, two, three, or four cysteines are included in the sequence and wherein one or more lowercase amino acids in the C-terminus (hpiwsniagf) are optional. | 8 |
| Genus sequence, with N-terminal truncation, 9 possible cysteines, XGD, optionally with or without C-terminal truncation in lowercase letters | MXaa$_1$KVVLGQNQYGKAEVRLVKVTRXaa$_2$TARHEIQDLNVTSQLXaa$_3$GDFEAAHTAGDNAHVVA TDTQKNTVYAFARDGFATTEEFLLRLGKHFTEGFDWVTGGRWAAQQFFWDRI Xaa$_4$Xaa$_5$HDHAFSRNKSEVRTAVLEISGXaa$_6$EQAIVAGIEGLTVLKSTGSEFHGFPRDKYTTLQ ETTDRILATDVSARWRYNTVXaa$_7$VDFDAVYASVRGLLLKAFAETHSLALQQTMYEMGRAVIETH Xaa$_8$EIDEIKMSLPNKHHFLVDLQPFGQDNPNEVFYAADRPYGLIEATIQRXaa$_9$GSXaa$_{10}$ADhp iwsniagf<br>wherein<br>Xaa$_1$ is either T or C;<br>Xaa$_2$ is either N or C;<br>Xaa$_3$ is any naturally occurring amino acid except C;<br>Xaa$_4$ is either N or C;<br>Xaa$_5$ is either D or C;<br>Xaa$_6$ is either S or C;<br>Xaa$_7$ is either E or C;<br>Xaa$_8$ is either P or C;<br>Xaa$_9$ is either E or C;<br>Xaa$_{10}$ is either R or C;<br>and wherein from at least one, two, three, or four cysteines are included in the sequence and wherein one or more lowercase amino acids in the C-terminus (hpiwsniagf) are optional. | 9 |
| Genus sequence, with optional N-terminal modification, 9 possible conjugation sites, XGD, optionally with or without C-terminal truncation in lowercase letters | MXaa$_1$ATAETSTGXaa$_2$KVVLGQNQYGKAEVRLVKVTRXaa$_3$TARHEIQDLNVTSQLXaa$_4$GDFEA AHTAGDNAHVVATDTQKNTVYAFARDGFATTEEFLLRLGKHFTEGFDWVTGGRWAAQQFFWDRI Xaa$_5$Xaa$_6$HDHAFSRNKSEVRTAVLEISGXaa$_7$EQAIVAGIEGLTVLKSTGSEFHGFPRDKYTTLQ ETTDRILATDVSARWRYNTVXaa$_8$VDFDAVYASVRGLLLKAFAETHSLALQQTMYEMGRAVIETH Xaa$_9$EIDEIKMSLPNKHHFLVDLQPFGQDNPNEVFYAADRPYGLIEATIQRXaa$_{10}$SXaa$_{11}$ADhp iwsniagf<br>wherein<br>Xaa$_1$ is either present or absent, and if present is T;<br>Xaa$_2$ is either T or any natural or unnatural amino acid used for site-specific conjugation;<br>Xaa$_3$ is either N or any natural or unnatural amino acid used for site-specific conjugation;<br>Xaa$_4$ is any naturally occurring amino acid except C;<br>Xaa$_5$ is either N or any natural or unnatural amino acid used for site-specific conjugation;<br>Xaa$_6$ is either D or any natural or unnatural amino acid used for site-specific conjugation;<br>Xaa$_7$ is either S or any natural or unnatural amino acid used for site-specific conjugation;<br>Xaa$_8$ is either E or any natural or unnatural amino acid used for site-specific conjugation;<br>Xaa$_9$ is either P or any natural or unnatural amino acid used for site-specific conjugation;<br>Xaa$_{10}$ is either E or any natural or unnatural amino acid used for site-specific conjugation;<br>Xaa$_{11}$ is either R or any natural or unnatural amino acid used for site-specific conjugation;<br>and wherein from at least one, two, three, or four cysteines are included in the sequence and wherein one or more lowercase amino acids in the C-terminus (hpiwsniagf) are optional. | 10 |

TABLE 1-continued

Description of the Sequences

| Description | Sequences | SEQ ID NO |
|---|---|---|
| Genus sequence, with N-terminal truncation, 9 possible conjugation sites, XGD, optionally with or without C-terminal truncation in lowercase letters | MXaa$_1$KVVLGQNQYGKAEVRLVKVTRXaa$_2$TARHEIQDLNVTSQLXaa$_3$GDFEAAHTAGDNAHVVA TDTQKNTVYAFARDGFATTEEFLLRLGKHFTEGFDWVTGGRWAAQQFFWDRI Xaa$_4$Xaa$_5$HDHAFSRNKSEVRTAVLEISGXaa$_6$EQAIVAGIEGLTVLKSTGSEFHGFPRDKYTTLQ ETTDRILATDVSARWRYNTVXaa$_7$VDFDAVYASVRGLLLKAFAETHSLALQQTMYEMGRAVIETH Xaa$_8$EIDEIKMSLPNKHHFLVDLQPFGQDNPNEVFYAADRPYGLIEATIQRXaa$_9$GSXaa$_{10}$ADhp iwsniagf<br>wherein<br>Xaa$_1$ is either T or any natural or unnatural amino acid used for site-specific conjugation;<br>Xaa$_2$ is either N or any natural or unnatural amino acid used for site-specific conjugation;<br>Xaa$_3$ is any naturally occurring amino acid except C;<br>Xaa$_4$ is either N or any natural or unnatural amino acid used for site-specific conjugation;<br>Xaa$_5$ is either D or any natural or unnatural amino acid used for site-specific conjugation;<br>Xaa$_6$ is either S or any natural or unnatural amino acid used for site-specific conjugation;<br>Xaa$_7$ is either E or any natural or unnatural amino acid used for site-specific conjugation;<br>Xaa$_8$ is either P or any natural or unnatural amino acid used for site-specific conjugation;<br>Xaa$_9$ is either E or any natural or unnatural amino acid used for site-specific conjugation;<br>Xaa$_{10}$ is either R or any natural or unnatural amino acid used for site-specific conjugation;<br>and wherein from at least one, two, three, or four cysteines are included in the sequence and wherein one or more lowercase amino acids in the C-terminus (hpiwsniagf) are optional. | 11 |
| Modified *Arthrobacter globiformis* Uricase C1 construct (T11C mutation, SGD, optional N-terminal His tag and optional short linker, both in lowercase (first Uricase residue corresponds to Thr2)) | mgshhhhhhgarqTATAETSTGCKVVLGQNQYGKAEVRLVKVTRNTARHEIQDLNVTSQLSGDFE AAHTAGDNAHVVATDTQKNTVYAFARDGFATTEEFLLRLGKHFTEGFDWVTGGRWAAQQFFWDRI NDHDHAFSRNKSEVRTAVLEISGSEQAIVAGIEGLTVLKSTGSEFHGFPRDKYTTLQETTDRILA TDVSARWRYNTVEVDFDAVYASVRGLLLKAFAETHSLALQQTMYEMGRAVIETHPEIDEIKMSLP NKHHFLVDLQPFGQDNPNEVFYAADRPYGLIEATIQREGSRAD | 12 |
| Modified *Arthrobacter globiformis* Uricase C1 construct (variant 1), with tag eliminated, deletion of Thr2 (to avoid partial N-term Met cleavage) and Cys at position 11 (in another embodiment, SGD may be RGD) | MATAETSTGCKVVLGQNQYGKAEVRLVKVTRNTARHEIQDLNVTSQLSGDFEAAHTAGDNAHVVA TDTQKNTVYAFARDGFATTEEFLLRLGKHFTEGFDWVTGGRWAAQQFFWDRINDHDHAFSRNKSE VRTAVLEISGSEQAIVAGIEGLTVLKSTGSEFHGFPRDKYTTLQETTDRILATDVSARWRYNTVE VDFDAVYASVRGLLLKAFAETHSLALQQTMYEMGRAVIETHPEIDEIKMSLPNKHHFLVDLQPFG QDNPNEVFYAADRPYGLIEATIQREGSRAD | 13 |
| Modified *Arthrobacter globiformis* Uricase C1 construct (variant 2 - N-term truncation) with tag eliminated, deletion of Thr2-Ala5 and Cys at position 11, expect complete retention of N-term Met (in another embodiment, SGD may be RGD) | METSTGCKVVLGQNQYGKAEVRLVKVTRNTARHEIQDLNVTSQLSGDFEAAHTAGDNAHVVATDT QKNTVYAFARDGFATTEEFLLRLGKHFTEGFDWVTGGRWAAQQFFWDRINDHDHAFSRNKSEVRT AVLEISGSEQAIVAGIEGLTVLKSTGSEFHGFPRDKYTTLQETTDRILATDVSARWRYNTVEVDF DAVYASVRGLLLKAFAETHSLALQQTMYEMGRAVIETHPEIDEIKMSLPNKHHFLVDLQPFGQDN PNEVFYAADRPYGLIEATIQREGSRAD | 14 |
| Modified *Arthrobacter globiformis* Uricase C1 construct (variant 3 - N-term truncation) with tag eliminated, deletion of Thr2-Thr9, Cys at position 11, expect processing of N-term met (in another embodiment, SGD may be RGD) | MGCKVVLGQNQYGKAEVRLVKVTRNTARHEIQDLNVTSQLSGDFEAAHTAGDNAHVVATDTQKNT VYAFARDGFATTEEFLLRLGKHFTEGFDWVTGGRWAAQQFFWDRINDHDHAFSRNKSEVRTAVLE ISGSEQAIVAGIEGLTVLKSTGSEFHGFPRDKYTTLQETTDRILATDVSARWRYNTVEVDFDAVY ASVRGLLLKAFAETHSLALQQTMYEMGRAVIETHPEIDEIKMSLPNKHHFLVDLQPFGQDNPNEV FYAADRPYGLIEATIQREGSRAD | 15 |

TABLE 1-continued

Description of the Sequences

| Description | Sequences | SEQ ID NO |
|---|---|---|
| Modified *Arthrobacter globiformis* Uricase with SGD, and PEGylation available sites at T11C, N33C, S142C, optional N-terminal His tag and optional short linker, both in lowercase (in another embodiment an additional PEGylation site may optionally be placed at N119C (not shown here and/or SGD may be RGD) | mgshhhhhhgarqTATAETSTGCKVVLGQNQYGKAEVRLVKVTRCTARHEIQDLNVTSQLSGDFE AAHTAGDNAHVVATDTQKNTVYAFARDGFATTEEFLLRLGKHFTEGFDWVTGGRWAAQQFFWDRI NDHDHAFSRNKSEVRTAVLEISGCEQAIVAGIEGLTVLKSTGSEFHGFPRDKYTTLQETTDRILA TDVSARWRYNTVEVDFDAVYASVRGLLLKAFAETHSLALQQTMYEMGRAVIETHPEIDEIKMSLP NKHHFLVDLQPFGQDNPNEVFYAADRPYGLIEATIQREGSRAD | 16 |
| Modified *Arthrobacter globiformis* Uricase, NH2-terminal truncated, SGD, PEGylation available sites at T11C and N33C 2-Cys (SGD His C2) with optional N-terminal His tag and optional short linker, both in lowercase (in another embodiment, SGD may be RGD) | mgshhhhhhgarqTATAETSTGCKVVLGQNQYGKAEVRLVKVTRCTARHEIQDLNVTSQLSGDFE AAHTAGDNAHVVATDTQKNTVYAFARDGFATTEEFLLRLGKHFTEGFDWVTGGRWAAQQFFWDRI NDHDHAFSRNKSEVRTAVLEISGSEQAIVAGIEGLTVLKSTGSEFHGFPRDKYTTLQETTDRILA TDVSARWRYNTVEVDFDAVYASVRGLLLKAFAETHSLALQQTMYEMGRAVIETHPEIDEIKMSLP NKHHFLVDLQPFGQDNPNEVFYAADRPYGLIEATIQREGSRAD | 17 |
| Modified *Arthrobacter globiformis* Uricase (C-term truncation with SGD)(in another embodiment, SGD may be RGD) | MATAETSTGTKVVLGQNQYGKAEVRLVKVTRNTARHEIQDLNVTSQLSGDFEAAHTAGDNAHVVA TDTQKNTVYAFARDGFATTEEFLLRLGKHFTEGFDWVTGGRWAAQQFFWDRINDHDHAFSRNKSE VRTAVLEISGSEQAIVAGIEGLTVLKSTGSEFHGFPRDKYTTLQETTDRILATDVSARWRYNTVE VDFDAVYASVRGLLLKAFAETHSLALQQTMYEMGRAVIETHPEIDEIKMSLPNKHHFLVDLQPFG QDNPNEVFYAADRPYGLIEATIQREGSRAD | 18 |
| Modified *Arthrobacter globiformis* Uricase (processed form - Met cleaved at N-term., SGD, and C-term truncation) (in another embodiment, SGD may be RGD) | ATAETSTGTKVVLGQNQYGKAEVRLVKVTRNTARHEIQDLNVTSQLSGDFEAAHTAGDNAHVVAT DTQKNTVYAFARDGFATTEEFLLRLGKHFTEGFDWVTGGRWAAQQFFWDRINDHDHAFSRNKSEV RTAVLEISGSEQAIVAGIEGLTVLKSTGSEFHGFPRDKYTTLQETTDRILATDVSARWRYNTVEV DFDAVYASVRGLLLKAFAETHSLALQQTMYEMGRAVIETHPEIDEIKMSLPNKHHFLVDLQPFGQ DNPNEVFYAADRPYGLIEATIQREGSRAD | 19 |
| Modified *Arthrobacter globiformis* Uricase (contains optional N-terminal His tag and optional short linker, both in lowercase; contains SGD instead of RGD) (C-term truncation with his tag and SGD) | mgshhhhhhgarqTATAETSTGTKVVLGQNQYGKAEVRLVKVTRNTARHEIQDLNVTSQLSGDFE AAHTAGDNAHVVATDTQKNTVYAFARDGFATTEEFLLRLGKHFTEGFDWVTGGRWAAQQFFWDRI NDHDHAFSRNKSEVRTAVLEISGSEQAIVAGIEGLTVLKSTGSEFHGFPRDKYTTLQETTDRILA TDVSARWRYNTVEVDFDAVYASVRGLLLKAFAETHSLALQQTMYEMGRAVIETHPEIDEIKMSLP NKHHFLVDLQPFGQDNPNEVFYAADRPYGLIEATIQREGSRAD | 20 |
| Modified *Arthrobacter globiformis* Uricase (contains optional N-terminal His tag and optional short linker, both in lowercase) (C-term truncation with his tag) | mgshhhhhhgarqTATAETSTGTKVVLGQNQYGKAEVRLVKVTRNTARHEIQDLNVTSQLRGDFE AAHTAGDNAHVVATDTQKNTVYAFARDGFATTEEFLLRLGKHFTEGFDWVTGGRWAAQQFFWDRI NDHDHAFSRNKSEVRTAVLEISGSEQAIVAGIEGLTVLKSTGSEFHGFPRDKYTTLQETTDRILA TDVSARWRYNTVEVDFDAVYASVRGLLLKAFAETHSLALQQTMYEMGRAVIETHPEIDEIKMSLP NKHHFLVDLQPFGQDNPNEVFYAADRPYGLIEATIQREGSRAD | 21 |
| Modified *Arthrobacter globiformis* Uricase (0 cysteines) (truncated the C-terminal 11 amino acids to eliminate the Cys) (C-term truncation) (in another embodiment, RGD may be SGD) | MTATAETSTGTKVVLGQNQYGKAEVRLVKVTRNTARHEIQDLNVTSQLRGDFEAAHTAGDNAHVV ATDTQKNTVYAFARDGFATTEEFLLRLGKHFTEGFDWVTGGRWAAQQFFWDRINDHDHAFSRNKS EVRTAVLEISGSEQAIVAGIEGLTVLKSTGSEFHGFPRDKYTTLQETTDRILATDVSARWRYNTV EVDFDAVYASVRGLLLKAFAETHSLALQQTMYEMGRAVIETHPEIDEIKMSLPNKHHFLVDLQPF GQDNPNEVFYAADRPYGLIEATIQREGSRAD | 22 |

TABLE 1-continued

Description of the Sequences

| Description | Sequences | SEQ ID NO |
|---|---|---|
| Modified *Arthrobacter globiformis* Uricase (0 cysteines)(RGD variants, truncated the C-terminal 11 amino acids to eliminate the Cys)(C-term truncation)(in another embodiment, RGD may be SGD) | MTATAETSTGTKVVLGQNQYGKAEVRLVKVTRNTARHEIQDLNVTSQLXaa$_1$Xaa$_2$Xaa$_3$FEAAHT AGDNAHVVATDTQKNTVYAFARDGFATTEEFLLRLGKHFTEGFDWVTGGRWAAQQFFWDRINDHD HAFSRNKSEVRTAVLEISGSEQAIVAGIEGLTVLKSTGSEFHGFPRDKYTTLQETTDRILATDVS ARWRYNTVEVDFDAVYASVRGLLLKAFAETHSLALQQTMYEMGRAVIETHPEIDEIKMSLPNKHH FLVDLQPFGQDNPNEVFYAADRPYGLIEATIQREGSRAD<br>wherein<br>Xaa$_1$ is either R or any natural amino acid except C;<br>Xaa$_2$ is either G or any natural amino acid except C<br>Xaa$_3$ is either D or any natural amino acid except C. | 23 |
| Modified *Arthrobacter globiformis* Uricase (0 cysteines)(truncated the C-terminal aa to eliminate the cysteine) | MTATAETSTGTKVVLGQNQYGKAEVRLVKVTRNTARHEIQDLNVTSQLRGDFEAAHTAGDNAHVV ATDTQKNTVYAFARDGFATTEEFLLRLGKHFTEGFDWVTGGRWAAQQFFWDRINDHDHAFSRNKS EVRTAVLEISGSEQAIVAGIEGLTVLKSTGSEFHGFPRDKYTTLQETTDRILATDVSARWRYNTV EVDFDAVYASVRGLLLKAFAETHSLALQQTMYEMGRAVIETHPEIDEIKMSLPNKHHFLVDLQPF GQDNPNEVFYAADRPYGLIEATIQREGSRADHPIWSNIAGF | 24 |
| Modified *Arthrobacter globiformis* Uricase (0 cysteines)(RGD variants, truncated the C-terminal aa to eliminate the cysteine) | MTATAETSTGTKVVLGQNQYGKAEVRLVKVTRNTARHEIQDLNVISQLXaa$_1$Xaa$_2$Xaa$_3$FEAAHT AGDNAHVVATDTQKNTVYAFARDGFATTEEFLLRLGKHFTEGFDWVTGGRWAAQQFFWDRINDHD HAFSRNKSEVRTAVLEISGSEQAIVAGIEGLTVLKSTGSEFHGFPRDKYTTLQETTDRILATDVS ARWRYNTVEVDFDAVYASVRGLLLKAFAETHSLALQQTMYEMGRAVIETHPEIDEIKMSLPNKHH FLVDLQPFGQDNPNEVFYAADRPYGLIEATIQREGSRADHPIWSNIAGF<br>wherein<br>Xaa$_1$ is either R or any natural amino acid except C;<br>Xaa$_2$ is either G or any natural amino acid except C<br>Xaa$_3$ is either D or any natural amino acid except C. | 25 |
| Modified *Arthrobacter globiformis* Uricase (RGD variants)(contains the C-terminal 11 amino acids) | MTATAETSTGTKVVLGQNQYGKAEVRLVKVTRNTARHEIQDLNVTSQLXaa$_1$Xaa$_2$Xaa$_3$FEAAHT AGDNAHVVATDTQKNTVYAFARDGFATTEEFLLRLGKHFTEGFDWVTGGRWAAQQFFWDRINDHD HAFSRNKSEVRTAVLEISGSEQAIVAGIEGLTVLKSTGSEFHGFPRDKYTTLQETTDRILATDVS ARWRYNTVEVDFDAVYASVRGLLLKAFAETHSLALQQTMYEMGRAVIETHPEIDEIKMSLPNKHH FLVDLQPFGQDNPNEVFYAADRPYGLIEATIQREGSRADHPIWSNIAGFC<br>wherein<br>Xaa$_1$ is either R or any natural amino acid;<br>Xaa$_2$ is either G or any natural amino acid<br>Xaa$_3$ is either D or any natural amino acid. | 26 |
| *Arthrobacter globiformis* Uricase (wt)(contains the C-terminal 11 amino acids)(in another embodiment, RGD may be SGD) | MTATAETSTGTKVVLGQNQYGKAEVRLVKVTRNTARHEIQDLNVTSQLRGDFEAAHTAGDNAHVV ATDTQKNTVYAFARDGFATTEEFLLRLGKHFTEGFDWVTGGRWAAQQFFWDRINDHDHAFSRNKS EVRTAVLEISGSEQAIVAGIEGLTVLKSTGSEFHGFPRDKYTTLQETTDRILATDVSARWRYNTV EVDFDAVYASVRGLLLKAFAETHSLALQQTMYEMGRAVIETHPEIDEIKMSLPNKHHFLVDLQPF GQDNPNEVFYAADRPYGLIEATIQREGSRADHPIWSNIAGFC | 27 |
| *Deinococcus geothermalis* Uricase 1 cysteine, gram-positive, thermophilic radiophile | MTQTQQNQQPKVKARLGANNYGKAEVNLMKVKRDSERHEIRELQVRVALIGDFAAAHEQGDNTDL LATDTVRNTIYGLAKEGFQASPEAFGKELISHFVTTGPKVTGGFMEFTEYLWERIQVGGEGHNHA FVRQMPQRTGRVESEDGKTFKITSGLQNLYVLKTTESGWANYLLNERFTTLPETHERLMASFVTA KWEYNEDQVDYDDVWPRVYRQLQETFTDHYSPSLQRTLFLMGQAVLTRCPEMSRIWLQMPNKHHL QYNLERFGLDNNLEIFHVDPEPYGLMEAWVERA | 28 |
| *Deinococcus radiodurans* Uricase (2 cysteines), is an extremophilic bacterium | MMTGTQQPGTQPKVKVRLGENNYGKAEVQLMKIKRGTPRHELREAKVRVAMYGDFGAAHSEGDNT DLVATDTVRNTVYGLAKEGFESSIEEFGKELLTHFVKVGPRVTGGFAEFTEHLWERVQTPAQPQG HDHAFVRQMPKRTARVETQDGRRFTVTSGIEELYVLKTTESGWENYLLDERFTTLPETHDRVMAT FVTAKWEYAVESCDYDAVWERVYRQIQHTFTDHYSPSLQRTLYLM GEAVLSVCPEISRIWFQMPNKHHLVYNLGRFGLENNNEILHVDPEPYGLMEAWVERAE | 29 |
| *Granulicella tundricola* Uricase (1 cysteine) | MAELTDAKFEIVANRYGKSKVRLLKVTRAEGRSDVHEWTVQVLLRGDFETAHTVGDNSKIVTTDT MKNTVYSLARWSSATTMEEFAEELIEHLLRRNEQVSSVRVHIEAALWKRLTVDGKEHPDTFMRGS NEVQTATVEQARAGEKKFIAGFANLQLLKTANSAFSGFQRDELTTLPETRDRVFGTAVDAKWTYS GPVEFAAMRKAAREVMLKVFADHMSESVQHTLYAMADAALEAVAEITEIELAMPNKHCLLVDLSK FGQDNPNQIFVPTDEPHGYIEARVRRK | 30 |
| Acidic Bacteria *Solibacter usitatus* Uricase (6 cysteines) | MERFASGWKQNYYGKGDVIVYRLNRDGVVPQGCCPVFGANVKMLLYGDAFWPTYTTGDNTNLVAT DSMKNFIQRETCNFTGYDLESYCDFLARKFMATYPHTAGIQLSARQAPYSGVAEGKVAFAPSGPD VATACVELRRNGEALESVEASSGIHGFRLLRLGGSAFQGFLRDQYTTLPDIHNRPLHMWLDLEWH YIAPEAALTGGEVTAQVRRLVHEGFHSFESGSIQQVIYQLGTKMLADIPTISEVRLEANNRTWDT IVEQGDRLGVYTDARPPYGCLGLTLRR | 31 |
| *Terriglobus saanensis* Acidobacterium Uricase (only 2 cysteines and short 280 aa) | MAKLIDSRYGKARVRVMKLDRSQPQHQLLEWTVRVLLEGDFETAHTVGDNSNILPTDTMKNTVYS RAKESKAETPEEFAIELAEFLLGRNPQVHTVEVKIETAMWKRLVVDGKPHGSSFMRGSDELGTVL HHATRETKTMVCGVENMVILKSQNSSFEGYIQDDLTTLKPTADRLFATAMTADWDYTDGGSAFAA RREAIREAMLKAFAEHDSKSVQQTLYAMAEAAMAAVPAVNRVHMVMPNKHCLLVDLKHFGQENNN EIFVPTEDPHGYIEATVVRE | 32 |

TABLE 1-continued

Description of the Sequences

| Description | Sequences | SEQ ID NO |
|---|---|---|
| *Kinpidia tusciae* Uricase | MIMTGTMTSGTDQRTMYYGKGDVWVYRSYAKPLRGLGQIPESAFAGRPNVIFGMNVQMAVEGEAF<br>LPSFTEGDNSMVVATDSMKNFILRQAGAFEGATAEGFLEFVAGKFLEKYAHVSGVRLFGRQIPFD<br>ELPVPEQEGFRPGELVFRYSMNEYPTAFVAVRRGPEGPVVVEHAGGVAGLKLIKIKGSSFYGYIH<br>DEYTTLPEAQDRPLFIYLYIKWKYEHPEDFRAEHPERYVAAEQVRDIAHTVFHELTSPSIQNLIY<br>HIGRRVLTRFPQLLEVSFEANNRTWETVLEEVEDLAGKRAEAKVYTEPRPPYGFQGFTVTRKDLE<br>E | 33 |
| Consensus Uricase sequence from alignment | MTATAETSTGTKIVLGQNQYGKAEVRVVKITRDGDTHHIKDLNVSVALSGDMDAVHLSGDNANVL<br>PTDTQKNTVYAFAKEHGIGSAEQFGIRLARHFVTSQEPIHGARIRIEEYAWERIETSHDHSFVRK<br>GQETRTAQITYDGDWEVVSGLKDLTVLNSTGSEFWGYVKDKYTTLPETYDRILATDVSARWRYNW<br>TDDQPMPDWDKSYEQVRKHLLEAFAETYSLSLQQTLYQMGSRVLEARPEIDEIRFSLPNKHHFLV<br>DLEPFGLDNDNEVYFAADRPYGLIEATVLRDGAEPRIPVDMTNL | 34 |

DETAILED DESCRIPTION OF THE INVENTION

Urate oxidase (Uricase EC 1.7.3.3, uox) is a homotetrameric enzyme composed of four identical 34 KDa subunits. The enzyme is responsible for the initial step that begins a series of reactions that convert uric acid to a more soluble and easily excreted product, allantoin. In short, uricase catalyzes the reaction of uric acid (UA) with $O_2$ and $H_2O$ to form 5-hydroxy-isourate (HIU) and the release of $H_2O_2$. HIU is an unstable product that undergoes non-enzymatic hydrolysis to 2-oxo-4-hydroxy-4-carboxy-5-ureidoimidazoline (OHCU) and then decarboxylates spontaneously to form racemic allantoin. In species that contains a functional uricase, two additional enzymes are expressed (HIU hydrolase and OHCU decarboxylase) which catalyze these reaction more quickly to generate (s)-allantoin. A functional uricase can be found in a wide range of organisms: archaea, bacteria, and eukaryotes. However, in humans and some primates uricase is not expressed. The lack of uricase expression is attributed to three genetic mutations: a nonsense mutation at codon 33 (impacting orangutans, gorillas, chimpanzees, and humans), another nonsense mutation at codon 187 (impacting chimpanzees and humans) and a mutation at the splice acceptor site in intron 2 (impacting chimpanzees and humans). A number of hypotheses have been proposed to explain the evolutionary elimination of uricase activity and commensurate increase in UA levels. These include the idea that an increase in UA levels (powerful antioxidant and scavenger of oxygen radical) led to a decrease in oxygen free radical associated disease (cancer) and an increase in lifespan. Additionally, the fact that UA structurally resembles neuro stimulants such as caffeine and theobromine has led to the speculation that increased UA levels may have led to an intellectual/cognitive jump. Lastly it has been suggested that an increase in uric acid led to and helped maintain blood pressure levels required by hominids while consuming a very low salt vegetarian diet (1-2 million years ago). Regardless of the evolutionary advantage that may have resulted, the lack of uricase expression in humans has resulted in higher systemic UA levels and in some cases hyperuricemia conditions such as gout and tumor lysis syndrome.

Gout affects more than 8 million Americans and is a painful and debilitating inflammatory arthritis defined as serum UA levels exceeding UA solubility in body fluids. Serum UA levels higher than 6.8 mg/dL can result in UA crystal formation in tissues, provoking an acute inflammatory response. Acute gouty arthritic attacks (flares) and chronic inflammation that deposits UA crystals in fibrous tissues are painful and debilitating. The damage caused by gout can result in chronic pain, functional impairment at work and at home, and compromised health-related quality of life (Wertheimer, et al., supra).

Tumor lysis syndrome (TLS) usually occurs in patients with bulky, rapidly-proliferating, and treatment-responsive tumors. TLS is a potentially lethal complication of anticancer treatment that arises when large numbers of cancer cells are killed quickly and release breakdown products. Nucleic acid purines are metabolized to UA leading to a sharp increase in systemic UA. In severe cases, UA crystals form in the renal tubules causing UA nephropathy (acute renal failure). TLS has been reported across a broad range of tumor types (Ikeda, et al., Drugs, Diseases & Procedures, Medscape (Dec. 3, 2014)).

A variety of mechanisms of action exist for controlling hyperuricemia. Inhibitors of xanthine oxidase (enzyme that converts xanthine to UA) have been clinically prescribed since the 1960s. The most common of these, Allopurinol, is used by more the 2 million gout patients in the US. However, many patients continue to have higher than acceptable UA levels suggesting that hyperuricemia is not just a UA production problem. More recent studies have shown that UA levels in patients can also be controlled by inhibiting URAT1, an enzyme responsible for UA recycling. Uricosuric drugs (molecules that inhibit URAT1) act on the proximal tubules in the kidneys, where they interfere with the absorption of UA from the kidney back into the blood. Uricosuric drugs, such as Benzbromarone and Lesinurad, promote excretion of UA. Lastly, it has been shown that uricase treatment rapidly reduces UA levels in the peripheral blood stream by oxidizing UA to a more soluble product, allantoin. There are two clinically approved uricases, Krystexxa® and Elitek®.

Krystexxa® (pegloticase) is a PEGylated uricase approved for the treatment of chronic gout in adult patients refractory to conventional therapy. Krystexxa® is a chimeric protein of the pig and baboon uricase sequence that is hyper-PEGylated (~440 kDa PEG per tetramer). Krystexxa® is administered by an intravenous (IV) infusion over a 2 hour period. During phase 3 clinical trials, 26% of patients experienced infusion reactions and 6.5% of patients had reactions characterized as anaphylaxis (Baraf et al., *Arthritis Res Ther.*, 15(5):R137 (2013) and Strand et al., *J*

Rheumatol., 39(7): 1450-1457 (2012). Krystexxa® contains a black box warning for anaphylaxis and infusion reactions (see Krystexxa® prescribing information). As a result, patients are typically pretreated with antihistamines or corticosteroids prior to the IV infusion and then monitored post-infusion. Pretreatment, IV-infusion and post-infusion monitoring takes about 6-8 hours in an IV clinic. Treatment frequency is once every two weeks. In phase 3 clinical trials, a high percentage of patients developed anti-drug antibodies (~92%) and approximately 40% of patients experienced a positive primary endpoint (reduction in UA levels below 6 mg/dl for 6 months). In spite of the infusion reactions, anti-drug response, and inconvenient dosing schedule, dramatic results have been observed in clinical trials and case studies demonstrating the reduction or resolution of tophi (uric acid crystal deposits). Digital photos of patients with tophaceous gout (hands or feet) before and after multiple Krystexxa® treatments have demonstrated the potential for a uricase in resolving tophi and UA burden.

Elitek® (rasburicase) is a modified recombinant *Aspergillus flavus* uricase that is indicated for initial management of plasma uric acid levels in pediatric and adult patients with leukemia, lymphoma, and solid tumor malignancies who are receiving anti-cancer therapy expected to result in tumor lysis and subsequent elevation of plasma uric acid. Elitek® has a half-life of 16-21 hours in humans and must be dosed daily via IV infusion. Similar to Krystexxa®, Elitek® also has a black-box warning for anaphylaxis and hemolysis (especially in patients with a G6PD deficiency). Dosing frequency (daily), route of administration (IV), immunogenicity, and cost make Elitek® an unlikely option for chronic gout treatment.

In view of the foregoing, there is a need in the art to develop improved uricases that are safer, more convenient, and less immunogenic than the uricases that are currently available. The invention described herein fulfills this need.

I. Improved Uricase Sequences

In some aspects, a number of different uricase sequences are encompassed herein. The uricase described herein may comprise an amino acid sequence that is at least about 90%, 91%, 92%, 93%, 94%, 95%, 96%, 97%, 98%, or 99% identical to any one of SEQ ID NOS: 1-34, wherein the sequence is not any one of SEQ ID NOS: 27-33. In one embodiment, the uricase has the amino acid sequence of any one of SEQ ID NOS: 1-26 or 34. In another embodiment, the uricase comprises an amino acid sequence that is at least about 90%, 91%, 92%, 93%, 94%, 95%, 96%, 97%, 98%, or 99% identical to any one of SEQ ID NOS: 1-34, wherein the uricase sequence is not a naturally occurring uricase sequence.

In some embodiments, the uricase is at least about 90%, 91%, 92%, 93%, 94%, 95%, 96%, 97%, 98%, or 99% identical to SEQ ID NO: 1 or at least about 90%, 91%, 92%, 93%, 94%, 95%, 96%, 97%, 98%, or 99% identical to SEQ ID NO: 2.

In some embodiments, the uricase is a sequence that differs from any one of SEQ ID NOS: 1-34 by from about 1 to about 35 amino acids (e.g., by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids). For example, the uricase may differ from SEQ ID NO: 1 or SEQ ID NO: 2 by from about 1 to about 35 amino acids.

In some aspects, the uricase is a sequence that differs from any one of SEQ ID NOS: 1-34 by from about 1 to about 14 amino acids (e.g., by about 1, 2, 3, 4, 5, 6, 7, 8, 9, 10, 11, 12, 13, or 14 amino acids). For example, the uricase may differ from SEQ ID NO: 1 or SEQ ID NO: 2 by from about 1 to about 14 amino acids. In certain aspects, the uricase is SEQ ID NO 1 or SEQ ID NO: 2. In certain embodiments, the uricase is any one of SEQ ID NOs: 3-26 or 34. The uricase may "differ from" any one of SEQ ID NOs: 1-34 by comprising an addition, deletion, or substitution in the amino acid sequence. Methods for preparing amino acid additions, deletions, and substitutions are well known in the art.

In some embodiments, the uricase comprises a truncation at the N- and/or C-terminus, wherein the truncated uricase retains enzymatic activity. In one embodiment, from about 1-15 (e.g., about 1, 2, 3, 4, 5, 6, 7, 8, 9, 10, 11, 12, 13, 14, or 15) amino acids are truncated from the N-terminus. In another embodiment, from about 1-20 (e.g., about 1, 2, 3, 4, 5, 6, 7, 8, 9, 10, 11, 12, 13, 14, 15, 16, 17, 18, 19, or 20) amino acids are truncated from the C-terminus. In yet another embodiment, from about 1-15 (e.g., about 1, 2, 3, 4, 5, 6, 7, 8, 9, 10, 11, 12, 13, 14, or 15) amino acids are truncated from the N-terminus and from about 1-20 (e.g., about 1, 2, 3, 4, 5, 6, 7, 8, 9, 10, 11, 12, 13, 14, 15, 16, 17, 18, 19, or 20) amino acids are truncated from the C-terminus. In one embodiment, the uricase is a uricase of any one of SEQ ID NOs: 27-34, wherein the uricase comprises a truncation at the N- and/or C-terminus, as described above, wherein the truncated uricase retains enzymatic activity. In a further embodiment, the aforementioned truncated uricase contains from about 1 to about 14 (e.g., about 1, 2, 3, 4, 5, 6, 7, 8, 9, 10, 11, 12, 13, or 14) additional amino acid changes (e.g., additions, deletions, or substitutions). Methods for assaying enzymatic activity of a uricase are known in the art (e.g., product formation and substrate depletion assays), and any suitable method known in the art can be used to measure the enzymatic activity of the uricases described herein.

In some embodiments, the uricase is at least about 90%, 91%, 92%, 93%, 94%, 95%, 96%, 97%, 98%, or 99% identical to SEQ ID NOs: 27-33. In some aspects, the uricase differs from any one of SEQ ID NOs: 27-33 by from about 1 to about 35 amino acids (e.g., by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids).

In one embodiment, the uricase is at least about 90%, 91%, 92%, 93%, 94%, 95%, 96%, 97%, 98%, or 99% identical to NCBI Accession Number D0VWQ1, WP_011525965, WP_010887803, WP_013581210.1, WP_011682147, WP_013569963, or ADG06709. In some aspects, the uricase differs from any one of NCBI Accession Number D0VWQ1, WP_011525965, WP_010887803, WP_013581210.1, WP_011682147, WP_013569963, or ADG06709 by from about 1 to about 35 amino acids (e.g., by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids).

In some embodiments, the uricase is about 90%, 91%, 92%, 93%, 94%, 95%, 96%, 97%, 98%, or 99% identical to SEQ ID NO: 27. In some aspects, the uricase differs from SEQ ID NO: 27 by from about 1 to about 35 amino acids (e.g., by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids).

In some embodiments, the uricase is at least about 90%, 91%, 92%, 93%, 94%, 95%, 96%, 97%, 98%, or 99% identical to SEQ ID NO: 28. In some aspects, the uricase differs from SEQ ID NO: 28 by from about 1 to about 35 amino acids (e.g., by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids).

It is well understood in the art that processing of expressed proteins can result in the cleavage of the N-terminal methionine residue, a co-translational modification that can occur in both prokaryotic and eukaryotic hosts (Sherman, et al., Bioessays, 3: 27-31 (1985)). This processing, which is enzymatically effected by methionine aminopeptidase, is dependent upon the identity of the amino acid residue adjacent to the amino terminus. Methionine is efficiently removed from proteins when the second residue is glycine or an amino acid with a small side chain such as alanine (Hirel et al., *Proc. Natl. Acad. Sci. U.S.A.*, 86: 8247-8251 (1989) and Huang et al., *Biochemistry*, 26: 8242-8246 (1987)). However, N-terminal methionine is not cleaved when an amino acid with a large side chain is the adjacent residue. Variable degrees of cleavage may occur when the second residue is an intermediate sized amino acid such as threonine or asparagine (Hirel et al., supra). Thus, in some embodiments, the methionine at position 1 of the uricase is cleaved, such that the processed form of the uricase does not contain a methionine at position 1. In another embodiment, the uricase retains the methionine at position 1. In order to prevent cleavage of the methionine at position 1, the uricase may comprise one or more amino acid substitutions or deletions following the N-terminal methionine. Such substitutions or deletions would be designed to result in a large amino acid being at the second position within a sequence. Examples of large amino acids are glutamine, glutamic acid, phenylalanine, methionine, lysine, tyrosine, tryptophan and arginine. For example, in some aspects, the uricase may not comprise a threonine at position 2 and position 2 is either deleted or substituted, wherein the numbering is relative to SEQ ID NO: 27. In some embodiments, the uricase sequence has been modified to comprise an alanine or other small amino acid at position 2 (i.e., the amino acid next to the N-terminal methionine). Examples of small amino acids are glycine, alanine, serine, proline, threonine, valine and cysteine, but preference is given to the smallest of these (glycine and alanine) to limit the possibility of partial processing (Hirel et al., supra).

In some embodiments, the uricase sequence is conjugated or recombinantly fused to a synthetic or biosynthetic polymer in order to extend the half-life of the protein and/or to mitigate immunogenicity. Exemplary polymers that may be used in the invention are polyethylene glycol (PEG), polymers of phosphorylcholine (see, e.g., US Patent Application Publication 2013/0034517), polymers of repeating peptides such as "PAS" or "X-TEN" sequences (see, e.g., Schlapschy et al., *Protein Eng. Des. Sel.* 26: 489-501 (2013), Schellenberger et al., *Nat. Biotechnol.*, 27: 1186-1190 (2009), and Podust et al., *Protein Eng. Des. Sel.*, 26: 743-753 (2013)), or carbohydrate-based polymers such as heparosan (see, e.g., International Patent Application Publication WO 2014/060397) or hydroxyethyl starch (see, e.g., EP 2270036). In other embodiments, the uricase sequence may be recombinantly fused to polypeptides that prolong the circulation half-life by reducing the rate of renal clearance. Such fusion partners are well understood in the art, and include agents that directly bind the neonatal Fc receptor (FcRn) in a pH dependent manner (e.g., Fc region of immunoglobulins or serum albumin), or alternatively bind to a naturally-occurring FcRn-binding moiety (e.g., polypeptides that bind to serum albumin). In another embodiment, the uricase sequence may be conjugated or recombinantly fused to one or more repeats of a C-terminal peptide fragment derived from the beta subunit of human chorionic gonadotropin (see, e.g., U.S. Pat. No. 6,225,449).

In some embodiments, a synthetic or biosynthetic polymer is conjugated to the N- and/or C-terminus of the uricase in order to extend the half-life of the protein and/or to mitigate immunogenicity.

In some embodiments, the uricase sequence is modified to create 1-6 (e.g., 1, 2, 3, 4, 5, or 6) surface accessible sites for conjugation. For example, in some embodiments, the uricase sequence is modified to contain 1, 2, 3, 4, 5, or 6 surface accessible cysteine residues to which a polymer (e.g., PEG) may be conjugated. In some embodiments, a naturally-occurring uricase sequence that does not contain any cysteines or contains only a few cysteines provides a beneficial starting sequence, so that cysteines can be inserted into the appropriate, surface-accessible locations. In other embodiments, the uricase sequence is modified to contain 1, 2, 3, 4, 5, or 6 surface accessible non-naturally occurring amino acids to which a polymer may be conjugated.

In some embodiments, a naturally-occurring uricase sequence is modified to mutate some or all of the existing cysteines (through deletion and/or substitution) with alternative amino acids. In some embodiments, new cysteines are introduced at desired locations (through addition and/or substitution), to enable site-specific conjugation of polymers or polypeptides that can modify pharmacokinetic behavior. In one embodiment, selection of an appropriate amino acid for Cys-substitution is guided by alignment of the uricase of interest to other uricase sequences in order to determine the natural amino acid diversity at the equivalent position across all uricases. A non-cysteine amino acid is then selected based on its prevalence at the position of interest within other uricases. In another embodiment, selection of an appropriate amino acid for Cys-substitution is guided by analysis of the crystal structure for that particular uricase in order to determine which amino acid residues are surface accessible. One or more surface accessible amino acids are then selected and modified to cysteine. In some instances, the cysteines in the final modified uricase sequence are located in surface accessible positions so that the cysteines may be PEGylated.

In some embodiments, the uricase comprises from about 1 to about 6 cysteines, specifically about 1, 2, 3, 4, 5, or 6 cysteines. In one embodiment, the uricase comprises about 2 cysteines.

In certain embodiments, the uricase comprises a PEG moiety attached to the cysteine residue(s). Control over the number and placement of cysteine residues allows for control over the number of PEG attachment sites, and optimal properties of the resultant conjugate including biophysical attributes and enzymatic activity.

Polyethylene glycol (PEG) is a polyether compound with the structure $H-(O-CH_2-CH_2)_n-OH$. The PEG reagents most typically used for protein conjugation are monomethoxy poly(ethylene glycol) derivatives, having the structure $CH_3-O-(CH_2-CH_2-O)_n-X$, wherein X contains a linear linker and reactive functional group (linear PEG). In some cases, X may contain a branching element, such that the PEG reagent contains one reactive functional group and more than one PEG polymer chain (branched PEG) or more than one reactive functional group and PEG polymer chains (forked PEG). PEG reagents may include about 5, 10, 20, 40, 60 and 80 kDa of total PEG polymer.

In some embodiments, thiol-reactive PEGs may be used to react with the thiol group on at least one cysteine. For example, PEG-maleimide may be used, as well as PEG-orthopyridyl-disulphide, PEG-vinylsulphone, and PEG-iodoacetamide. In other embodiments, thiol-reactive PEGs may have a linear or branched structure with a single thiol-reactive moiety, or may have a forked structure with two or more reactive groups per PEG molecule.

A variety of approaches, thus, are known in the art and any suitable method known in the art may be used to PEGylate the cysteine(s) in the uricase.

In some embodiments, the uricase comprises a cysteine in at least one of the following positions: 11C, 33C, 119C, and 142C, wherein the position numbering is relative to SEQ ID NO: 27.

In one embodiment, the uricase comprises a cysteine in at least one of the following positions: 11C, 33C, 119C, 120C, 142C, 196C, 238C, 286C, and 289C wherein the position numbering is relative to SEQ ID NO: 27.

As a major family of cell adhesion receptors, integrins are known play a key role in cell-cell and cell-extracellular matrix interactions. The tripeptide Arg-Gly-Asp (RGD) within fibronectin has been shown to mediate cell adhesion through integrin binding. Synthetic peptides containing an RGD motif have been generated specifically to target alpha (v)-integrin for internalization by integrin-dependent endocytosis as a potential cancer therapeutic. Putatively, an integrin binding motif (RGD) could be problematic for a therapeutic that is expected to function in the peripheral blood stream. Thus, in certain aspects of the invention, the uricase does not comprise an RGD sequence.

Methods for mutating amino acids are well-known in the art, and such methods can be used to mutate one or more of the RGD amino acids to any other naturally occurring amino acid. In one embodiment, the arginine in the RGD motif is mutated to a serine, such that the uricase contains an SGD instead of an RGD. In another embodiment, the arginine, the glycine, and/or the aspartic acid in the RGD motif is mutated to any other naturally occurring amino acid, such that the uricase does not contain an RGD motif. In one embodiment, a number of uricase amino acid sequences are aligned using methods known in the art to determine the most highly conserved residue at the amino acid positions where an RGD motif is present, and one or more amino acids present in the RGD motif are mutated to the amino acid residue that is most conserved at that particular amino acid position. For example, if the G and the D of the RGD motif are highly conserved, only the R would be mutated to the amino acid residue that is most highly conserved at that particular position (e.g., serine).

Methods for preparing nucleotide sequences encoding the uricase amino acid sequences disclosed herein are well-known in the art, such that one of ordinary skill in the art can readily prepare a nucleic acid sequence encoding the uricase amino acid sequences disclosed herein. Thus, in one embodiment, the invention comprises a nucleic acid sequence encoding the uricase amino acid sequence disclosed herein. Suitable expression vectors are known and available in the art, such that the invention also encompasses a vector comprising a nucleic acid sequence encoding the uricase amino acid sequence disclosed herein. In yet another embodiment, the invention encompasses a cell line comprising the expression vector. The cell line can be a eukaryotic or a prokaryotic cell line. In a preferred embodiment, the cell line is a prokaryotic cell line, such as E. coli, Corynebacterium, or Pseudomonas fluorescens. In another embodiment, the cell line is a eukaryotic cell line such as Saccharomyces cerevisiae, insect cells, etc. Mammalian cell lines such as Chinese hamster ovary (CHO) cells may also be used.

In one embodiment, the invention encompasses a composition comprising the uricase described herein. In one aspect, the uricase in the composition forms a tetramer. In some aspects, at least 93% (e.g., 93%, 94%, 95%, 96%, 97%, 98%, 99% or even 100%) of the uricase monomers present in the composition are mono-pegylated (e.g., one PEG moiety is present on each monomer). In some aspects, at least 93% (e.g., 93%, 94%, 95%, 96%, 97%, 98%, 99% or even 100%) of the uricase monomers present in the composition are di-pegylated (e.g., two PEG moieties are present on each monomer). In some aspects, at least 93% (e.g., 93%, 94%, 95%, 96%, 97%, 98%, 99% or even 100%) of the uricase monomers present in the composition are tri-pegylated (e.g., three PEG moieties are present on each monomer).

In another embodiment, the invention encompasses a statistical model for determining the PEGylation efficiency of an oligomeric protein, such as a tetramer of a uricase protein described herein. The invention also provides a statistical measure for deriving the overall functionalization of an oligomeric protein from the data obtained from readily accessible assays that cause non-covalently associated subunits to dissociate, as described in Example 14 herein.

In another embodiment, the invention encompasses a statistical approach based on a multinomial distribution that allows the computation of overall protein conjugation for oligomeric proteins when the size and nature of the protein or the biophysical properties of the conjugate do not allow analysis under native conditions.

II. Methods of Treatment

In some aspects, the invention encompasses a method of treating a hyperuricemic patient comprising administering any of the uricases described herein, and thereby reducing levels of uric acid and/or UA crystal burden. The patient may have any number of conditions resulting in hyperuricemia. For example, the patient may have gout, such as, but not limited to chronic refractory gout, tophaceous gout and/or high UA burden. As another example, the patient may have or be at risk for tumor lysis syndrome.

In some aspects of the method, the uricase may be administered subcutaneously. In other aspects, it may be administered intravenously or intramuscularly.

For certain treatment methods, the patient may have a serum UA level higher than 6.8 mg/dL before treatment and a serum UA level lower than 6.8 mg/dL after treatment.

In some embodiments, the uricase or the method of treatment is not associated with anaphylaxis. In one embodiment, the uricase or the method of treatment is non-immunogenic.

EXAMPLES

Example 1. Selection of Uricase Enzyme

More than 200 uricase sequences from publicly-available databases were aligned, including mammalian, plant, microbial, etc. uricases. Candidate uricases with sequences available in the databases were selected using proprietary criteria that included (but not limited to): favorable biological properties (such as expression in E. coli, neutral pH solubility, neutral pH activity), low sequence identity or similarity to other sequences (diversity), low endogenous Cys content, and organisms having interesting properties suggesting that its uricase would have favorable properties (extremophile, thermophile, acidophile, etc).

After this process, the following 7 candidate sequences were chosen for further investigation: *Arthrobacter globiformis* uricase (SEQ ID NO: 27), *Deinococcus geothermalis* uricase (SEQ ID NO: 28), *Deinococcus radiodurans* uricase (SEQ ID NO: 29), *Granulicella tundricola* uricase (SEQ ID NO: 30), *Solibacter usitatus* uricase (SEQ ID NO: 31), *Terriglobus saanensis* uricase (SEQ ID NO: 32) and *Kyrpidia tusciae* uricase (SEQ ID NO: 33). Additionally, as an 8th sequence, a consensus uricase sequence was also devised from the alignment of many uricase sequences. The consensus sequence is represented by SEQ ID NO: 34. As shown in Table 2 below, there is a significant amount of diversity between the 8 sequences that were selected.

TABLE 2

Uricase Sequence Identity Comparison

|  | Consensus | Arthrobactor globiformis | Deinococcus geothermalis | Deinococcus radiodurans | Granulicella tundricola | Solibacter usitatus | Terriglobus saanensis | Kyrpidia tusciae |
|---|---|---|---|---|---|---|---|---|
| Consensus | 100 | 61.7 | 44.4 | 44.1 | 36.7 | 28.0 | 39.4 | 28.5 |
| Arthrobactor globiformis |  | 100 | 41.2 | 43.4 | 42.7 | 29.2 | 38.4 | 27.3 |
| Deinococcus geothermalis |  |  | 100 | 75.1 | 36.0 | 23.4 | 34.5 | 22.2 |
| Deinococcus radiodurans |  |  |  | 100 | 36.3 | 23.1 | 37.0 | 21.6 |
| Granulicella tundricola |  |  |  |  | 100 | 26.4 | 58.4 | 27.1 |
| Solibacter usitatus |  |  |  |  |  | 100 | 21.5 | 43.7 |
| Terriglobus saanensis |  |  |  |  |  |  | 100 | 25.6 |
| Kyrpidia tusciae |  |  |  |  |  |  |  | 100 |

Example 2. Screening Paradigm

An initial screening paradigm was used to identify candidates for further optimization. The 8 uricase sequences described in Example 1 were cloned with an amino terminal His tag and expressed in *E. coli*. Each uricase construct was evaluated for expression level and in particular, soluble expression. Uricase expressing *E. coli* were lysed and soluble material was separated from insoluble (pellet) material. The lysates were separated by SDS-PAGE and the proteins were visualized by Coomassie blue staining. As shown in FIG. 1, most uricases were present at high level in the insoluble (P) material. The pig-baboon chimera appears to express almost entirely in the pellet (P) (insoluble) fraction (FIG. 1, Lane 9). Cytosolic soluble (S) expression was considered a favorable property. The 8 uricases were then purified from the *E. coli* cell lysates by Ni-affinity chromatography. Protein yield was determined by measuring the absorbance at 280 nm. Protein size was verified by mass spectrometry and tetramer formation was confirmed by size exclusion chromatography and light-scattering detection (see Table 3 below).

TABLE 3

Mass Spec and SEC-LS Analysis

|  | Predicted Mass (kDa) | Measure Mass Monomer (kDa) | Theoretical Tetramer (kDa) | Measured SEC-LS Tetramer (kDa) | Tetramer Formation |
|---|---|---|---|---|---|
| Arthrobactor globiformis | 33.88 | 33.88 | 135.52 | 135.20 | ✓ |
| Deinococcus geothermalis | 35.19 | 35.19 | 140.76 | 136.30 | ✓ |

TABLE 3-continued

Mass Spec and SEC-LS Analysis

|  | Predicted Mass (kDa) | Measure Mass Monomer (kDa) | Theoretical Tetramer (kDa) | Measured SEC-LS Tetramer (kDa) | Tetramer Formation |
|---|---|---|---|---|---|
| Terriglobus saanensis | 32.69 | 32.69 | 130.76 | 126.80 | ✓ |
| Consensus | 35.83 | 35.83 | 143.32 | 141.30 | ✓ |
| Deinococcus radiodurans | 35.58 | 35.58 | 142.32 | 140.40 | ✓ |
| Granulicella tundricola | 33.60 | 33.60 | 134.40 | 128.00 | ✓ |
| Kyrpidia tusciae | 38.24 | 38.24 | 152.96 | 147.20 | ✓ |
| Solibacter usitatus | 33.24 | 33.24 | 132.96 | 137.70 | ✓ |

Three uricases were eliminated from further evaluation based on unfavorable expression, solubility or purification yields, namely, *Solibacter usitatus, Kyrpidia tusciae*, and *Granulicella tundricola*.

Figure 2A:
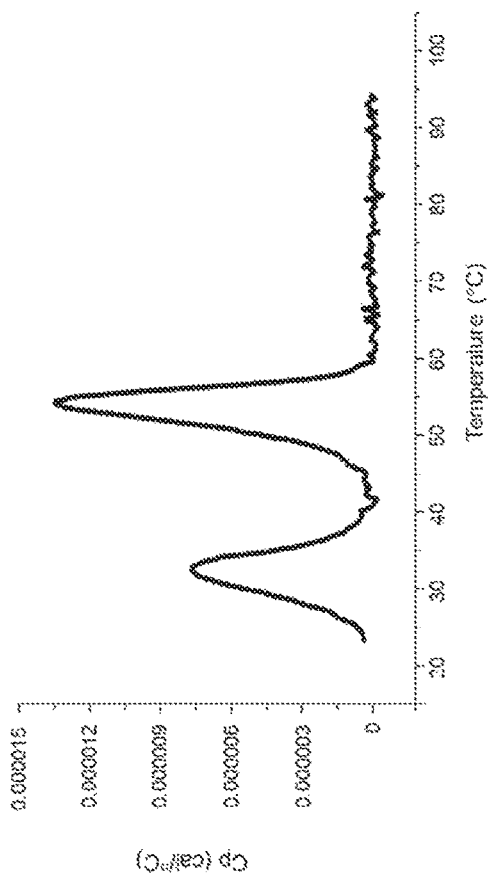
FIGS. 2A-B depict the differential scanning calorimetry stability for *Deinococcus geothermalis* uricase (FIG. 2A) and *Deinococcus radiodurans* uricase (FIG. 2B).
Figure 2B:
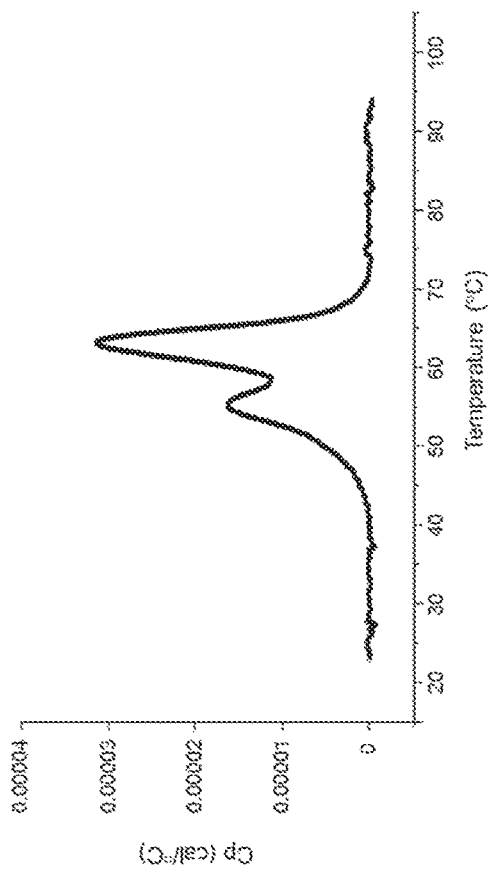

Differential scanning calorimetry (DSC) measurements were performed to assess thermal stability (see Table 4 below). Two transitions were observed for each uricase. *Terriglobus saanensis* and *Deinococcus radiodurans* exhibited a thermal transition (TM1) that was lower than desired and, as a result, these two uricases were eliminated from the pool of candidates. FIGS. 2A and 2B show two examples of the DSC results (*Deinococcus geothermalis* uricase (FIG. 2A) and *Deinococcus radiodurans* uricase (FIG. 2B)).

TABLE 4

Differential scanning calorimetry stability

| | TM1 (° C.) | TM2 (° C.) |
|---|---|---|
| *Arthrobactor globiformis* | 47.5 | 73.0 |
| *Deinococcus geothermalis* | 55.0 | 63.0 |
| *Terriglobus saanensis* | 42.0 | 90.0 |
| Consensus | 56.0 | 69.0 |
| *Deinococcus radiodurans* | 32.0 | 54.0 |

Five uricases (SEQ ID NOs: 27, 28, 29, 32, and 34) were evaluated for neutral pH solubility characteristics and activity in terms of product formation ($H_2O_2$) at pH 9.0 and 7.4. In the product formation assay, allantoin formation is proportional to $H_2O_2$ formation, which is linked to colorimetric horseradish peroxidase-catalyzed, colorimetric reaction. The appearance of hydrogen peroxide can be measured by an increase in absorbance at 540 nm. Product formation assays were proportional to substrate depletion assays in terms of uricase activity. However, product formation assay do not allow for continuous monitoring of enzyme activity over time. The substrate depletion assays were much better for assessing kinetic parameters like Vmax and Km.

Figure 3:
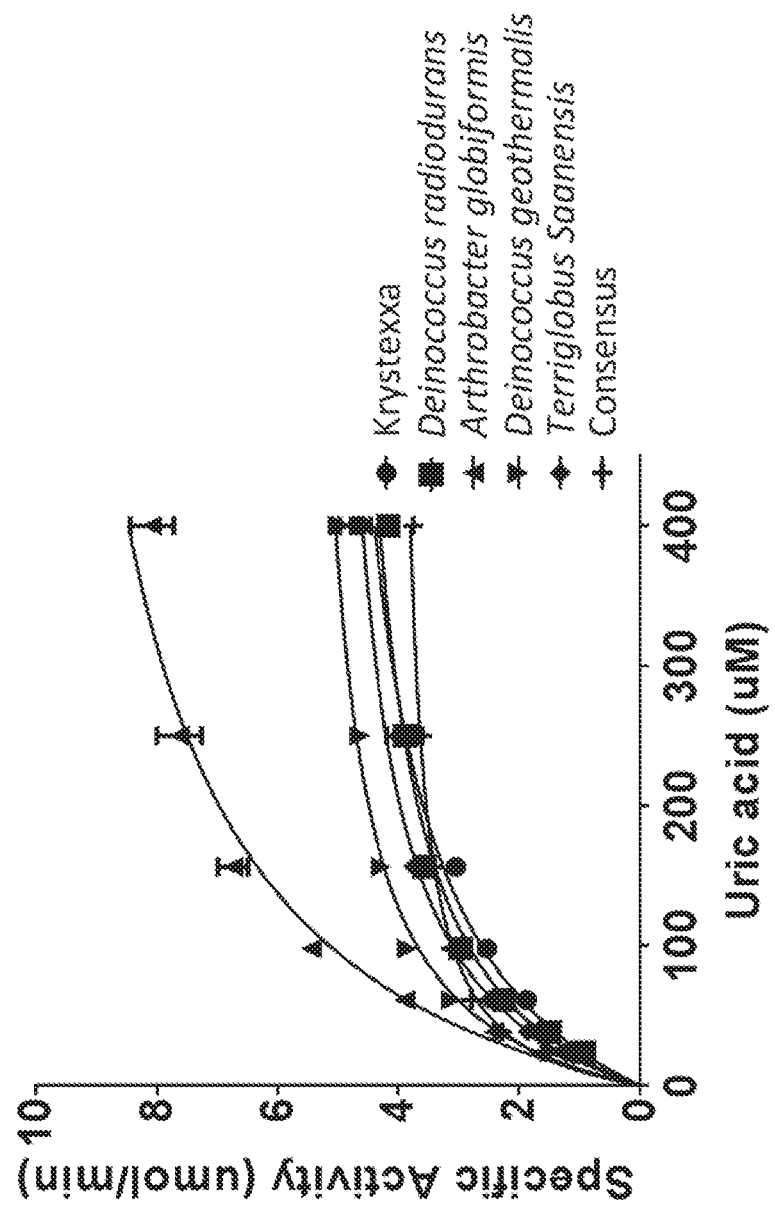
FIG. 3 is a line graph that depicts the results of uricase activity assays at a variety of substrate (UA) concentrations. The solid lines depict a Michaelis-Menten kinetic fit.

Substrate depletion (UA) is another common method for assessing uricase activity. In the substrate depletion assay, uricase, UA, and phosphate buffer were incubated for 1 hour at the stated temperature (typically 30° C.). Uricase was then diluted to 1 µg/mL and combined with a curve of UA (400 µM diluted down 1:1.6 to 23.8 µM) in 0.1M phosphate buffer (PB), pH 7.4. In some assays 1 mM DTT was added to the assay. The Molecular Devices reader temperature was set to the 30° C. Absorbance measurements at 292 nm were captured every 20 seconds for a period of 10 minutes. The rate of UA degradation was calculated by SoftMax Pro software. Vmax and Km were calculated for these uricases (see Table 5 below). Data are shown in FIG. 3. Each curve represents 4320 specific activity data points.

TABLE 5

Vmax, Km and kcat/Km

| Uricase | Buffer | pH | Vmax | Km |
|---|---|---|---|---|
| Krystexxa | PB | 7.4 | 5.68 | 116.3 |
| *Arthrobacter globiformis* | PB | 7.4 | 10.80 | 109.7 |
| *Deinococcus geothermalis* | PB | 7.4 | 5.75 | 55.73 |
| *Terriglobus saanensis* | PB | 7.4 | 5.48 | 76.18 |
| Consensus | PB | 7.4 | 4.09 | 31.76 |
| *Deinococcus radiodurans* | PB | 7.4 | 5.20 | 83.06 |

Based on kinetic parameters, two uricases were selected for further study, *Deinococcus geothermalis*, which had a 2 fold improved Vmax relative to Krystexxa® (10.8 versus 5.7), and *Arthrobacter globiformis*, which had a 2 fold better Km relative to Krystexxa® (55.7 versus 116.3). Both uricases had about a 2 fold better kcat/Km relative to Krystexxa®. Lastly, although the consensus uricase exhibited favorable kinetics, the consensus sequence is 61.7% identical to *Arthrobacter globiformis* whereas *Deinococcus geothermalis* and *Arthrobacter globiformis* are only 41.2% identical to each other, suggesting a greater diversity between these two. The high degree of diversity was deemed advantageous, and therefore, the *Deinococcus geothermalis* and *Arthrobacter globiformis* uricases were selected for further investigation.

Example 3. Dose Modeling Suggests that Kcat is the Most Important Kinetic Parameter Gout and tumor lysis syndrome patients typically have saturating levels of UA (>6.8 mg/dl, 408 µM). Therefore, it was hypothesized that Vmax (kcat) is the most important kinetic parameter for a therapeutic uricase. Dose models were generated based on an improvement in kcat (*Arthrobacter Globiformis*) or Km (*Deinococcus geothermalis*). Although the modeling predicted an improved km (*Deinococcus geothermalis*) would provide no advantage in dosing amount or frequency, the modeling predicted that an improved kcat (*Arthrobacter globiformis*) would provide an advantage in terms of dosing amount and frequency. Thus, the results of the dose modeling suggest that kcat is the most important kinetic parameter for a therapeutic uricase.

Example 4. Immunogenicity Based on Overlapping Peptide Analyses

Since immunogenicity has proven to be a problem in the clinic for currently available uricases, both *Arthrobacter Globiformis* and *Deinococcus geothermalis* uricases were screened for putative T-cell immunogenicity by EpiScreen™ analysis. The sequences of both uricase enzymes were analyzed using overlapping peptides for the presence of CD4+ T cell epitopes (EpiScreen™ T cell epitope mapping analysis). A total of 93 overlapping 15mer peptides spanning the sequence of uricase *Arthrobacter Globiformis* and 94 for *Deinococcus geothermalis* were tested against a cohort of 54 healthy donors screened to represent a cross section of HLA-DRB1 haplotypes. CD4+ T cell responses against individual peptides were measured using $^3H$ thymidine incorporation proliferation assays and the results were used to compile a T cell epitope map of the two uricase sequences. A putative T-cell epitope was considered if 3 or more donor samples elicited a CD4 stimulation index score greater than 2.00 in the assay. A total of five putative T-cell epitopes were identified in the *Arthrobacter globiformis* sequence. In this case, no peptides elicited a T-cell response in greater than 4 donors samples (<10%). In addition, stimulation index magnitude for each positive peptide was relatively low suggesting that the peptides may not be strong T-cell epitopes. Overlapping peptide T-cell analysis of *Deinococcus geothermalis* suggested the existence of six putative epitopes. Some of these peptides elicited a positive T-cell response in greater than 10% of the donors screened and the magnitude of the response (stimulation index) was greater.

Based on these results and the improved Vmax for *Arthrobacter globiformis* it was determined to further optimize this sequence.

Example 5. Sequence Evolution for *Arthrobacter globiformis* Uricase

A. Initial Sequence Evolution

SEQ ID NO: 22 was modified to add an N-terminal His tag and short linker, and to truncate the C-terminal 11 amino acids in order to eliminate the C-terminal Cys, resulting in SEQ ID NO: 21.

B. Changing RGD to SGD

Figure 4:
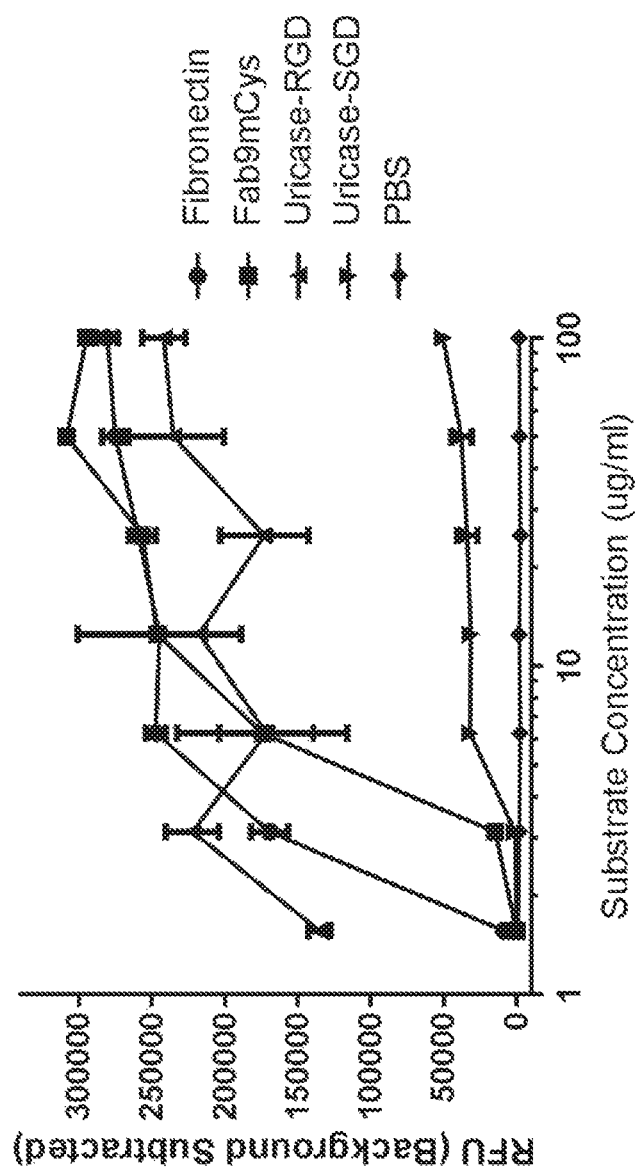
FIG. 4 is a line graph that depicts the adhesion of M21 cells to immobilized fibronectin, Fab9mCys, or uricase variants.

As a major family of cell adhesion receptors integrins are known play a key role in cell-cell and cell-extracellular matrix interactions. The tripeptide RGD within fibronectin has been shown to mediate cell adhesion through the RGD motif. Putatively, an integrin binding motif (RGD) could be problematic for a therapeutic that is expected to function in the peripheral blood stream. SEQ ID NO: 21 and SEQ ID NO: 22 both contain an RGD motif. An M21 tumor cell adhesion assay was conducted to determine if the RGD is surface accessible. M21 cells were used because they express avP3 and avP5 integrins. An RGD-containing fibronectin substrate, PBS (negative control), or test article was coated on an ELISA plate at 0-100 ug/ml overnight in PBS. Fluorescently labeled (calcein-AM) M21 cells were incubated for 1 hour at 37° C. on coated plates. Unbound cells were washed away and bound cells were measured by total fluorescence. Fab9mCys is an IgG that contains an RGD within the CDR-H3 loop and serves as a positive control along with fibronectin. Results are shown in FIG. 4 illustrating that RGD containing *Arthrobacter Globiformis* uricase binds the M21 cells. These data suggest that the RGD in *Arthrobacter Globiformis* uricase is surface accessible.

Using a database of greater than 200 aligned uricases it was determined that the Glycine (G) and Aspartate (D) in the RGD motif were highly conserved residues across the aligned uricases. However, the Arginine (R) was not a highly conserved position and the consensus residue at this position is a Serine (S). Therefore, site-directed mutagenesis was used to replace the R in the RGD motif with an S, thus making the RGD an SGD. This modification removes the potential integrin binding motif, thereby generating a uricase having SEQ ID NO: 20, wherein the His and linker tag on the N-terminus of the sequence as shown is optional.

C. Evaluating SGD Modification

The RGD to SGD mutation was evaluated for its impact on the expression, solubility, purification yield, etc. Although, the SGD mutation appears to have decreased the soluble expression a bit, culture conditions can be optimized to improve soluble expression.

Figure 5:
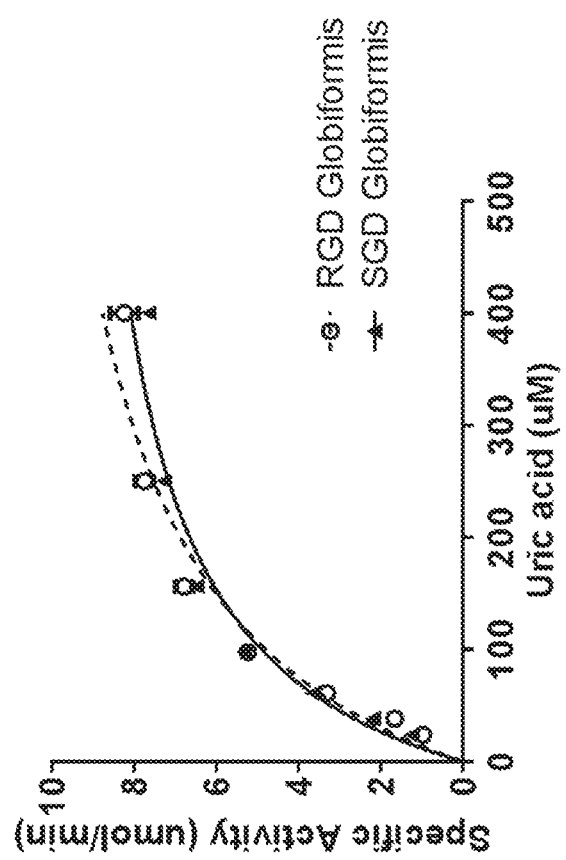
FIG. 5 is a line graph that depicts the results of uricase activity assays at a variety of substrate (UA) concentrations. The solid and dashed lines depict a Michaelis-Menten kinetic fit.

The RGD to SGD mutation showed a marked reduction in the integrin binding assay (see FIG. 4). Both uricases were evaluated for activity at pH 7.4. The SGD mutation appears to have comparable activity (see FIG. 5).

Example 6. Assessing Immunogenicity of Modified Arthrobacterglobiformis Uricase

A. LONZA Immunogenicity Assay (Epibase®)

Although *Arthrobacter globiformis* uricase (SEQ ID NO: 22) had 5 putative T-cell epitopes based on the EpiScreen assay, none of these elicited a strong response in greater than 10% of the donor samples. Additionally, overlapping synthetic peptide T-cell epitope assays are known to over predict MHC-class 2 epitopes. This is likely due to the fact that not all potential peptide variants will exist within an endogenous endosomal degradation process of the protein therapeutic. As a result, modified *Arthrobacter globiformis* (SEQ ID NO: 18) was screened as a holoprotein in the Epibase® immunogenicity assay. The Epibase® assay is a human PBMC T-cell immunogenicity assay used to assess "immunogenicity risk." Although this assay cannot necessarily predict clinical immunogenicity, it can be used to identify "high risk" and "low risk" proteins based on the number of responders and the overall response magnitude (Stimulation index). In this assay, PBMC samples from 202 normal donors were used to screen the T-cell immunogenicity of a uricase candidate relative to a negative control (buffer) and a positive control (KLH). Here, 202 donors were selected to represent HLA-DRB1 frequencies in the Caucasian population (see FIG. 6). PBMC from frozen stocks were thawed and added to a 96 well plate at a density of $3 \times 10^5$ cells per well. Test articles were added to media at 30 ug/ml (Buffer, KLH, SEQ ID NO: 18). Each test condition was carried out in 8-plicate (n=8). PBMC were incubated for 7 days. On day 7, PBMCs were labeled for surface CD3$^+$ and CD4$^+$ markers. Proliferating CD4$^+$ T-cells were identified by flow cytometry. Stimulation indices (SI) values describes the ratio of proliferating CD3$^+$CD4$^+$ T-cell in antigen treated versus untreated wells. SI values >2 are considered positive which is supported by p-value <0.05. Population immunogenicity analysis was also determined by calculating the magnitude of the T-cell response for the entire population.

Figure 7A:
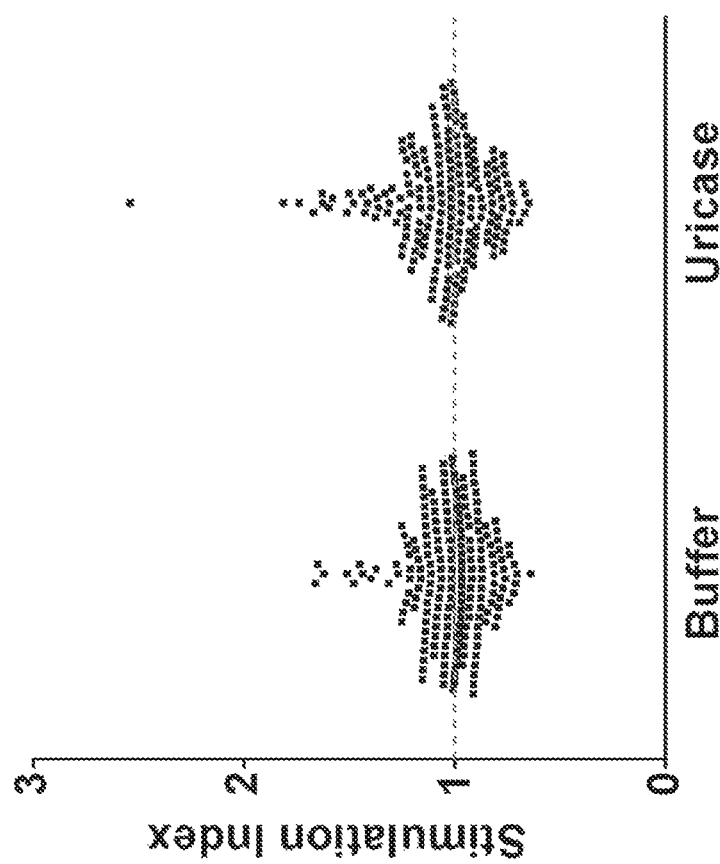
Figure 7B:
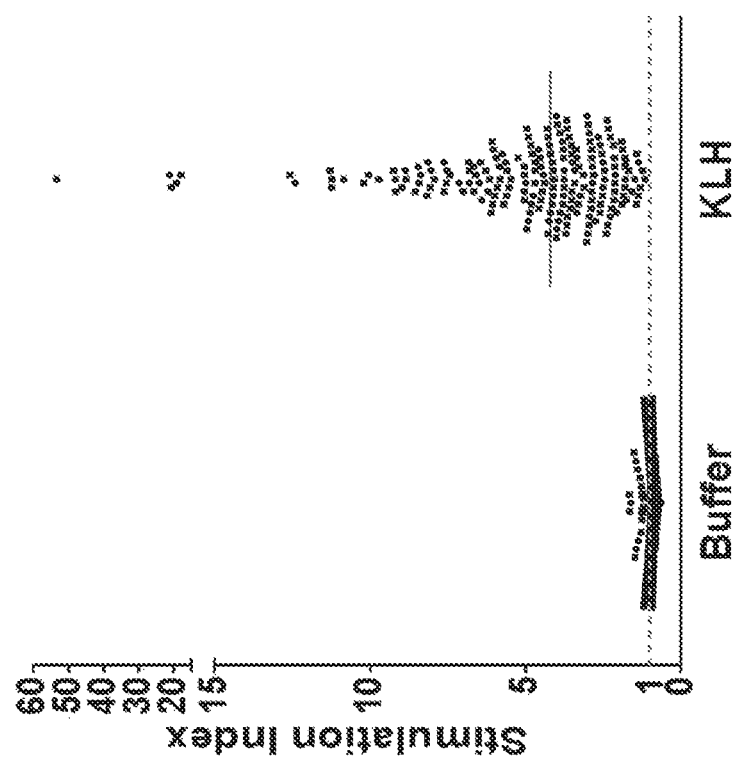

The results were as follows: negative control—0/202 donor samples (0%) responded with a mean population SI=1.0; uricase candidate—1/202 donor samples (0.5%) responded with a mean population SI=1.03; positive control—181/202 donors (91%) responded with a mean SI=4.2. Individual donor data is shown in FIGS. 7A-C. FIG. 7A shows that the buffer (negative control) stimulation index is 1.0 and the KLH (positive control) had a 92% response (SI>2). The KLH mean total SI=4.2. FIG. 7B shows the uricase candidate in comparison to the buffer control. A response rate of 4% or less in this assay is considered to be "low risk" and historical screening of other potential clinical compounds has produced rates in the range of 20-25% immunogenicity. FIG. 7C shows that the buffer stimulation index is 1.0, the KLH stimulation index is 4.2, and the uricase candidate stimulation index is 1.03. Although this assay cannot necessarily predict clinical immunogenicity, it can be used to assess risk of immunogenicity and these data suggest that the uricase evaluated is "low risk" for clinical immunogenicity. Considering that the uricase protein sequence that was tested is microbial in origin (*Arthrobacter globiformis*), this is quite a surprising finding.

Example 7. His Tag Removal

The N-terminal His tag was added to the N-terminus of the uricase sequences in order to provide an efficient method of purifying the uricase proteins that were generated (i.e., Ni-affinity purification). While the His tag provides advantages during discovery, especially in the area of purification, it is desirable to remove the His tag before preparation of a drug product.

Example 8. Optimizing the N-terminus

It is well-known that when proteins are express in *E. coli* the N-terminal methionine can be removed by Met aminopeptidase depending on the second residue following the methionine. If a small residue is in the second position, cleavage typically occurs. If a bulky residue is in the second position, no cleavage occurs. Whereas, if the second residue is neither bulky nor particularly small the Met aminopeptidase may function to cleave some Met but not all generating a heterogenous drug substance. Three N-terminal variants were generated and analyzed for expression, solubility, methionine cleavage, and activity in order to determine the optimum N-terminal sequence.

The starting sequence for this process was SEQ ID NO: 12 and three variants were created. SEQ ID NO: 13 (variant 1) has a deletion of Thr2. SEQ ID NO: 14 (variant 2) has a deletion of Thr2-Ala5, and it was expected that the N-terminal Met would be retained. SEQ ID NO: 15 (variant 3) has a deletion of Thr2-Thr9, and it was expected that the N-terminal Met would be processed.

The three N-terminal uricase variants were cloned, expressed in *E. coli*, and purified. Each construct was expressed in the soluble fraction similar to the His-tagged constructs. Due to the lack of a His tag, a purification procedure was worked out for these constructs. In short, this included a Q ion-exchange chromatography step (Buffer A: PBS, pH 7.8, 5 mM DTT; Buffer B: Ox PBS, pH7.2) followed by size exclusion chromatography (SEC). Fractions from the SEC were run on SDS-PAGE and the proteins were visualized by Coomassie blue staining. Fractions containing high levels of uricase were combined for further analyses. FIG. 8A shows the Coomassie Blue stained SDS-PAGE from the purified preparations relative to His tagged construct (labeled SGD). Variants 1 and 3 were found to have the N-terminal methionine processed (removed), whereas variant 2 was found to have the N-terminal methionine retained. All processing appeared uniform.

Figure 8B:
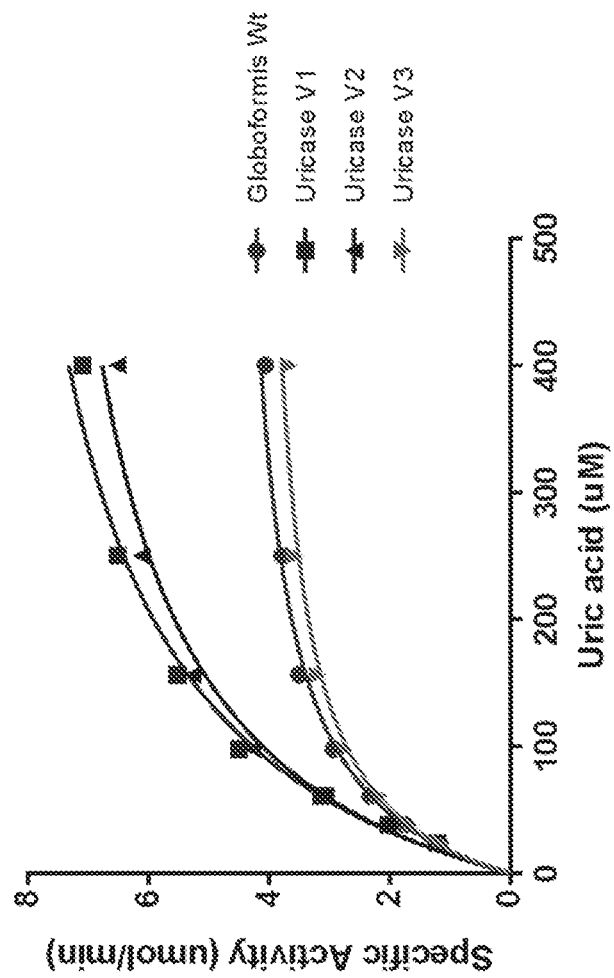
FIGS. 8A-B depict the analysis of various N-terminal uricase truncations.
Figure 8A:
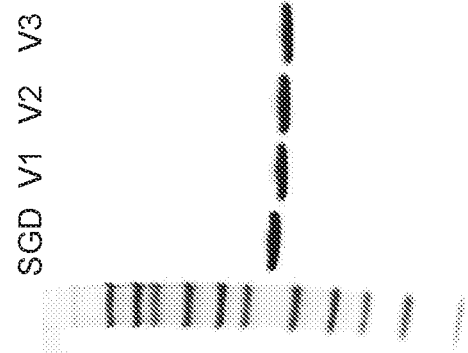

FIG. 8B shows the activity of V1, V2 and V3. Variant 1 and 2 had considerably better activity than variant 3. Variant 1 was selected for further development.

Example 9. Specific PEGylation

Modification of therapeutic proteins with polyethylene glycol (PEG) can be performed as either random attachment to selected protein residues (e.g. lysine side chains), or site-specific to a unique predetermined site. The latter approach has the advantage that the conjugation chemistry can be better controlled and manufactured consistently, yielding a highly homogenous PEGylated product with defined bioactivity. Among methods for site-specific attachment, the most widely used approach is coupling to unpaired cysteine residues, and this generally involves the introduction of one or more free cysteine residues into the protein sequence. Sites for Cys introduction can be carefully selected to avoid any negative impact on bioactivity or biophysical properties of the conjugate product following modification with PEG.

The *Arthrobacter globiformis* uricase sequence described in SEQ ID NO: 27 is particularly well suited for cysteine-based site-specific modification as it contains only one native C-terminal Cys residue. The C-terminal region was truncated (SEQ ID NOs: 18 and 20) so the protein contains no Cys. Thus, modification of this protein by Cys-reactive reagents is easily confined to sites where Cys residues have been introduced. To select potential sites for Cys residue introduction in the *Arthrobacter globiformis* uricase sequence, the following criteria were taken into consideration i. Sites must be on a solvent-exposed surface of the protein to ensure efficient reaction with a thio-reactive PEG reagent;
ii. Sites must be not be close to the enzyme active sites to avoid the risk of impacting activity; and
iii. Sites must not be in close proximity to each other so that PEGylation of one site does not sterically hinder PEGylation of other sites.

Moreover, given the tetrameric nature of uricase, intra- and inter-subunit distances ideally should be considered in the case of ii. and iii.

In order to compute parameters relevant to these considerations, a three-dimensional structure of the *Arthrobacter globiformis* uricase was used. A limited number of different uricase structures have been reported, and one of these is the crystal structure of *Arthrobacter globiformis* uricase bound to uric acid substrate (PDB accession code: 2YZB) (see FIG. 10A). The atomic coordinates for this structure were used to compute the following set of parameters:

i. Solvent accessible area surface area for each amino acid residue within this uricase and
ii. Atomic distances between each side chain Cα atom and the C5 atom of the uric acid substrate (Cα-C5 distance).

To identify preferred positions within the *Arthrobacter globiformis* uricase for substitution with cysteine, the following criteria were initially set. First, residues were identified with total solvent accessible surface area $>100$ Å$^2$ and which with a Cα-C5 distance $>25$ Å (i.e. to each C5 in the 4 uric acid molecules bound to the uricase tetramer). Second, as a further restriction, for any given uricase residue, these criteria had to be met in all four subunits. Of the 287 amino acid residues in each uricase subunit, only 9 satisfied these criteria. These were Thr11; Asn33; Asn119; Asp120; Ser142; Glu196; Pro238; Glu286 and Arg289. The third criteria were then considered by calculating the matrix of atomic distances between pairs of Cα atoms within this set of residues across the tetrameric structure (see Table 6). From this analysis, Thr11, Asn33, Glu196 and Asn119 were selected as preferred residues for substitution with cysteine, as their Cα atoms across the tetramer are well separated ($\geq 19.5$ Å for all pairs).

Table 6 below is a matrix showing atomic distances (in Å) between selected Cα atoms in uricase structure 2YZB. Subunits are by a letter, i.e. -A, -B, -C, -D. Due to the highly symmetric nature of the tetramer, the set of distances below suffices to characterize all distance pairs across the tetramer (example: T11-A to T11-B distance is equivalent to T11-C to T11-D; T11-A to T11-C is equivalent to T11-B to T11-D; T11-A to T11-D is equivalent to T11-B to T11-C).

TABLE 6

Matrix showing atomic distances (in Å)

| | T11-A | N33-A | N119-A | D120-A | S142-A | E196-A | P238-A | E286-A | R289-A |
|---|---|---|---|---|---|---|---|---|---|
| T11-A | 0 | 62.2 | 67.2 | 66.4 | 35.5 | 47.3 | 48.6 | 43.1 | 35.4 |
| N33-A | | 0 | 20.7 | 17.5 | 35.4 | 27.4 | 35.9 | 46.3 | 43.6 |
| N119-A | | | 0 | 3.8 | 45.8 | 35 | 37.6 | 46.6 | 46.5 |
| D120-A | | | | 0 | 43.3 | 32.2 | 35.5 | 45.1 | 44.9 |
| S142-A | | | | | 0 | 15 | 21.8 | 24.7 | 17.3 |

TABLE 6-continued

Matrix showing atomic distances (in Å)

| | T11-A | N33-A | N119-A | D120-A | S142-A | E196-A | P238-A | E286-A | R289-A |
|---|---|---|---|---|---|---|---|---|---|
| E196-A | | | | | | 0 | 11.5 | 21.1 | 18.7 |
| P238-A | | | | | | | 0 | 11.9 | 14.5 |
| E286-A | | | | | | | | 0 | 9 |
| R289-A | | | | | | | | | 0 |
| T11-B | 68.2 | 72 | 62.3 | 65 | 79.1 | 79 | 79.8 | 80.1 | 76.8 |
| N33-B | 71.3 | 52.9 | 35.1 | 37.3 | 59.8 | 49.5 | 43.2 | 45 | 49.3 |
| N119-B | 61.3 | 34.7 | 22 | 22.3 | 41.5 | 29.5 | 24.9 | 30.8 | 34.3 |
| D120-B | 64.1 | 36.9 | 22.3 | 23.1 | 45.3 | 33.3 | 28.5 | 34.1 | 37.8 |
| S142-B | 79.8 | 60.6 | 42.8 | 46.5 | 76.4 | 69.6 | 68.3 | 71.2 | 71.5 |
| E196-B | 79.2 | 49.6 | 29.8 | 33.6 | 68.8 | 59.5 | 58.2 | 63 | 64.3 |
| P238-B | 80.2 | 43 | 24.8 | 28.5 | 67.2 | 58 | 58.9 | 65.4 | 65.7 |
| E286-B | 80.9 | 44.8 | 30.6 | 33.9 | 70.3 | 62.9 | 65.4 | 71.9 | 70.8 |
| R289-B | 77.7 | 49.2 | 34.4 | 37.8 | 70.7 | 64.3 | 66 | 71.1 | 69.9 |
| T11-C | 83.5 | 42.7 | 27.2 | 30.5 | 69.9 | 61.2 | 63.5 | 70.7 | 70.3 |
| N33-C | 43.5 | 54 | 58.5 | 58.7 | 53.7 | 60.1 | 66.1 | 67.6 | 60.3 |
| N119-C | 28 | 58.6 | 59.7 | 60.1 | 48.2 | 55.5 | 58.3 | 56.3 | 49.5 |
| D120-C | 31.2 | 58.8 | 60.1 | 60.6 | 50.3 | 57.5 | 60.7 | 59.3 | 52.4 |
| S142-C | 71.2 | 53.6 | 47.5 | 49.7 | 71.1 | 69.5 | 73.7 | 78.1 | 74.1 |
| E196-C | 61.9 | 60.8 | 56.1 | 58 | 69.9 | 71.2 | 74.8 | 76.8 | 71.9 |
| P238-C | 63.8 | 66.4 | 58.7 | 61.1 | 73.9 | 74.5 | 76.4 | 77.3 | 73.3 |
| E286-C | 70.9 | 67.9 | 56.7 | 59.6 | 78 | 76.5 | 77.2 | 78.4 | 75.7 |
| R289-C | 70.7 | 60.8 | 49.9 | 52.8 | 74.1 | 71.8 | 73.4 | 75.9 | 73.1 |
| T11-D | 50.9 | 44.3 | 43.4 | 41.8 | 28.6 | 20.4 | 9.1 | 8.2 | 16 |
| N33-D | 44.2 | 74.8 | 66.8 | 68.4 | 63.8 | 66.4 | 62.9 | 57.1 | 54.8 |
| N119-D | 44 | 66.6 | 60.6 | 62.3 | 61.9 | 65.1 | 65.1 | 62.5 | 58.2 |
| D120-D | 42.4 | 68.4 | 62.4 | 64 | 61.7 | 65.3 | 64.8 | 61.6 | 57.3 |
| S142-D | 27.5 | 63.6 | 61.9 | 61.6 | 38.5 | 43.2 | 37.8 | 27.9 | 25.6 |
| E196-D | 19.5 | 66.5 | 65.4 | 65.5 | 43.9 | 51 | 48.5 | 40.8 | 36.1 |
| P238-D | 8.5 | 63 | 65.4 | 65 | 38.9 | 48.7 | 48.7 | 42.5 | 35.7 |
| E286-D | 6.3 | 57.5 | 63.1 | 62 | 29.4 | 41.3 | 42.8 | 37.5 | 29.5 |
| R289-D | 13.8 | 55.1 | 58.8 | 57.8 | 26.7 | 36.4 | 35.9 | 29.4 | 22.1 |

Example 10. Cysteine Containing Variants of Uricase for Site-Specific PEGylation A number of different combinations of 1, 2, 3, and 4 Cys residues per uricase monomer were generated. These were analyzed for expression, solubility, purity, and activity both before and after PEGylation. Due to the solvent exposed nature of the Cys, these constructs tend to aggregate (disulfide bond) unless they are kept under reducing conditions. This necessitates that a reducing agent (DTT or other) be present during purification and assay procedures. Once the Cys has been PEGylated, reducing agent is no longer necessary. All tested permutations of Cys containing constructs could be expressed, purified and demonstrated good activity both before and after PEGylation.

Figure 9A:
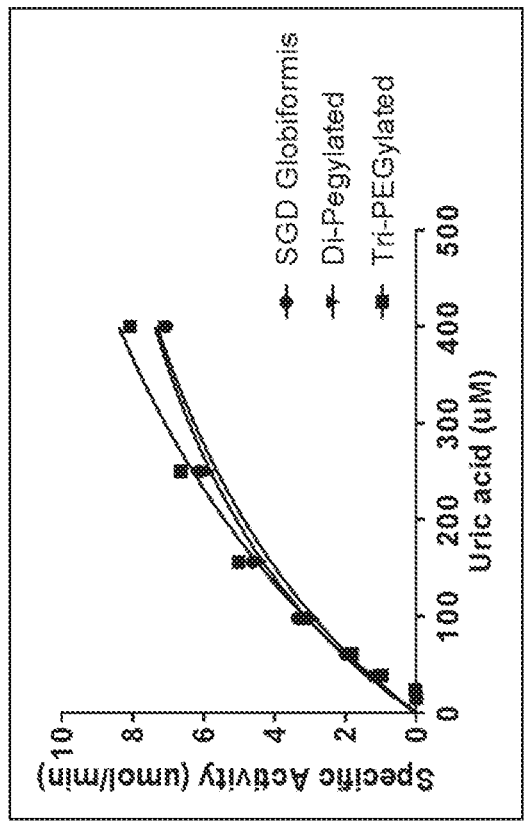
FIGS. 9A-B are line graphs that depict the results of uricase activity assays at a variety of substrate (UA) concentrations. The solid lines depict a Michaelis-Menten kinetic fit.
Figure 10B:
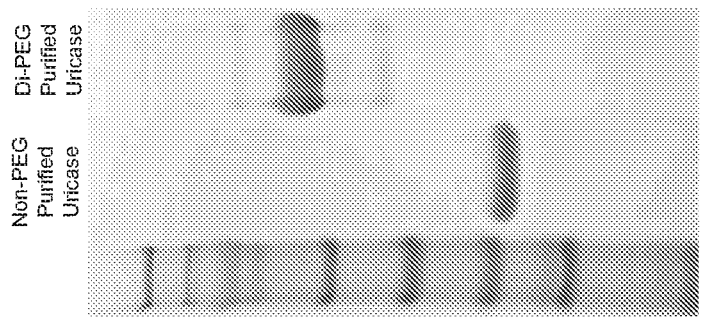
FIGS. 10A-D depict the analysis of di-pegylated uricase.
Figure 10A:
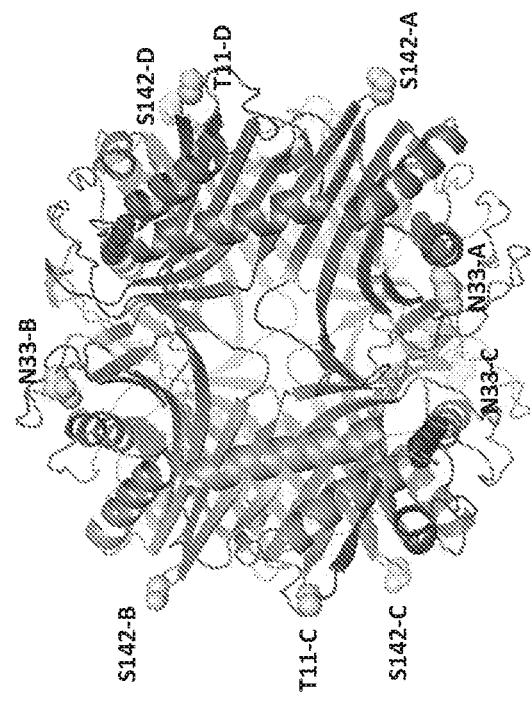

FIG. 10A shows the three dimensional solvent accessible sites within the tetrameric crystal structure of *Arthrobacter globiformis* uricase (PDB accession code: 2YZB) (1). Each uricase monomer subunit of the tetrameric enzyme is shown, and residues selected for substitution with cysteine (T11, N33, S142) are identified. These side chains are highly surface exposed, distant from each other, and distant from each active site within the tetramer. Two Cys containing variants (T11C, N33C (SEQ ID NO: 17) and T11C, N33C, S142C (SEQ ID NO: 16)) were analyzed for expression, solubility, purity, and activity both before and after PEGylation. FIG. 9A shows non-Cys (SEQ ID NO: 20), di-Cys (T11C, N33C) (SEQ ID NO: 17) and tri-Cys (T11C, N33C, and S142C) (SEQ ID NO: 16) uricase activity. All assays are run in the presence of DTT to eliminate the potential for disulfide bonding.

Example 11. Optimizing PEGylation

Long-term suppression of UA by uricase requires that the molecule be modified in some fashion to extend half-life. Commercially available rasburicase, which is not PEGylated and contains no conjugate half-life extending properties, has a half-life in humans of 16-21 hours requiring daily IV dosing for tumor lysis syndrome (Ueng et al 2005). PEGylation has been employed to extend the half-life of a number of uricases preclinically. Krystexxa® is a hyper-PEGylated uricase that contains ~44×10 kDa PEG molecules (~440 kDa of total PEG per tetramer) conjugated to the surface of active tetramer. Based on the literature, during the early development of Krystexxa® it was hypothesized that PEG would effectively mask the uricase, which is a foreign protein, and make it less immunogenic (Hershfield et al, 2010 PNAS). Preclinical studies were performed to maximize the amount of PEG on the surface of the uricase while retaining enzymatic activity. 44×10 kDa PEG per tetramer was found to be the maximum amount of PEG that could be conjugated to the uricase and retain enzymatic activity. The PEG conjugation was achieved by randomly PEGylating primary amines. Clinical data from the Krystexxa® trials demonstrate that ~90% of patients develop and anti-Krystexxa® drug response (Lipsky et al 2014 Arthritis Research & therapy). A large percentage of the anti-drug response appears to be to PEG and not the protein. Most compelling, is the fact that antibodies from patients that developed an anti-drug (PEG) response bind to non-uricase PEGylated proteins demonstrating that the response is against PEG and not the protein or protein-PEG interface. Prior to these trials, conventional wisdom was that the PEG motif of a PEGylated therapeutic was unlikely to be immunogenic. The vast majority of PEGylated therapeutics contain only enough PEG to extend half-life and are not "hyper-PEGylated" like Krystexxa®. One hypothesis is that the amount of PEG on Krystexxa® has led to the anti-PEG immunogenicity associate with the drug. The Krystexxa® tetramer is about 136 kDa with approximately 440 kDa of PEG conjugated to the surface. This leads to a ~576 kDa molecule, a size that is unprecedented for PEGylated therapeutics. As a result, a limited number of Cys residues for site specific PEGylation were engineered, as described in Example 10.

Uricases with either two (di-cys) or three (tri-cys) cysteines were generated initially with a His tag for purification ease. FIG. 9A shows that these di-cys and tri-cys uricases retain uricase enzymatic activity.

Di-PEGylation reaction conditions were optimized by varying time, pH, phosphate concentration, NaCl, protein, PEG and TCEP. Higher PEG concentrations were shown to improve PEGylation efficiency and higher TCEP concentration decreased PEGylation efficiency slightly. Other variables had very little effect on PEGylation efficiency. Table 7 below shows the variables that were tested to optimize PEGylation and the optimum conditions achieved.

TABLE 7

Optimization of PEGylation

| Factor | Range studied | Effect | Optimum |
|---|---|---|---|
| pH | 6.5-7.5 | Little effect | pH 7 |
| Phosphate conc. | 20 mM-100 mM | Little effect | 60 mM |
| Protein conc. | 1-5 mg/ml | Little effect | 1-3 mg/ml |
| PEG conc. | 50-1000 uM | Pronounced effect | 700-900 uM |
| TCEP conc | 0-500 uM | Clear effect | No TCEP |
| Reaction time at 4° C. | 10 mins-4 hrs | Reaction complete after 1.75 hrs | |

Figure 9B:
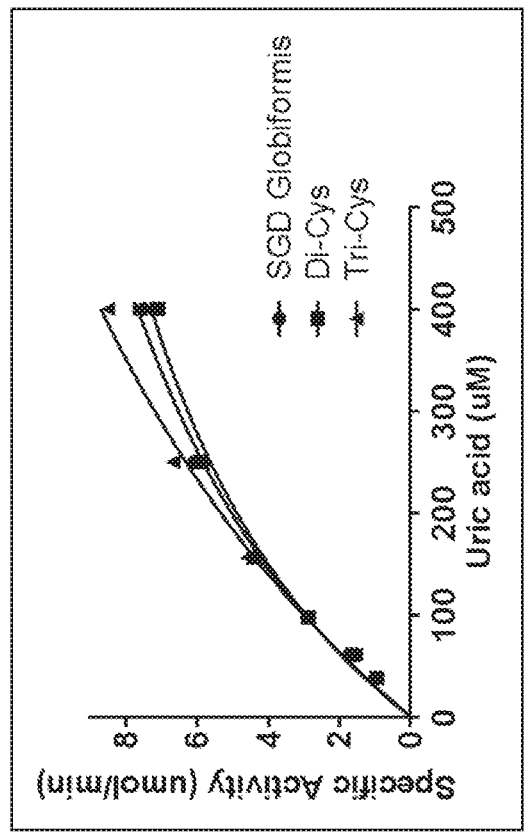

FIG. 9B shows that the di-PEGylated and tri-PEGylated uricases retain uricase enzymatic activity.

Figure 10D:
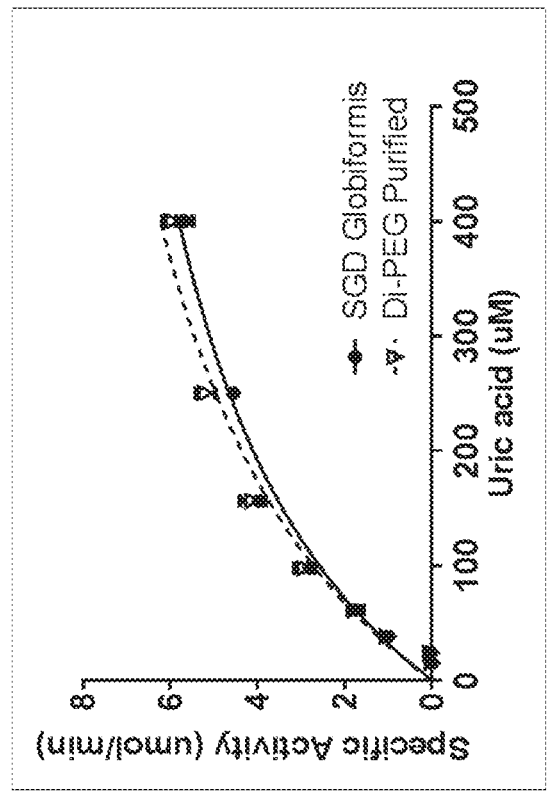
Figure 10C:
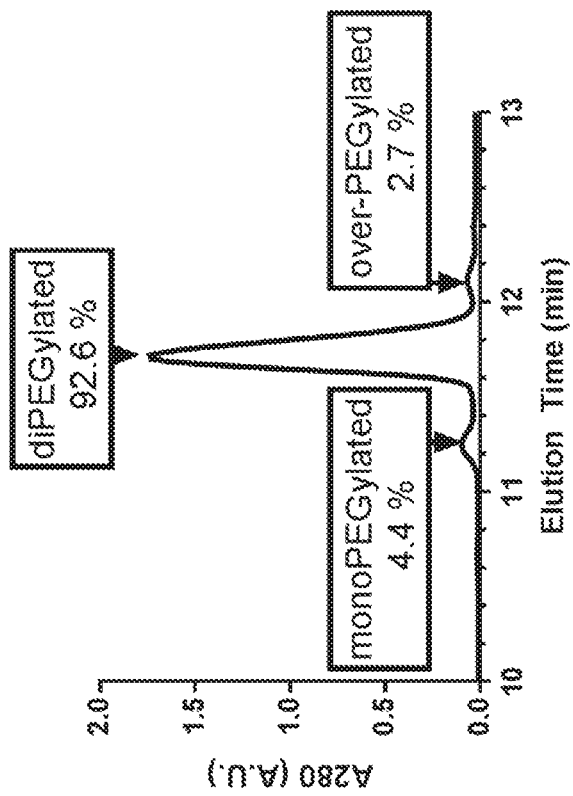

Analysis of di-PEGylated material by SDS-PAGE (FIG. 10B) confirmed that most of the protein was uniformly conjugated with PEG. Reverse phase chromatography analysis of the di-PEGylated material suggested that 92.6% was di-PEGylated, 4.4% mono-PEGylated and a small amount of material over-PEGylated (~3%) was observed (FIG. 10C). PEGylation did not appear to impact the enzymatic activity. Di-PEGylated material showed a similar rate of UA oxidation compared to the non-PEGylated enzyme (FIG. 10D). Comparable results were obtained for the tri-PEGylated material (data not shown). These methods of analysis disrupt the quaternary structure of the uricase, but as a homo-tetramer the predominant native state product for the di-PEG uricase would be expected to have 8×10 kDa PEG chains, while the tri-PEG uricase would be expected to have 12×10 kDa PEG chains.

Based on the optimized PEGylation conditions identified (see Table 7), non-his tagged di-PEG and triPEG uricases were generated, purified and analyzed for PEGylation efficiency and enzyme activity. These PEGylated molecules were further analyzed in vivo PK studies.

Example 12. In Vivo PK for Di-PEG and Tri-PEG Uricases

Two PEGylated uricases (di-PEG T11C, N33C and tri-PEG T11C, N33C, and S142C) were evaluated in a rat study. A rat study was chosen because there was precedence in testing PK of PEGylated uricases in rats (Zhang et al, 2012 International Journal of Pharmaceutics). SEQ ID NOs: 16 and 17 were used in this assay. In vivo pharmacokinetics were determined in rat for both di-PEGylated and tri-PEGylated uricases. 4 rats in each group were dosed IV at 5 mg/kg and 10 samples were collected (Day-1), 0.5, 2, 4, 8, 24, 48, 72, 96 and terminal at 144 hours post injection. Whole blood was collected in serum separator tubes and frozen. Serum was analyzed for residual uricase activity and data were fit to a titration curve. The enzymatic specific activity of the uricase that went into the rats (predose) and the uricase that was measured from serum (postdose) was comparable suggesting activity was retained during the in vivo study. FIG. 11A demonstrates that di and tri-PEGylated uricases have substantially longer half-lives than the non-PEGylated uricase. Non-PEGylated uricase had a half-life of 2-3 hours in this study (FIG. 11A, triangles). Both di- and tri-pegylated uricases exhibit mono-phasic profiles. The half-lives, volume of distribution (Vd) and clearance rate for each uricase are shown in Table 8 below. Coefficient of variation is expressed as a percentage within the parentheses.

TABLE 8

Rat PK for Di-PEGylated and Tri-PEGylated uricase

| | Half-Life (hr) | Vd (L/kg) | Clearance (L/hr/kg) |
|---|---|---|---|
| Di-PEGylated | 22.8 (7.4) | 0.03 (7.2) | 0.00096 (8.1) |
| Tri-PEGylated | 29.9 (12.1) | 0.03 (25) | 0.00077 (12.8) |

The results shown in Table 8 indicate that di-PEG and tri-PEG showed very similar pharmacokinetic profiles with a slight advantage of tri-PEG over di-PEG. However, di-PEG was considered to be slightly more desirable with respect to manufacturing and analysis, and therefore, the di-PEG Ti IC, N33C was selected for further testing. With substantially less PEG than Krystexxa®, the di-PEGylated uricase may be advantageous from an immunogenicity standpoint.

The pharmacokinetic behavior of Krystexxa® also was evaluated in the same rat PK study. Unlike the di- and tri-PEGylated uricases, Krystexxa® did not exhibit mono-phasic elimination, but a complex profile in which Krystexxa® was rapidly eliminated in the first 2 hours followed by a more gradual elimination profile (FIG. 11A, squares). The Krystexxa® elimination profile is distinctly different from that of the di and tri-PEGylated uricases.

The PK of di-PEGylated uricase administered SC was studied in canines.

Figure 11B:
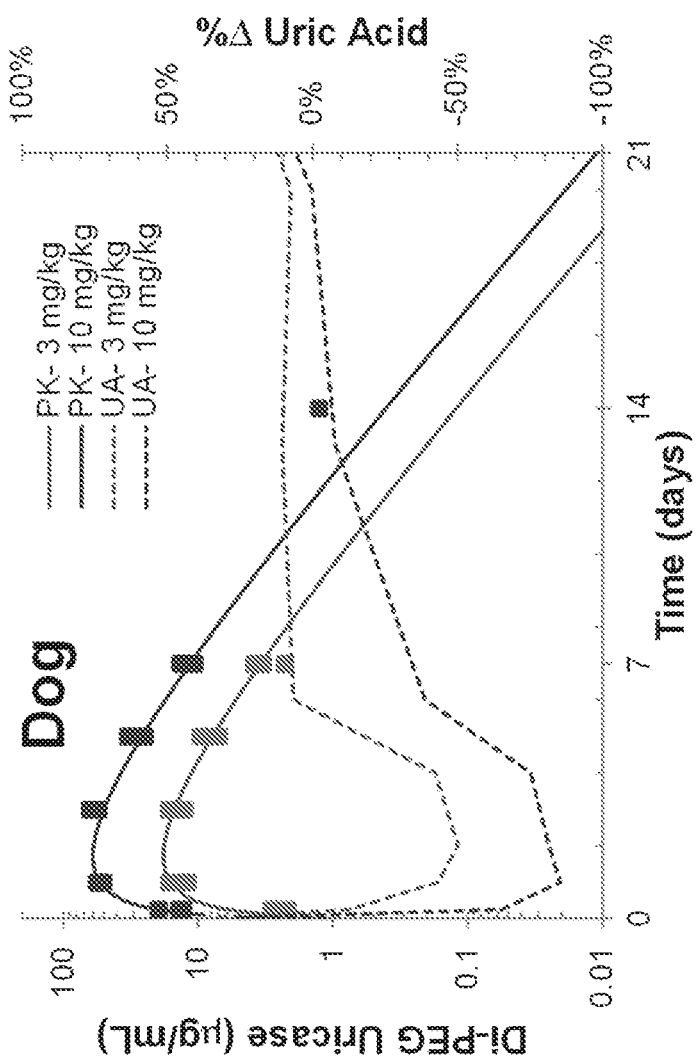

A canine study was chosen because there was precedence for testing PK of PEGylated uricase in canines (Pegloticase/Krystexxa® FDA BLA No. 125293, section 2.6.5.4.1). Canines were dosed SC at 3 and 10 mg/kg and serum or blood samples were collected at various time points and analyzed for uricase activity (PK) or uric acid (PD). The enzymatic specific activity of the uricase that went into the canines (predose) and the uricase that was measured from serum (postdose) was comparable suggesting activity was retained during the in vivo study. FIG. 11B demonstrates that di-PEGylated uricase delivered to canines via SC route of administration had a half-life of 1.81±0.31 days for 3 mg/kg (n=3) and 1.82±0.22 days for 10 mg/kg (n=3). A substantial reduction (~85%) in UA levels was observed and appears to be proportional to serum uricase levels (FIG. 11B). Blood UA levels returned to normal as the uricase levels were depleted.

Example 13. Ex Vivo Evaluation of Activity and Stability

Figure 12B:
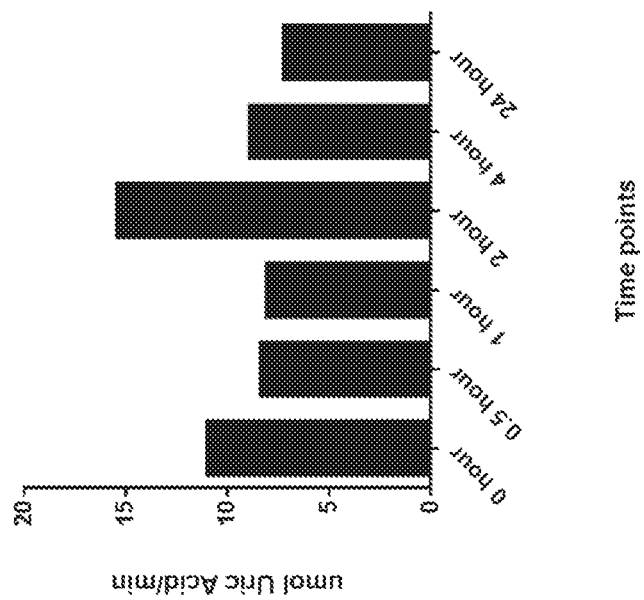
FIGS. 12A-C depict the ex vivo human serum-based analysis of di-PEGylated uricase activity and stability.
Figure 12A:
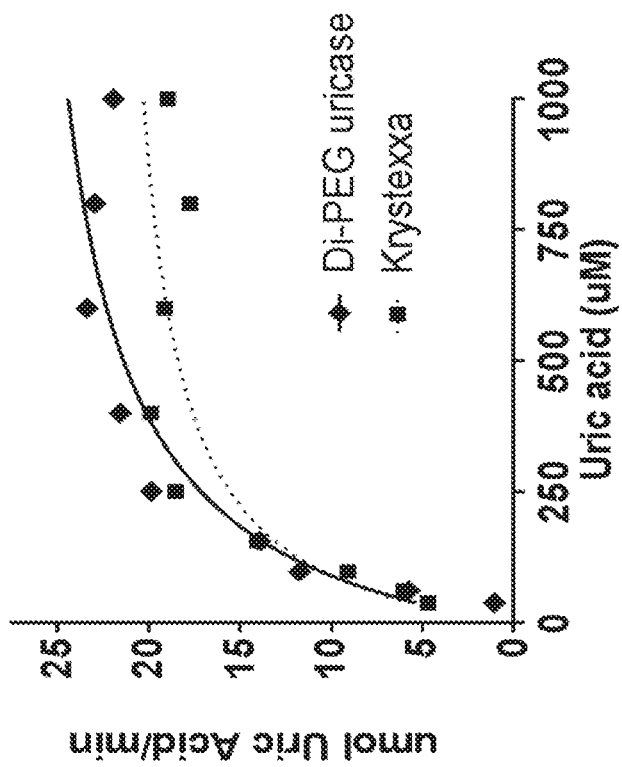

Di-PEG uricase (SEQ ID NO: 1) activity was evaluated in 50% human serum (whole blood is ~50% serum) at 37° C. to mimic the complex in vivo matrix environment and temperature. The assay was performed as follows: UA, phosphate buffer, and serum were warmed to 37° C. All reaction steps were done at 37° C. Uricase was diluted to 8 ug/mL in serum for 20-30 minutes to deplete endogenous uric acid in the human serum sample. An equal volume of a titration of UA in phosphate buffer was then added and the reaction was stopped at 0, 1, 2, 4 or 6 minutes using 50% percholoric acid. Perchloric acid has been shown to precipitate protein but does not precipitate the UA (Sakuma et al, 1987 Clinical Chemistry and Stove et al, 2007 Clinical Chemistry). The precipitate was pelleted and 100 uL of the supernatant was transferred to a UV plate. Absorbance was measured at 292 nM. Rate was calculated by plotting the slope of the 4 time-points at each UA concentration using SoftMax Pro software. FIG. 12A show the comparison of di-PEGylated uricase activity and Krystexxa® in 50% human serum at 37° C.

A human serum based stability assay was performed as well. Di-PEGylated uricase was incubated in 50% human serum for 0, 0.5, 1, 2, 4, or 24 hours at 37° C. and then assayed for activity. Di-PEG uricase retains activity at each point suggesting that the protein is stable in 50% human serum for at least 24 hours and retains its UA oxidase activity. FIG. 12B shows the results from the serum stability experiment.

Figure 12C:
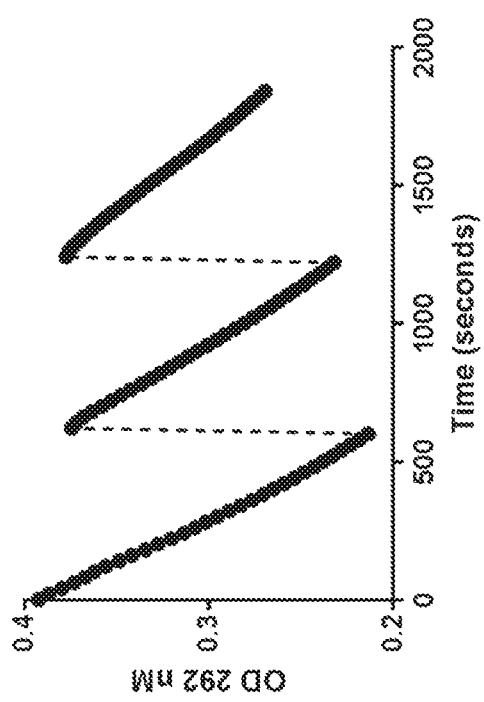

Lastly, the activity of di-PEGylated uricase was explored with repeat doses (recharge) of UA at 37° C. In short, UA (100 µM) and di-PEG uricase (1 µg/ml) were combined in a 100 µL volume (UV transparent 96 well plate) at 37° C. Absorbance at 292 nm was monitored for 10 minutes. 2.5 µL of 2000 uM UA was added to the 100 µL wells ("recharge") and the absorbance at 292 nm was monitored for an additional 10 min. The process was repeated and activity (slope of UA depletion) remained relatively constant for each "recharge". FIG. 12C shows the results from this study.

Example 14. PEG Conjugation Efficiency Determination

When multiple conjugation sites are present in a biomolecule, conjugation reactions frequently lead to a heterogeneous mixture of products that are characterized by varying degrees of functionalization and/or different sites of modification. This is generally the case for first generation, non-specific coupling chemistries, such as protein conjugations targeting ε-amino groups of lysine residues. However, even when a site-specific conjugation approach is chosen, for example in the frequently employed approach of targeting engineered cysteine residues, the reaction might not go to completion, e.g. due to steric constraints. This likewise results in a distribution of conjugated proteins with varying degree of derivatization. As bioactivities can vary significantly with the degree of modification, the final product needs to be thoroughly characterized in terms of modification to ensure a well-defined and consistently manufactured bioconjugate.

Several analytical approaches can be employed to characterize the overall derivatization of bioconjugates, including mass spectrometry or HPLC-based methods. However, for the important class of bioconjugations that involve the attachment of polymers like poly(ethylene glycol) (PEG) to proteins, most of these techniques become challenging for conjugates containing multiple attached polymers. Due to the size and charge distribution of polymer and protein, as well as polydispersity of the PEG, mass spectrometry approaches based on electrospray ionization (ESI) are generally not feasible, and MALDI MS frequently results in a broad continuous mass spectrum. For smaller PEGylated proteins and/or in the case of a low number of conjugation sites (N<3), HPLC-based techniques under native conditions (based on size-exclusion or ion exchange) may still provide sufficient resolution to distinguish individual species. However, these techniques are generally not feasible or not sufficiently resolved in the case of larger proteins with multiple conjugation sites. The heavily hydrated PEG polymer imparts a large hydrodynamic radius on the protein conjugates which prevents SEC-based separation of sufficient resolution, and the shielding of surface charges weakens electrostatic interactions with IEX resins. In this case, Reversed Phase (RP) HPLC is frequently the method of choice for accurate reaction monitoring and product characterization. However, in the case of oligomeric proteins, this technique generally leads to a dissociation of subunits and provides only a description of the monomeric unit which affords a partial understanding of molecule functionalization that can be misleading for process optimization efforts. To accurately quantify the true conjugation status of an oligomeric biotherapeutic for process optimization and product characterization, an understanding of the relationship between the extent of modification at the monomer level and the resulting overall derivatization at the quaternary level must be derived.

Experimental Design:

Maleimide-functionalized PEG-10 (10 kDa, Sunbright MA-100) was obtained from NOF. All buffer components and reagents were purchased from Sigma (St Louis, Mo.) or Avantor Performance Materials (Center Valley, Pa.). PEGylation reactions of tri-cys uricase were performed in sodium phosphate buffer, pH 7.0. PEGylation reactions were quenched after selected timepoints by the addition of DTT to a final concentration of 10 mM and analyzed by analytical reverse-phase high performance liquid chromatography RP HPLC (RP-HPLC) using a YMC-Pack Protein-RP column (250×2.0 mm, S-5 µm) from YMC America (Allentown, Pa., USA) with an Agilent HPLC1200 system. Mobile phase A was 0.1% TFA in water and mobile phase B consisted of 0.1% TFA in acetonitrile. The sample was eluted with a linear gradient of increasing mobile phase B at a flow rate of 0.4 ml/min. Elution profiles were monitored by UV absorbance at 280 nm.

A two-step Box-Behnken design was employed with the goal to maximize protein PEGylation. The concentration of protein (1-3 mg/ml), PEG-10 (0.5-1 mM) and reducing agent TCEP (0-0.5 mM) were varied for di-cys and tri-cys uricases containing 8 or 12 conjugation sites per tetramer, respectively, while pH, salt and phosphate buffer ion concentration were kept at fixed values. Data were analyzed after selected time points ranging from 10 minutes to 4 hours. All second order effects as well as time were treated as categorical variables, yielding a design of 64 experiments for screening studies for each protein variant in round 1 and 60 additional experiments per protein variant for the second round of optimization studies. Data analysis was performed with the software JMP 10.

Statistical Model:

A statistical measure for deriving the overall derivatization of an oligomeric protein from data obtained from readily accessible assays (like Reverse Phase (RP) HPLC) that cause non-covalently associated subunits to dissociate was generated. For a protein (or biomolecule) containing n subunits, which has m potential conjugation sites in each subunit. Let $p_i$, with $i=0, \ldots, m$, be the experimentally observed proportion of the subunits that have i conjugated sites, then $\Sigma_{i=0}^{m} p_i = 1$. The probability, $q_j$, of observing an oligomeric protein with j total conjugated sites can be summarized using the following multinomial probability table.

TABLE 9

| Total Conjugated Sites | Probability |
|---|---|
| 0 | $q_0 = p_0^n$ |
| 1 | $q_1 = n p_0^{n-1} p_1$ |
| 2 | $q_2 = \binom{2}{n} p_1^2 p_0^{n-2} + n p_2 p_0^{n-1}$ |
| . | . |
| . | . |
| . | . |

TABLE 9-continued

| Total Conjugated Sites | Probability |
|---|---|
| J | $q_j = \sum_{0k_0+1k_1+\ldots+mk_m=j} \binom{k_0}{n}\binom{k_1}{n-k_0} \cdots \binom{k_{m-1}}{k_{m-1}+k_m} \prod_{i=0}^{m} p_i^{k_i}$ |
| . | . |
| . | . |
| . | . |
| n × m | $q_{n \times m} = p_m^n$ | where $k_i$, $i=0, \ldots, m$, are the number of subunits that have exactly i conjugated sites and the ensemble of these subunits has total j conjugated sites and $\Sigma_{j=0}^{n \times m} q_j = 1$. The mean overall derivatization of the molecule is then readily written as:

$$\text{Derivatization}_{overall} = 1q_1 + 2q_2 + \ldots + jq_j + \ldots + n \times m \times q_{n \times m} \quad \text{(Eq. 1)}$$

Normalizing this value to the total number of available conjugation sites (n×m) yields the conjugation efficiency.

For the biochemically and pharmaceutically important classes of dimeric, trimeric, and tetrameric proteins, calculations are detailed below.

TABLE 10

Calculation of overall derivatization for a dimeric protein (n = 2) with m = 2 or 3 conjugation sites per subunit
1. Input of experimentally observed conjugation per subunit into table in Excel as follows:

| | A | B | C | D | E |
|---|---|---|---|---|---|
| 1 | $P_0$ | $P_1$ | $P_2$ | $P_3$ | Sum Check |
| 2 | | | | | =SUM(A2:D2)* | p0, p1, . . . p3: Experimentally observed proportions of subunits with 0, 1, . . . 3 conjugated molecules.
For m = 2 conjugation sites per subunit, complete fields A2, B2, C2; for 3 conjugation sites per subunit, complete fields A2, B2, C2, D2.
*: E2 = Sum Check =SUM(A2:D2). Total proportions need to add up to value of 1, e.g. 100%.

2. Calculations of Multinomial Probabilities and Overall Derivatization
Set up Excel table as follows:

| | A | B | C | D | E |
|---|---|---|---|---|---|
| 9 | Total Conjugated Sites j (from 0,1 . . . , (n×m)) | Probabilities $q_j$ | Expected Conjugations | Overall Derivatization | Conjugation Efficiency (%) |
| 10 | 0 | =A2^2 | =A10*B10 | =SUM(C10:C16) | =D10*100/(n×m)*** |
| 11 | 1 | =2*B2*A2 | =A11*B11 | | |
| 12 | 2 | =B2^2+2*C2*A2 | =A12*B12 | | |
| 13 | 3 | =2*C2*B2+2*D2*A2 | =A13*B13 | | |
| 14 | 4 | =C2^2+2*D2*B2 | =A14*B14 | | |
| 15 | 5 | =2*D2*C2 | =A15*B15 | | |
| 16 | 6 | =D2^2 | =A16*B16 | | |
| 17 | Sum Check | =SUM(B10:B16)** | | | |

If the protein has only m = 2 conjugation sites per subunit, fields B15 and B16 will not be populated.
*: Field B17 (SumCheck) needs to be =1
***: (n×m), the total number of conjugation sites, needs to be entered in numerical form here.

TABLE 11

Calculation of overall derivatization for a trimeric protein
(n =3) with m =2 or 3 conjugation sites per subunit
1. Input of experimentally observed
conjugation per subunit into table in Excel as follows:

|   | A | B | C | D | E |
|---|---|---|---|---|---|
| 1 | $P_0$ | $P_1$ | $P_2$ | $P_3$ | Sum Check |
| 2 |   |   |   |   | =SUM(A2:D2)* | p0, p1, ...p3: Experimentally observed proportions of subunits with 0, 1, ...3 conjugated molecules.
For m = 2 conjugation sites per subunit, complete fields A2, B2, C2; for 3 conjugation sites per subunit, complete fields A2, B2, C2, D2.
*: E2 = Sum Check =SUM(A2:D2). Total proportions need to add up to value of 1, e.g. 100%.

2. Calculations of Multinomial Probabilities and Overall Derivatization
Set up Excel table as follows:

|   | A | B | C | D | E |
|---|---|---|---|---|---|
| 9 | Total Conjugated Sites j (from 0,1 (nxm)) | Probabilities qj | Expected Conjugations | Overall Derivatization | Conjugation Efficiency (%) |
| 10 | 0 | =A2^3 | =A10*B10 | =SUM(C10:C19) | =D10*100/(nxm)*** |
| 11 | 1 | =3*B2*A2^2 | =A11*B11 |   |   |
| 12 | 2 | =3*B2^2*A2+3*C2*A2^2 | =A12*B12 |   |   |
| 13 | 3 | =B2^3+6*C2*B2*A2+3*D2*A2^2 | =A13*B13 |   |   |
| 14 | 4 | =3*C2^2*A2+6*D2*B2*A2+3*C2*B2^2 | =A14*B14 |   |   |
| 15 | 5 | =3*D2*B2^2+6*D2*C2*A2+3*B2*C2^2 | =A15*B15 |   |   |
| 16 | 6 | =3*D2^2*A2+6*B2*C2*D2+C2^3 | =A16*B16 |   |   |
| 17 | 7 | =3*D2^2*B2+3*D2*C2^2 | =A17*B17 |   |   |
| 18 | 8 | =3*D2^2*C2 | =A18*B18 |   |   |
| 19 | 9 | =D2^3 | =A19*B19 |   |   |
| 20 | Sum Check | =SUM(B10:1319)** |   |   |   |

If the protein has only m = 2 conjugation sites per subunit, fields B17-B19 will not be populated.
**: Field B20 (SumCheck) sum needs to be = 1
***: (nxm), the total number of conjugation sites, needs to be entered in numerical form here.

TABLE 12

Calculation of overall derivatization for a tetrameric
protein (n = 4) with m =2 or 3 conjugation sites per subunit
1. Input of experimentally observed conjugation per subunit into table in
Excel as follows:

|   | A | B | C | D | E |
|---|---|---|---|---|---|
| 1 | $P_0$ | $P_1$ | $P_2$ | $P_3$ | Sum Check |
| 2 |   |   |   |   | =SUM(A2:D2)* | p0, p1, ...p3: Experimentally observed proportions of subunits with 0, 1, ...3 conjugated molecules.
For m = 2 conjugation sites per subunit, complete fields A2, B2, C2; for 3 conjugation sites per subunit, complete fields A2, B2, C2, D2.
*: E2 = Sum Check =SUM(A2:D2). Total proportions need to add up to value of 1, e.g. 100%.

2. Calculations of Multinomial Probabilities and Overall Derivatization
Set up Excel table as follows:

| | A | B | C | D | E |
|---|---|---|---|---|---|
| 9 | Total Conjug. Sites j | Probabilities $q_j$ | Expected Conjugations | Overall Derivatization | Conjugation Efficiency (%) |
| 10 | 0 | =A2^4 | =A10*B10 | =SUM(C10:C22) | =D10*100/(nx m)ks: |
| 11 | 1 | =4*B2*A2^3 | =A11*B11 | | |
| 12 | 2 | =6*B2^2*A2^2+4*C2*A2^3 | =A12*B12 | | |
| 13 | 3 | =4*D2*A2^3+4*B2^3*A2+12*B2*C2*A2^2 | =A13*B13 | | |
| 14 | 4 | =6*C2^2*A2^2+B2^4+12*D2*B2*A2^2+12*C2*B2^2*A2 | =A14*B14 | | |
| 15 | 5 | =4*C2*B2^3+12*D2*C2*A2^2+12*D2*B2^2*A2+12*C2^2*B2*A2 | =A15*B15 | | |
| 16 | 6 | =6*C2^2*B2^2+24*A2*B2*C2*D2+4*D2*B2^3+6*D2^2*A2^2+4*C2A3*A2 | =A16*B16 | | |
| 17 | 7 | =12*D2*C2^2*A2+12*D2^2*B2*A2+4*C2^3*B2+12*D2*C2*82^2 | =A17*B17 | | |
| 18 | 8 | =C2^4+12*D2*B2*C2^2+12*D2^2*C2*A2+6*D2^2*B2^2 | =A18*B18 | | |
| 19 | 9 | =4*C2^3*D2+4*D2^3*A2+12*D2^2*C2*B2 | =A19*B19 | | |
| 20 | 10 | =4*D2^3*B2+6*D2^2*C2^2 | =A20*B20 | | |
| 21 | 11 | =4*D2^3*C2 | =A21*B21 | | |
| 22 | 12 | =D2^4 | =A22*B22 | | |
| 23 | Sum Check | =SUM(810:822) | | | |

If the protein has only m = 2 conjugation sites per subunit, fields B19-1322 will not be populated.

**: Field B23 (SumCheck) sum needs to be = 1

***: (nxm), the total number of conjugation sites, needs to be entered in numerical form here.

The data above describes a statistical measure for deriving the overall functionalization of an oligomeric protein from the data obtained from readily accessible assays that cause non-covalently associated subunits to dissociate. The data above illustrates this method using the conjugation of a homo-tetrameric uricase protein with poly(ethylene glycol) (PEG) as a model system. The covalent modification of therapeutic proteins with PEG is now a well-established approach to increase the half-life in vivo, reduce immunogenicity, improve solubility and reduce susceptibility to proteolytic degradation. However, the method is equally applicable to other bioconjugation processes of oligomers which result in partial functionalization at a fixed number of conjugation sites.

Figure 13:
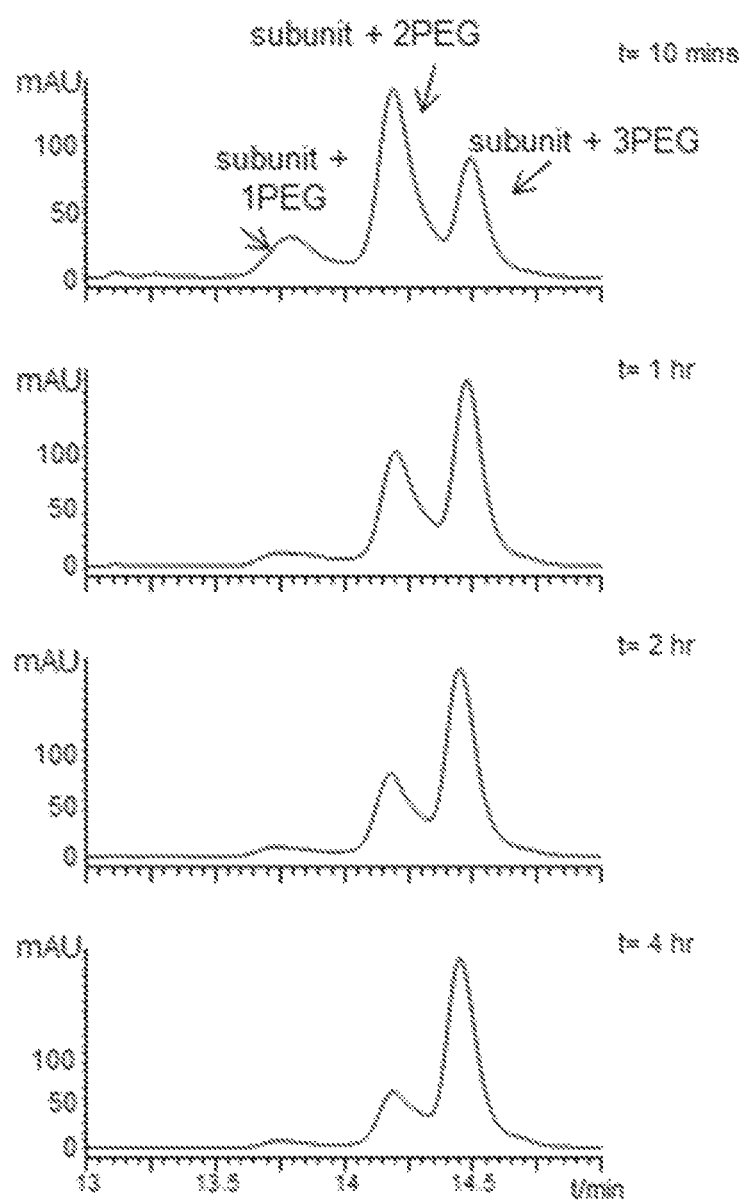
FIG. 13 depicts RP-HPLC analysis of pegylation efficiency at various incubation times. RP-HPLC was used to measure PEG conjugation, which results in well-resolved peaks that correspond to species with different degrees of conjugation.

The tetrameric uricase protein (n=4) studied here has a total mass >100 kDa. A fixed number of conjugation sites was introduced by engineering free cysteine residues that allow PEGylation with maleimide-functionalized PEG. The following discussion centers on the protein variant with m=3 conjugation sites per subunit, resulting in a total number of 12 possible conjugation sites for the tetramer. As described above, due to the size of the protein and the number of conjugation sites, all analytical tools that characterize the bioconjugate product with sufficient resolution are based on techniques that dissociate the non-covalently bound oligomer into individual subunits. FIG. 13 illustrates the reaction analysis over time using RP HPLC, which results in well-resolved peaks that correspond to species with different degree of conjugation that can readily be quantitated by integration. The assay outputs are, therefore, the relative amounts of monomer with different degrees of functionalization: the proportions p0, p1, p2, p3, of subunits containing 0, 1, 2, or 3 attached PEG chains. From these values, the individual probabilities q0, g1, q2, q3, . . . q12, are calculated for the tetrameric protein with 0, 1, 2, 3, . . . 12 attached PEG chains according to the above multinomial probability table as:

$$q_j = \sum_{0k_0 + 1k_1 + \cdots + 3k_3 = j} \binom{k_0}{4}\binom{k_1}{4-k_0} \cdots \binom{k_{3-1}}{k_{3-1}+k_3} \prod_{i=0}^{3} p_i^{k_i}$$

For this example, equation 1 then becomes:

Derivatization$_{overall}$ = $1q_1 + 2q_2 + 3q_3 + \ldots + 12q_{12}$.

Table 13 exemplifies this analysis and lists the relative amounts of differently PEGylated subunits as derived from RP HPLC analysis, together with the computed overall derivatization calculated from equation (1), and the PEGylation efficiency.

TABLE 13

Data analysis for the experiment illustrated in FIG. 13.

| | RP HPLC Assay Result | | | | Computed Overall Conjugation | |
| --- | --- | --- | --- | --- | --- | --- |
| Experimental Timepoint | UnPEGylated subunit [$p_0$, %] | Subunit + 1 PEG [$p_1$, %] | Subunit + 2 PEGs [$p_2$, %] | Subunit + 3 PEGs [$p_3$, %] | Overall derivatization according to equ. 1 (total conjugated sites) | Overall conjugation efficiency in %* |
| 10 minutes | 1.3 | 15.9 | 53.9 | 28.9 | 8.4 | 70.1 |
| 1 hour | 0.7 | 7.1 | 39.6 | 52.6 | 9.8 | 81.4 |
| 2 hours | 0.4 | 5.3 | 32.1 | 62.2 | 10.3 | 84.4 |
| 4 hours | 0 | 4.0 | 25.3 | 70.7 | 10.7 | 88.9 |

*This protein has a total of 12 possible conjugation sites.

The data illustrate that the computed overall derivatization is a valuable tool for process developers that allows immediately gauging the overall protein modification. For example, after the 10 minute time point the chosen reaction condition yields 28.9% of subunits with 3 (out of 3) functionalized conjugation sites. However, accounting for the fact that the remaining subunits are partially conjugated (15.9% with 1 PEG chain, 53.9% with 2 PEG chains) and feeding these data into the multinomial distribution according to equation 1 lets one immediately realize that the mean overall derivatization of the protein is indeed 8.4 out of 12 total conjugation sites, amounting to 70.1%.

To further illustrate the value of considering the overall derivatization of a molecule for process optimization, this value was employed as a response parameter for a Design-of-Experiment (DOE) approach with the goal to optimize reaction conditions that yielded maximum protein PEGylation. These results were compared to data analysis when the experimental output of conjugation for individual subunits was chosen. As described in the experimental section, a Box-Behnken design was employed. FIGS. 14A and 14B exemplify the response surface plots for the first round of studies, demonstrating the effect of reagent concentration on overall PEGylation efficiency for time points from 10 minutes to 2 hours. Whereas FIG. 14A illustrates the data based on an analysis of "fully PEGylated subunit" (i.e. 3 out of 3 functionalized conjugation sites per monomer) as directly obtained from the RP HPLC assay trace, FIG. 14B illustrates the data analysis when the overall derivatization is computed based on equation (1). Both panels show that PEGylation efficiency is increased with increasing concentrations of PEG. However, conclusions are different for the two ways of analysis: If, for example, a conjugation efficiency of >90% is the target, the analysis based on FIG. 14A might lead process developers to add at least 2-fold higher concentration of PEG and incubate for longer reaction times compared to the analysis based on overall derivatization (FIG. 14B). This apparent difference becomes more pronounced the more conjugation sites are present per subunit. Choosing only the maximum conjugation per subunit as response parameter instead of overall computed derivatization does not provide the true picture of the functionalization for an oligomeric molecule and might be misleading. Considering the high cost of PEG and other conjugation reagents, process optimization based on overall derivatization can result in significant cost-of-goods (as well as time) savings.

This example provides an applicable statistical approach based on a multinomial distribution that allows the computation of overall protein conjugation for oligomeric proteins when the size and nature of the protein or the biophysical properties of the conjugate do not allow analysis under native conditions. The quantitative description of overall molecule derivatization computed according to equation (1) will support both process optimization efforts as well as the accurate characterization of the conjugate for regulatory filings, and hopefully aid in the successful translation of novel bioconjugates to the clinic.

REFERENCES

Aly, M., Turkish Journal of Biology, 37, (2013) 520-529.
Anderson, A., Journal of Experimental Sciences, 2 (2011) 05-08.
Batista-Viera, F., J. Carlsson, Preparative Biochemistry, 7 (1977) 102-110.
Bongaerts, G. P., Biochim Biophys Acta, 27 (1978) 348-58.
Chen, R, Biochim. Biophys. Acta., 660 (1981) 293-298.
Chen, Y., African Journal of Biotechnology, 9 (2010) 4788-4795.
Chun, Z., Biosci. Biotechnol. Biochem. 74 (2010) 1298-1301.
da Silva Freitas, D., International Journal of Pharmaceutics 387 (2010) 215-222.
Davidson, J. N., Journal of Biochemistry, 32, (1938) 1386.
Davidson, J. N., Nature, 141, (1938) 790.
Davis S., Lancet. 8241 (1981) 281-283.
Fayyadh, M. Current Research in Microbiology and Biotechnology, 2 (2014) 384-390.
Geweely, N., Australian Journal of Basic and Applied Sciences, 10 (2011) 220-230.
Giffard, M., PloS ONE, 6 (2011) 1-9.
Habeeb, A. F., Anal. Biochem., 14 (1966), 328-336.
Holmberg, C. G., Journal of Biochemistry, 33 (1939) 1901-1906.
Hongoh, Y., Insect Biochemistry and Molecular Biology, 30 (2000) 173-182.
Ikeda, A., et al., Tumor Lysis Syndrome Clinical Presentation, Medscape (Dec. 3, 2014).
Itaya, K., Agr. Biol. Chem, 31 (1967) 1256-1264.
Liu, J., Annals of the New York Academy Sciences, 750 (2006) 477-481.
Lucas, K, Archives of Biochemistry and Biophysics, 11 (1983) 190-7.
Mabrouk, A., Gate2Biotech, 2, (2010) 1-13.
Machida, Y., Agricultural and Biological Chemistry, 44 (1980) 2811-2815.
Montalbini, P., Plant Science. 147 (1999) 139-147.
Nanda, P., International Journal of Pharmaceutical Technology, 1 (2011) 2277-3436.
Nanda, P., Research in Biotechnology, 3 (2012) 35-46.

Ortlund, Proceedings of the National Academy of Sciences of the United States, 10 (2014) 3763-3768.
Pfrimer, P., Journal of Biomedicine and Biotechnology, (2010) 1-6.
Poovizh, T., Internation Journal of Advanced Research, 2 (2014) 34-40.
Redondo, J, Planta, 202 (1997) 3.
Salleh, A. B., Pertanika, 3 (1980) 97-102.
Sherman, M. et al., Adv. Drug. Deliv. Rev. 60 (2008) 59-68.
Tian, H., Journal of Pharmacy and Pharmacology, 65 (2013) 53-63.
Watanabe, T., Analytical Biochemistry, 89 (1978) 343-347.
Watanabe, T., Analytical Biochemistry, 86 (1978) 357-362.
Wertheimer, A., et al., A Revised Estimate of the Burden of Illness of Gout, Curr Ther Res Clin Exp 75:1-4 (2013).
Zhang, C., PLOS ONE, 7 (2012).

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +1-5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A uricase comprising an amino acid sequence having at least 95% sequence identity to the amino acid sequence set forth in SEQ ID NO:1, wherein said uricase comprises a cysteine residue in at least one of the following amino acid positions: 11C, 33C, 119C, 120C, 142C, 196C, 238C, 286C, and 289C, wherein the position numbering is relative to the amino acid sequence of SEQ ID NO:27, and wherein said uricase has uricase activity.

2. The uricase of claim 1, wherein at least one of said cysteine residues of the uricase is PEGylated.

3. A pharmaceutical composition comprising the uricase of claim 1.

4. A method of reducing levels of uric acid and/or urate crystal burden in a hyperuricemic patient comprising administering the pharmaceutical composition of claim 3.

5. The method of claim 4, wherein the hyperuricemic patient has gout.

6. The method of claim 5, wherein the hyperuricemic patient has chronic refractory gout and/or tophaceous gout.

7. The method of claim 4, wherein the hyperuricemic patient has tumor lysis syndrome.

8. The method of claim 4, wherein the pharmaceutical composition is administered subcutaneously or intravenously.

* * * * *